United States Patent [19]
Lohmann et al.

[11] Patent Number: 5,962,458
[45] Date of Patent: Oct. 5, 1999

[54] SUBSTITUTED QUINAZOLINES

[75] Inventors: Jean-Jacques Marcel Lohmann, Merfy; Laurent Francois Andre Hennequin, Champigny sur Vesles, both of France; Andrew Peter Thomas, Congleton, United Kingdom

[73] Assignees: Zeneca Limited, London, United Kingdom; Zeneca Pharma S.A.,, Cergy Cedex, France

[21] Appl. No.: 08/768,887

[22] Filed: Dec. 17, 1996

[30] Foreign Application Priority Data

Dec. 18, 1995 [EP] European Pat. Off. .............. 95402846
Oct. 15, 1996 [EP] European Pat. Off. .............. 96402190

[51] Int. Cl.[6] ...................... A61K 31/505; C07D 239/72; C07D 401/00; C07D 403/00
[52] U.S. Cl. .......................... 514/259; 544/284; 544/287; 544/293
[58] Field of Search .................. 544/287, 293, 544/284; 514/259

[56] References Cited

U.S. PATENT DOCUMENTS

| | | | |
|---|---|---|---|
| 3,266,990 | 8/1966 | Lutz et al. | 167/65 |
| 4,343,940 | 8/1982 | Kreighbaum et al. | 544/283 |
| 5,457,105 | 10/1995 | Barker | 514/234.5 |

FOREIGN PATENT DOCUMENTS

| | | |
|---|---|---|
| 0 326 307 | 2/1989 | European Pat. Off. . |
| 0 326 330 A2 | 8/1989 | European Pat. Off. . |
| 0 520 722 A1 | 12/1992 | European Pat. Off. . |
| 0 566 226 A1 | 10/1993 | European Pat. Off. . |
| 0 602 851 A1 | 6/1994 | European Pat. Off. . |
| 0 635 498 A1 | 1/1995 | European Pat. Off. . |
| 0 635 507 A1 | 1/1995 | European Pat. Off. . |
| 0 682 027 A1 | 11/1995 | European Pat. Off. . |
| 0787722A1 | 8/1997 | European Pat. Off. . |
| 19528672 | 2/1997 | Germany . |
| 2 033 894 | 5/1980 | United Kingdom . |
| 2 160 201 | 12/1985 | United Kingdom . |
| WO 92/14716 | 9/1992 | WIPO . |
| WO 92/20642 | 11/1992 | WIPO . |
| WO 95/06648 | 3/1995 | WIPO . |
| WO 95/15758 | 6/1995 | WIPO . |
| WO 95/15952 | 6/1995 | WIPO . |
| WO 95/19169 | 7/1995 | WIPO . |
| WO 95/19774 | 7/1995 | WIPO . |
| WO 95/19970 | 7/1995 | WIPO . |
| WO 95/21613 | 8/1995 | WIPO . |
| WO 95/23141 | 8/1995 | WIPO . |
| WO 95/24190 | 9/1995 | WIPO . |
| WO 96/07657 | 3/1996 | WIPO . |
| WO 96/09294 | 3/1996 | WIPO . |
| WO 96/15118 | 5/1996 | WIPO . |
| WO 96/16960 | 6/1996 | WIPO . |
| WO 96/29331 | 9/1996 | WIPO . |
| WO 96/30347 | 10/1996 | WIPO . |
| WO 96/31520 | 10/1996 | WIPO . |
| WO 96/33977 | 10/1996 | WIPO . |

(List continued on next page.)

OTHER PUBLICATIONS

Rewcastle et al., "Tyrosine Kinase Inhibitors. 5. Synthesis and Structure–Activity Relationships for 4-[(Phenylmethyl)amino]–and 4-(Phenylamino)quinazolines as Potent Adenosine 5'–Triphosphate Binding Site Inhibitors of the Tyrosine Kinase Domain of the Epidermal Growth Factor Receptor," J.Med.Chem. 1995, vol. 38, pp.3482–3487.

Burke, Jr., "Protein–tyrosine kinase inhibitors," Drugs of the Future 1992, vol. 17(2), pp. 119–131.

Spence, "Inhibitors of Tyrosine Kinase Activity as Anticancer Therapeutics: Recent Developments," Current Opinion in Therapeutic Patents, Jan. 1993, Patent Update, Anticancers, etc., pp. 3–9, Current Drugs Ltd ISSN 0962–2594,.

Spada, et al., Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

(List continued on next page.)

Primary Examiner—Mukund J. Shah
Assistant Examiner—Bruck Kifle
Attorney, Agent, or Firm—Pillsbury Madison & Sutro

[57] ABSTRACT

The invention relates to quinazoline derivatives of the formula:

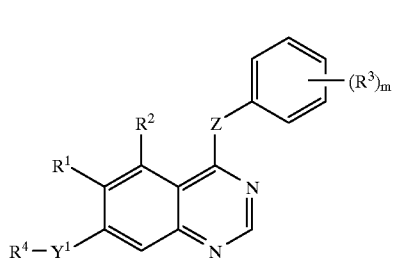

(I)

[wherein:
$Y^1$ represents —O—, —S—, —$CH_2$—, —SO—, —$SO_2$—, —$NR^5CO$—, —$CONR^6$-, —$SO_2NR^7$-, —$NR^8SO_2$— or —$NR^9$- (wherein $R^5$, $R^6$, $R^7$, $R^8$ and $R^9$ each independently represents hydrogen, alkyl or alkoxyalkyl);
$R^1$ represents hydrogen, hydroxy, halogeno, nitro, trifluoromethyl, cyano, alkyl, alkoxy, alkylthio, amino or alkylamino.
$R^2$ represents hydrogen, hydroxy, halogeno, alkyl, alkoxy, trifluoromethyl, cyano, amino or nitro;
m is an integer from 1 to 5;
$R^3$ represents hydroxy, halogeno, alkyl, alkoxy, alkanoyloxy, trifluoromethyl, cyano, amino or nitro;
$R^4$ represents a group which is or which contains an optionally substituted pyridone, phenyl or aromatic heterocyclic group] and salts thereof; processes for their preparation and pharmaceutical compositions containing a compound of formula I or a pharmaceutically acceptable salt thereof as active ingredient. The compounds of formula I and the pharmaceutically acceptable salts thereof inhibit the effects of VEGF, a property of value in the treatment of a number of disease states including cancer and rheumatoid arthritis.

14 Claims, No Drawings

FOREIGN PATENT DOCUMENTS

| | | |
|---|---|---|
| WO 96/33978 | 10/1996 | WIPO . |
| WO 96/33979 | 10/1996 | WIPO . |
| WO 96/33980 | 10/1996 | WIPO . |
| WO 96/33981 | 10/1996 | WIPO . |
| WO 96/34867 | 11/1996 | WIPO . |
| WO 96/35689 | 11/1996 | WIPO . |
| WO 96/39145 | 12/1996 | WIPO . |
| WO 96/40142 | 12/1996 | WIPO . |
| WO 96/40648 | 12/1996 | WIPO . |
| WO 97/02266 | 1/1997 | WIPO . |
| WO 97/3069 | 1/1997 | WIPO . |
| WO 97/13760 | 4/1997 | WIPO . |
| WO 97/13771 | 4/1997 | WIPO . |
| WO 97/18212 | 5/1997 | WIPO . |

OTHER PUBLICATIONS

Bridges, "The current status of tyrosine kinase inhibitors: do the diarylamine inhibitors of the EGF receptor represent a new beginning?," Exp.Opin.Ther.Patents (1995), 5(12): 1245–1257, Editorial, Oncologic, Endocrine & Metabolic, 1995 Ashley Publications Ltd ISSN 1354–3776.

Traxler, et al., "Recent advances in protein tyrosine kinase inhibitors," Drugs of the Future 1995, vol. 20(12, pp. 1261–1274.

Iyer, et al., "Studies in Potential Amoebicides: Part III–Synthesis of $_4$–Substituted Amino–8–Hydroxy) Quinazolines & $_3$–Substituted 8–Hydroxy(&8–Methoxy)–$_4$–Quinazolones," J.Sci.Industr.Res., vol. 15C, Jan. 1956, pp.1–7.

Derwent Abstract 82–87077, vol. 6, No. 244, Dec. 1982, JP 57–144266, Kobayashi, Sep. 1982, "4–Anilinoquinazoline Derivative, its Preparation and Analgesic and Antiphlogistic Agent Containing Said Derivatives as Active Component".

Derwent Abstract 81–28290, JP 56–20577, Feb. 1981, Sankyo and Ube, "4–(N–alkyl:anilino) quinazoline derivs . . . having analgesic and antiinflammatory actions".

Derwent Abstract 84–53835, JP 59–13765, Jan. 1984, Kyorin, "2–(4–Quinazolinyl)amino benzoic acid derivs . . . having analgesic and antiinflammatory activities".

Chem.Abs., vol. 92:76455u, 1980, pp.674–675, Li, et al.

Chem.Abs., vol. 96:122728w, 1982, p.695, Lin et al.

Fry et al., "A Specific Inhibitor of the Epidermal Growth Factor Receptor Tyrosine Kinase," Science, vol. 265, Aug. 19, 1994, pp. 1093–1095.

Buchdunger, et al., "4,5–Dianilinophthalimide: A protein–throsine kinase inhibitor with selectivity for the epidermal growth factor receptor signal transduction pathway and potent in vivo antitumor activity," Prac.Natl.Acad.Sci., USA, vol. 91, pp. 2334–2338, Mar. 1994, Applied Biological Sciences.

Trinks, et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.

Maguire, et al., "A New Series of PDGF Receptor Tyrosine Kinase Inhibitors: 3–Substituted Quinoline Derivatives," J.Med.Chem. 1994, vol. 37, pp. 2129–2137.

Dolle, et al., "5,7–Dimethoxy–3–(4–pyridinyl)quinoline Is a Potent and Selective Inhibitor of Human Vascular β–Type Platelet–Derived Growth Factor Receptor Tyrosine Kinase," J.Med.Chem. 1994, vol. 37, pp. 2627–2629.

Bridges, et al., "Enantioselective Inhibition of the Epidermal Growth Factor Receptor Tyrosine Kinase by 4–(α–Phenethylamino)quinazolines," Bioorganic & Medicinal Chemistry, vol. 3, No. 12, pp. 1651–1656, 1995.

Ward, et al., "Epidermal Growth Factor Receptor Tyrosine Kinase—Investigation of Catalytic Mechanism, Structure–Based Searching and Discovery of a Potent Inhibitor," Biochem.Pharmacology, vol. 48, No. 4, pp. 659–666 (1994).

Senger et al., Vascular permeability factor (VPF, VEGF) in tumor biology, Cancer and Metastasis Reviews, 1993, pp.303–324.

Kolch et al., Regulation of the expression of the VEGF/VPS and its receptors: role in tumor angiogenesis, Breast Cancer Research and Treatment, 1995, pp. 139–155.

Folkman, Angiogenesis in cancer, vascular, rheumatoid and other disease, Nature Medicine, 1995, pp. 27–31.

Cullinan–Bove et al., Vascular Endothelial Growth Factor/Vascular Permeability Factor Expression in the Rat Uterus: Rapid Stimulation by Estrogen Correlates with Estrogen–Induced Increases in Uterine Cappillary Permeability and Growth, Endocrinology, 1993, pp. 829–837.

Connolly et al., Human Vascular Permeability Factor—Isolation from U937 Cells, J. Biol. Chem. 1989, pp. 20017–20024.

Fan et al., Controlling the vasculature: angiogenesis, anti–angiogenesis and vascular targeting of gene therapy, Trends Pharmacol. Sci., 1995, 57–66.

Kim et al., Inhibition of vascular endothelial growth factor–induced angiogenesis suppresses tumour growth in vivo, Nature, 1983, pp. 841–844.

Jakeman et al., Developmental Expression of Binding Sites and Messenger Ribonucleic Acid for Vascular Endothelial Growth Factor Suggests a Role for This Protein in Vasculogenesis and Angiogenesis, Endocrinology, 1993, pp. 848–859.

SUBSTITUTED QUINAZOLINES

The present invention relates to quinazoline derivatives, processes for their preparation, pharmaceutical compositions containing them as active ingredient, methods for the treatment of disease states associated with angiogenesis and/or increased vascular permeability and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

Compounds which have good activity against epidermal growth factor (EGF) receptor tyrosine kinase are disclosed in the European Patent No. 0566226. The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess higher potency against VEGF receptor tyrosine kinase than against EGF receptor tyrosine kinase. Furthermore, compounds of the present invention, possess substantially higher potency against VEGF receptor tyrosine kinase than against EGF receptor tyrosine kinase or FGF R1 receptor tyrosine kinase. Thus compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase or FGF R1 receptor tyrosine kinase.

According to one aspect of the present invention there is provided a quinazoline derivative of the formula I:

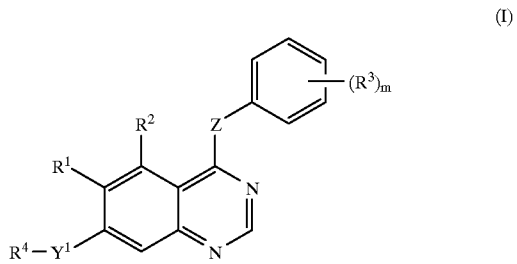

(I)

[wherein:
$Y^1$ represents —O—, —S—, —$CH_2$—, —SO—, —$SO_2$—, —$NR^5CO$—, —$CONR^6$-, —$SO_2NR^7$-, —$NR^8SO_2$— or —$NR^9$- (wherein $R^5$, $R^6$, $R^7$, $R^8$ and $R^9$ each independently represents hydrogen, $C_{1-3}$alkyl or $C_{1-3}$alkoxy$C_{2-3}$alkyl);

$R^1$ represents hydrogen, hydroxy, halogeno, nitro, trifluoromethyl, cyano, $C_{1-3}$alkyl, $C_{1-3}$alkoxy, $C_{1-3}$alkylthio, or $NR^{10}R^{11}$ (wherein $R^{10}$ and $R^{11}$, which may be the same or different, each represents hydrogen or $C_{1-3}$alkyl);

$R^2$ represents hydrogen, hydroxy, halogeno, $C_{1-3}$alkyl, $C_{1-3}$alkoxy, trifluoromethyl, cyano, amino or nitro;

m is an integer from 1 to 5;

$R^3$ represents hydroxy, halogeno, $C_{1-3}$alkyl, $C_{1-3}$alkoxy, $C_{1-3}$alkanoyloxy, trifluoromethyl, cyano, amino or nitro;

$R^4$ is selected from one of the following eight groups:
1) $X^1$ (wherein $X^1$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{12}R^{13}$ and —$NR^{14}COR^{15}$ (wherein $R^{12}$, $R^{13}$, $R^{14}$ and $R^{15}$, which may be the same or different, each represents hydrogen, $C_{1-4}$alkyl or $C_{1-3}$alkoxy$C_{2-3}$alkyl));
2) $C_{1-5}$alkyl$X^1$ (wherein $X^1$ is as defined hereinbefore);
3) $C_{2-5}$alkenyl$X^1$ (wherein $X^1$ is as defined hereinbefore);
4) $C_{2-5}$alkynyl$X^1$ (wherein $X^1$ is as defined hereinbefore);
5) $C_{1-5}$alkyl$Y^2X^1$ (wherein $Y^2$ represents —O—, —S—, —SO—, —$SO_2$—, —OCO—, —$NR^{16}CO$—, —$CONR^{17}$-, —$SO_2NR^{18}$-, —$NR^{19}SO_2$— or —$NR^{20}$- (wherein $R^{16}$, $R^{17}$, $R^{18}$, $R^{19}$ and $R^{20}$ each independently represents hydrogen, $C_{1-3}$alkyl or $C_{1-3}$alkoxy$C_{2-3}$alkyl) and $X^1$ is as defined hereinbefore);

6) $C_{2-5}$alkenyl$Y^3X^1$ (wherein $Y^3$ represents —O—, —S—, —SO—, —SO$_2$—, —OCO—, —NR$^{21}$CO—, —CONR$^{22}$-, —SO$_2$NR$^{23}$-, —NR$^{24}$SO$_2$— or —NR$^{25}$- (wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $X^1$ is as defined hereinbefore);

7) $C_{2-5}$alkynyl$Y^4X^1$ (wherein $Y^4$ represents —O—, —S—, —SO—, —SO$_2$—, —OCO—, —NR$^{26}$CO—, —CONR$^{27}$-, —SO$_2$NR$^{28}$-, —NR$^{29}$SO$_2$— or —NR$^{30}$- (wherein $R^{26}$, $R^{27}$, $R^{28}$, $R^{29}$ and $R^{30}$ each independently represents hydrogen, $C_{1-3}$alkyl or $C_{1-3}$alkoxy$C_{2-3}$alkyl) and $X^1$ is as defined hereinbefore); and 8) $C_{1-3}$alkyl$Y^5C_{1-3}$alkyl$X^1$ (wherein $Y^5$ represents —O—, —S—, —SO—, —SO$_2$—, —NR$^{31}$CO—, —CONR$^{32}$-, —SO$_2$NR$^{33}$-, —NR$^{34}$SO$_2$— or —NR$^{35}$- (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $X^1$ is as defined hereinbefore);

Z represents —NH—, —O—, —S—, or —CH$_2$—; with the proviso that where $R^4$ is selected from one of the groups 1), 2), and 5) above and $X^1$ is unsubstituted phenyl or substituted phenyl with 1 to 2 substituents selected from halogeno, $C_{1-4}$alkyl and $C_{1-4}$alkoxy, then m is an integer from 3 to 5 and/or Z is —O—, —S—, or —CH$_2$—];
and salts thereof.

Advantageously $Y^1$ represents —O—, —S—, —CH$_2$—, —NR$^5$CO—, —NR$^8$SO$_2$— or —NR$^9$- (wherein $R^5$, $R^8$ and $R^9$ each independently represents hydrogen, $C_{1-2}$alkyl or $C_{1-2}$alkoxyethyl).

Preferably $Y^1$ represents —O—, —S—, —CH$_2$—, —NR$^5$CO—, —NR$^8$SO$_2$— or —NH— (wherein $R^5$ and $R^8$ each independently represents hydrogen, $C_{1-2}$alkyl or $C_{1-2}$alkoxyethyl).

More preferably $Y^1$ represents —O—, —S—, —CH$_2$— or —NH—, especially —O—.

In another embodiment of the present invention $Y^1$ represents —O—, —NR$^5$CO— or —NR$^8$SO$_2$— (wherein $R^5$ and $R^8$ each independently represents hydrogen or $C_{1-2}$alkyl).

In a further embodiment of the present invention $Y^1$ is —NHCO—.

In one embodiment of the invention $R^1$ represents hydrogen, hydroxy, $C_{1-3}$alkyl, $C_{1-3}$alkoxy, $C_{1-3}$alkylthio, or $NR^{10}R^{11}$ (wherein $R^{10}$ and $R^{11}$ are as defined hereinbefore). Conveniently however $R^1$ is hydrogen, hydroxy, cyano, nitro, trifluoromethyl, $C_{1-3}$alkyl, $C_{1-3}$alkoxy or amino.

$R^1$ is advantageously hydrogen, hydroxy, $C_{1-3}$alkyl, $C_{1-3}$alkoxy or amino.

$R^1$ is preferably hydrogen, hydroxy, methyl, ethyl, methoxy or ethoxy, more preferably hydrogen, hydroxy, methyl or methoxy, particularly hydrogen, methyl or methoxy but especially methoxy.

In another embodiment of the present invention $R^1$ represents hydrogen, hydroxy, cyano, nitro, trifluoromethyl, methyl, ethyl, methoxy or ethoxy.

$R^2$ is advantageously hydrogen, halogeno, amino or nitro.

$R^2$ is preferably hydrogen, chloro or nitro, but especially hydrogen.

In one embodiment of the present invention $R^3$ represents hydroxy, halogeno, $C_{1-3}$alkyl, $C_{1-3}$alkoxy, trifluoromethyl, cyano, amino or nitro.

Advantageously in another embodiment of the present invention one $R^3$ substituent is meta-hydroxy and the other one or more are each selected from halogeno and methyl.

In another embodiment of the invention the phenyl group bearing $(R^3)_m$ is of the formula IIa:

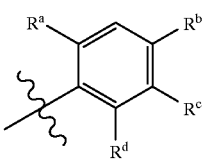

(IIa)

(wherein:
$R^a$ represents hydrogen, methyl, fluoro or chloro;
$R^b$ represents hydrogen, methyl, methoxy, bromo, fluoro or chloro;
$R^c$ represents hydrogen or hydroxy;
$R^d$ represents hydrogen, fluoro or chloro, especially hydrogen or fluoro).

In a further embodiment of the invention the phenyl group bearing $(R^3)_m$ is preferably of the formula IIa wherein:
$R^a$ represents hydrogen, fluoro or chloro;
$R^b$ represents hydrogen, methyl, methoxy, bromo, fluoro or chloro, especially hydrogen, methyl or chloro;
$R^c$ represents hydrogen or hydroxy; and
$R^d$ represents hydrogen;
with the proviso that $R^a$, $R^b$ and $R^c$ do not each represent hydrogen.

Preferably the phenyl group bearing $(R^3)_m$ is the 3-hydroxy-4-methylphenyl group, the 2-fluoro-5-hydroxy-4-methylphenyl group, the 2-fluoro-4-bromophenyl, the 2-fluoro-4-chloro-5-hydroxyphenyl or the 4-chloro-2-fluorophenyl group.

In a particular aspect of the present invention, the phenyl group bearing $(R^3)_m$ is the 3-hydroxy-4-methylphenyl group, but especially the 2-fluoro-5-hydroxy-4-methylphenyl group.

In a further embodiment of the present invention the phenyl group bearing $(R^3)_m$ is the 4-chloro-2-fluorophenyl group.

Advantageously $Y^2$ represents —O—, —S—, —SO—, —SO$_2$—, —NR$^{16}$CO—, —NR$^{19}$ SO$_2$— or —NR$^{20}$- (wherein $R^{16}$, $R^{19}$ and $R^{20}$ each independently represents hydrogen, $C_{1-2}$alkyl or $C_{1-2}$alkoxyethyl).

Preferably $Y^2$ represents, —O—, —S—, —SO—, —SO$_2$— or —NR$^{20}$- (wherein $R^{20}$ represents hydrogen, $C_{1-2}$alkyl or $C_{1-2}$alkoxyethyl).

More preferably $Y^2$ represents —S—, —O— or —NR$^{20}$- (wherein $R^{20}$ represents hydrogen or $C_{1-2}$alkyl), but most preferably is —O—, or —NR$^{20}$ (wherein $R^{20}$ is as hereinbefore defined).

Advantageously $Y^3$ represents —O—, —S—, —SO—, —SO$_2$—, —NR$^{21}$CO—, —NR$^{24}$SO$_2$— or —NR$^{25}$- (wherein $R^{21}$, $R^{24}$ and $R^{25}$ each independently represents hydrogen, $C_{1-2}$alkyl or $C_{1-2}$alkoxyethyl).

Preferably $Y^3$ represents —O—, —S—, —SO—, —SO$_2$— or —NR$^{25}$- (wherein $R^{25}$ represents hydrogen, $C_{1-2}$alkyl or $C_{1-2}$alkoxyethyl).

More preferably $Y^3$ represents —O— or —NR$^{25}$- (wherein $R^{25}$ represents hydrogen or $C_{1-2}$alkyl).

Advantageously $Y^4$ represents —O—, —S—, —SO—, —SO$_2$—, —NR$^{26}$CO—, —NR$^{29}$SO$_2$— or —NR$^{30}$- (wherein $R^{26}$, $R^{29}$ and $R^{30}$ each independently represents hydrogen, $C_{1-2}$alkyl or $C_{1-2}$alkoxyethyl).

Preferably $Y^4$ represents —O—, —S—, —SO—, —SO$_2$— or —NR$^{30}$- (wherein $R^{30}$ represents hydrogen, $C_{1-2}$alkyl or $C_{1-2}$alkoxyethyl).

More preferably $Y^4$ represents —O— or —NR$^{30}$- (wherein $R^{30}$ represents hydrogen or $C_{1-2}$alkyl).

Advantageously $Y^5$ represents —O—, —S—, —SO—, —SO$_2$— or —NR$^{35}$- (wherein R$^{35}$ represents hydrogen, C$_{1-2}$alkyl or C$_{1-2}$alkoxyethyl).

Preferably $Y^5$ represents —O—, —S— or —NR$^{35}$- (wherein R$^{35}$ represents hydrogen, C$_{1-2}$alkyl or C$_{1-2}$alkoxyethyl).

m is preferably 2 or 3.

Z may for example represent —NH— or —O— but Z is preferably —NH—.

$X^1$ preferably represents a pyridone group or a 5 or 6-membered aromatic heterocyclic group with 1 to 3 heteroatoms selected from O, N and S, which pyridone group or heterocyclic group may be substituted as hereinbefore defined.

Where $X^1$ is a 5 or 6-membered aromatic heterocyclic group, it preferably has 1 or 2 heteroatoms, selected from O, N and S, of which more preferably one is N, and may be substituted as hereinbefore defined.

$X^1$ is particularly a pyridone, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

Where $R^4$ is C$_{1-5}$alkylX$^1$, C$_{2-5}$alkenylX$^1$, C$_{2-5}$alkynylX$^1$ or C$_{1-3}$alkylY$^5$C$_{1-3}$alkylX$^1$, and $X^1$ is a nitrogen-containing 6-membered aromatic heterocyclic group, said group is advantageously linked to the alkyl, alkenyl or alkynyl moiety via a carbon atom of $X^1$, said group being such that a nitrogen atom is positioned para- to the carbon atom linked to the alkyl, alkenyl or alkynyl moiety. The C$_{1-5}$alkyl moiety may if desired be —(CH$_2$)$_n$—.

Where $R^4$-$Y^1$ is $X^1$—(CH$_2$)$_n$—$Y^1$- and n is an integer from 0 to 5, $Y^1$ is —O—, —NH—, —S— or —CH$_2$— and $X^1$ is a nitrogen-containing 6-membered aromatic heterocyclic group, said group is advantageously linked to —(CH$_2$)$_n$—$Y^1$- via a carbon atom of $X^1$, said group being such that a nitrogen atom is positioned para- to the carbon atom linked to —(CH$_2$)$_n$—$Y^1$-.

In another example of interest, $X^1$ is pyrimidine which may be substituted as hereinbefore defined.

In one embodiment of the invention $X^1$ represents a pyridone, phenyl or 5 or 6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $X^1$, conveniently substituents are selected from halogeno, C$_{1-4}$alkyl, C$_{1-4}$alkoxy and cyano, more conveniently substituents are selected from chloro, fluoro, methyl and ethyl.

Conveniently $R^4$ is selected from one of the following eight groups:
1) $X^1$ (wherein $X^1$ is as defined hereinbefore);
2) C$_{1-5}$alkylX$^1$ (wherein $X^1$ is as defined hereinbefore);
3) C$_{3-5}$alkenylX$^1$ (wherein $X^1$ is as defined hereinbefore);
4) C$_{3-5}$alkynylX$^1$ (wherein $X^1$ is as defined hereinbefore);
5) C$_{1-5}$alkylY$^2$X$^1$ (wherein $Y^2$ and $X^1$ are as defined hereinbefore);
6) C$_{3-5}$alkenylY$^3$X$^1$ (wherein $Y^3$ and $X^1$ are as defined hereinbefore);
7) C$_{3-5}$alkynylY$^4$X$^1$ (wherein $Y^4$ and $X^1$ are as defined hereinbefore); and
8) C$_{2-3}$alkylY$^5$C$_{1-2}$alkylX$^1$ (wherein $Y^5$ and $X^1$ are as defined hereinbefore).

Advantageously $R^4$ is selected from one of the following eight groups:
1) $X^1$ (wherein $X^1$ is as defined hereinbefore);
2) C$_{1-5}$alkylX$^1$ (wherein $X^1$ is as defined hereinbefore);
3) 1-X$^1$prop-1-en-3-yl, 1-X$^1$but-2-en-4-yl, 1-X$^1$but-1-en-3-yl, 1-X$^1$pent-2-en-4-yl or 2-X$^1$pent-3-en-5-yl (wherein $X^1$ is as defined hereinbefore with the proviso that when $R^4$ is 1-X$^1$prop-1-en-3-yl, $X^1$ is linked to the alkenyl group via a carbon atom);
4) 1-X$^1$prop-1-yn-3-yl, 1-X$^1$but-2-yn-4-yl, 1-X$^1$but-1-yn-3-yl, 1-X$^1$pent-2-yn-4-yl or 2-X$^1$pent-3-yn-5-yl (wherein $X^1$ is as defined hereinbefore with the proviso that when $R^4$ is 1-X$^1$prop-1-yn-3-yl, $X^1$ is linked to the alkynyl group via a carbon atom);
5) C$_{1-5}$alkylY$^2$X$^1$ (wherein $Y^2$ and $X^1$ are as defined hereinbefore);
6) 1-(X$^1$Y$^3$)prop-1-en-3-yl, 1-(X$^1$Y$^3$)but-2-en-4-yl, 1-(X$^1$Y$^3$)but-1-en-3-yl, 1-(X$^1$Y$^3$)pent-2-en-4-yl or 2-(X$^1$Y$^3$)pent-3-en-5-yl (wherein $Y^3$ and $X^1$ are as defined hereinbefore);
7) 1-(X$^1$Y$^4$)prop-1-yn-3-yl, 1-(X$^1$Y$^4$)but-2-yn-4-yl, 1-(X$^1$Y$^4$)but-1-yn-3-yl, 1-(X$^1$Y$^4$)pent-2-yn-4-yl or 2-(X$^1$Y$^4$)pent-3-yn-5-yl (wherein $Y^4$ and $X^1$ are as defined hereinbefore); and
8) C$_{2-3}$alkylY$^5$C$_{1-2}$alkylX$^1$ (wherein $Y^5$ and $X^1$ are as defined hereinbefore).

Preferably $R^4$ is selected from one of the following eight groups:
1) $X^1$ (wherein $X^1$ is as defined hereinbefore);
2) C$_{1-5}$alkylX$^1$ (wherein $X^1$ is as defined hereinbefore);
3) 1-X$^1$but-2-en-4-yl (wherein $X^1$ is as defined hereinbefore);
4) 1-X$^1$but-2-yn-4-yl (wherein $X^1$ is as defined hereinbefore);
5) C$_{1-5}$alkylY$^2$X$^1$ (wherein $Y^2$ and $X^1$ are as defined hereinbefore);
6) 1-(X$^1$Y$^3$)but-2-en-4-yl (wherein $Y^3$ and $X^1$ are as defined hereinbefore);
7) 1-(X$^1$Y$^4$)but-2-yn-4-yl (wherein $Y^4$ and $X^1$ are as defined hereinbefore); and
8) ethylY$^5$methylX$^1$ (wherein $Y^5$ and $X^1$ are as defined hereinbefore).

More preferably the compounds of formula (I) are of the formula (Ia):

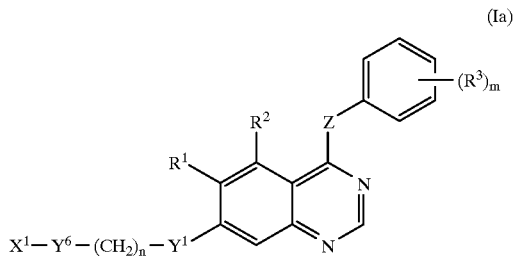

(Ia)

(wherein $R^1$, $R^2$, $R^3$, m, $X^1$, $Y^1$ and Z are as defined hereinbefore n is an integer from 0 to 5 and $Y^6$ represents a direct bond, —O—, —S—, —SO—, —SO$_2$—, —NR$^{36}$CO—, —CONR$^{37}$-, —SO$_2$NR$^{38}$-, —NR$^{39}$SO$_2$— or —NR$^{40}$- (wherein R$^{36}$, R$^{37}$, R$^{38}$, R$^{39}$ and R$^{40}$ each independently represents hydrogen, C$_{1-3}$alkyl or C$_{1-3}$alkoxyC$_{2-3}$alkyl)).

Advantageously $Y^6$ is a direct bond, —O—, —S—, —SO—, —SO$_2$— or —NR$^{40}$- (wherein R$^{40}$ represents hydrogen, C$_{1-2}$alkyl or C$_{1-2}$alkoxyethyl).

Preferably $Y^6$ is a direct bond, —O—, —S— or —NH—.

More preferably $Y^6$ is a direct bond.

n is advantageously an integer from 0 to 3, preferably 1 to 3.

Therefore, for example, in a particular embodiment of the invention the compounds of formula I are of the formula Ia wherein:

[$Y^1$ represents —O—, —NH—, —S— or —CH$_2$—;

n is an integer from 0 to 5;

$X^1$ represents a phenyl group or a 5 or 6-membered aromatic heterocyclic group with 1 to 3 heteroatoms selected from O, N and S, which phenyl or heterocyclic group may carry up to 5 substituents selected from halogeno, $C_{1-4}$alkyl, $C_{1-4}$alkoxy, $C_{1-4}$hydroxyalkyl, $C_{1-4}$hydroxyalkoxy, carboxy, cyano, —CONR$^{41}$R$^{42}$ and —NR$^{43}$COR$^{44}$ (wherein R$^{41}$, R$^{42}$, R$^{43}$ and R$^{44}$, which may be the same or different, each represents hydrogen or $C_{1-4}$alkyl);

$R^1$ represents hydrogen, hydroxy, $C_{1-3}$alkyl, $C_{1-3}$alkoxy, $C_{1-3}$alkylthio, or NR$^{45}$R$^{46}$ (wherein R$^{45}$ and R$^{46}$, which may be the same or different, each represents hydrogen or $C_{1-3}$alkyl);

$R^2$ represents hydrogen, hydroxy, halogeno, $C_{1-3}$alkyl, $C_{1-3}$alkoxy, trifluoromethyl, cyano, amino or nitro;

m is an integer from 1 to 5;

$R^3$ represents hydroxy, halogeno, $C_{1-3}$alkyl, $C_{1-3}$alkoxy, $C_{1-3}$alkanoyloxy, trifluoromethyl, cyano, amino or nitro;

Z represents —NH— or —O—; and $Y^6$ is a direct bond;

with the proviso that where $X^1$ is unsubstituted phenyl or substituted phenyl with 1 to 2 substituents selected from halogeno, $C_{1-4}$alkyl and $C_{1-4}$alkoxy, m is an integer from 3 to 5 or Z is —O—];

and salts thereof.

Preferred compounds of the present invention are:

4-(3-hydroxy-4-methylanilino)-6-methoxy-7-(3-pyridylmethoxy)quinazoline 4-(3-hydroxy-4-methylanilino)-6-methoxy-7-(3-thienylmethoxy)quinazoline 4-(4-chloro-2-fluoroanilino)-6-methoxy-7-(2-(2-pyridyloxy)ethoxy)quinazoline 4-(4-chloro-2-fluoroanilino)-6-methoxy-7-(2-([N-methyl-N-(4-pyridyl)]amino)ethoxy)quinazoline 4-(4-chloro-2-fluoroanilino)-6-methoxy-7-[2-(2-oxo-1,2-dihydro-1-pyridyl)ethoxy]quinazoline 7-(4 cyanobenzyloxy)-4-(2-fluoro-5-hydroxy-4-methylanilino)-6-methoxyquinazoline 4-(4-chloro-2-fluoroanilino)-6-methoxy-7-(3-(2-methylimidazol-1-yl)propoxy)quinazoline 4-(4-chloro-2-fluoroanilino)-6-methoxy-7-((2-methyl-4-pyridyl)methoxy)quinazoline 4-(4-chloro-2-fluoroanilino)-6-methoxy-7-(3-(2-oxo-1,2-dihydro-1-pyridyl)propoxy)quinazoline 4-(4-chloro-2-fluoroanilino)-6-methoxy-7-(3-(1-methylimidazol-2-ylthio)propoxy)quinazoline 4-(4-chloro-2-fluoroanilino)-6-methoxy-7-(3-(4-pyridyloxy)propoxy)quinazoline 4-(4-chloro-2-fluoroanilino)-6-methoxy-7-(2-(4-pyridylthio)ethoxy)quinazoline 4-(4-chloro-2-fluoroanilino)-6-methoxy-7-(2-(3-pyridyloxy)ethoxy)quinazoline 7-benzyloxy-4-(2-fluoro-5-hydroxy-4-methylanilino)quinazoline 7-benzyloxy-4-(4-chloro-2-fluoro-5-hydroxyanilino)quinazoline 4-(4-chloro-2-fluoro-5-hydroxyanilino)-6-methoxy-7-((2-methylthiazol-4-yl)methoxy)quinazoline 4-(4-chloro-2-fluoroanilino)-6-methoxy-7-(3-thienylmethoxy)quinazoline 4-(4-chloro-2-fluoroanilino)-6-methoxy-7-(2-(N-methyl-N-(pyridazin-4-yl)amino)ethoxy)quinazoline 4-(4-chloro-2-fluoroanilino)-6-methoxy-7-(2-(N-methyl-N-(6-methylpyrimidin-4-yl)amino)ethoxy)quinazoline 4-(4-chloro-2-fluoroanilino)-7-(2-(3,5-dimethyl-[1,2,4]-triazol-4-yl)ethoxy)-6-methoxyquinazoline 4-(4-chloro-2-fluoroanilino)-7-(2-(2,4-dimethylimidazol-1-yl)ethoxy)-6-methoxyquinazoline 4-(4-chloro-2-fluoroanilino)-7-(2-(2,5-dimethylimidazol-1-yl)ethoxy)-6-methoxyquinazoline 4-(3-hydroxyanilino)-7-(2-(imidazol-1-yl)ethoxy)-6-methoxyquinazoline 4-(4-chloro-2-fluoroanilino)-6-methoxy-7-(2-(1,2,4-triazol-4-yl)ethoxy)quinazoline 4-(4-bromo-2-fluoroanilino)-7-(2-([1,2,4]-triazol-1-yl)ethoxy)-6-methoxyquinazoline and salts thereof, especially hydrochloride salts thereof The following compounds of the present invention are especially preferred:

4-(3-hydroxy-4-methylanilino)-6-methoxy-7-(4-pyridylmethoxy)quinazoline 4-(3-hydroxy-4-methylanilino)-6-methoxy-7-(2-pyridylmethoxy)quinazoline 4-(3-hydroxy-4-methylanilino)-6-methoxy-7-(1-methylimidazol-2-ylmethoxy)quinazoline 4-(3-hydroxy-4-methylanilino)-6-methoxy-7-(2-methylthiazol-4-ylmethoxy)quinazoline 7-(2-acetamidothiazol-4-ylmethoxy)-4-(3-hydroxy-4-methylanilino)-6-methoxyquinazoline 4-(3-hydroxy-4-methylanilino)-6-methoxy-7-(3-(4-pyridyl)propoxy)quinazoline 4-(2-fluoro-5-hydroxy-4-methylanilino)-6-methoxy-7-(3-(4-pyridyl)propoxy)quinazoline 4-(2-fluoro-5-hydroxy-4-methylanilino)-6-methoxy-7-(4-pyridylmethoxy)quinazoline 7-benzyloxy-4-(2-fluoro-5-hydroxy-4-methylanilino)-6-methoxyquinazoline 4-(4-chloro-2-fluoroanilino)-6-methoxy-7-(2-(4-pyridyloxy)ethoxy)quinazoline 4-(4-chloro-2-fluoroanilino)-6-methoxy-7-[2-(4-oxo-1,4-dihydro-1-pyridyl)ethoxy]quinazoline 7-benzyloxy-4-(2-fluoro-5-hydroxy-4-methylphenoxy)-6-methoxyquinazoline 4-(2-fluoro-5-hydroxy-4-methylanilino)-6-methoxy-7-((2-methylthiazol-4-yl)methoxy)quinazoline 4-(2-fluoro-5-hydroxy-4-methylanilino)-7-(4-pyridylmethoxy)quinazoline 4-(4-chloro-2-fluoroanilino)-7-(2-(imidazol-1-yl)ethoxy)-6-methoxyquinazoline 4-(2-fluoro-5-hydroxy-4-methylanilino)-6-methoxy-7-((1-methylimidazol-2-yl)methoxy)quinazoline 7-((2-acetamidothiazol-4-yl)methoxy)-4-(2-fluoro-5-hydroxy-4-methylanilino)-6-methoxyquinazoline 7-benzyloxy-4-(4-chloro-2-fluoro-5-hydroxyanilino)-6-methoxyquinazoline 4-(4-chloro-2-fluoroanilino)-6-methoxy-7-(3-(4-pyridyl)propoxy)quinazoline 4-(4-chloro-2-fluoro-5-hydroxyanilino)-6-methoxy-7-(3-(4-pyridyl)propoxy)quinazoline 4-(2-fluoro-5-hydroxy-4-methylanilino)-7-(2-(imidazol-1-yl)ethoxy)-6-methoxyquinazoline 4-(4-chloro-2-fluoro-5-hydroxyanilino)-7-(2-(imidazol-1-yl)ethoxy)-6-methoxyquinazoline 4-(2-fluoro-5-hydroxy-4-methylanilino)-6-methoxy-7-(2-(4-pyridyl)ethoxy)quinazoline
4-(2-fluoro-5-hydroxy-4-methylanilino)-6-methoxy-7-(3-thienylmethoxy)quinazoline
4-(4-chloro-2-fluoroanilino)-6-methoxy-7-(2-(4-pyridyl)ethoxy)quinazoline
4-(3-hydroxy-4-methylanilino)-6-methoxy-7-((1-methylbenzimidazol-2-yl)methoxy)quinazoline
7-((2-chloro-6-methyl-4-pyridyl)methoxy)-4-(2-fluoro-5-hydroxy-4-methylanilino)-6-methoxyquinazoline
4-(4-chloro-2-fluorophenoxy)-6-methoxy-7-((4 pyridyl)methoxy)quinazoline
4-(4-chloro-2-fluoroanilino)-6-methoxy-7-((4 pyridyl)methoxy)quinazoline
4-(4-chloro-2-fluoroanilino)-6-methoxy-7-(2-(2-methylimidazol-1-yl)ethoxy)quinazoline
4-(4-chloro-2-fluoro-5-hydroxyanilino)-6-methoxy-7-((4-pyridyl)methoxy)quinazoline
7-((2-chloro-4-pyridyl)methoxy)-4-(2-fluoro-5-hydroxy-4-methylanilino)-6-methoxyquinazoline
4-(4-chloro-2-fluoroanilino)-6-methoxy-7-(2-(1-methylimidazol-2-ylthio)ethoxy)quinazoline
7-(3,4-difluorobenzyloxy)-4-(2-fluoro-5-hydroxy-4-methylanilino)-6-methoxyquinazoline
4-(4-chloro-2-fluoro-5-hydroxyanilino)-6-methoxy-7-((1-methylimidazol-2-yl)methoxy)quinazoline
4-(2-fluoro-5-hydroxy-4-methylanilino)-7-((1-methylimidazol-2-yl)methoxy)quinazoline
4-(2-fluoro-5-hydroxy-4-methylanilino)-7-(2-(1,2,4-triazol-1-yl)ethoxy)quinazoline
4-(4-chloro-2-fluoro-5-hydroxyanilino)-6-methoxy-7-(3-thienylmethoxy)quinazoline
4-(4-chloro-2-fluoro-5-hydroxyanilino)-6-methoxy-7-(2-(4-pyridyl)ethoxy)quinazoline
4-(4-chloro-2-fluoroanilino)-6-methoxy-7-(2-(1,2,4-triazol-1-yl)ethoxy)quinazoline
4-(2-fluoro-5-hydroxy-4-methylanilino)-7-((4-pyridyl)carboxamido)quinazoline
4-(4-chloro-2-fluoroanilino)-6-methoxy-7-(2-(N-(4-pyridyl)amino)ethoxy)quinazoline
4-(4-chloro-2-fluoroanilino)-6-methoxy-7-(2-(1-methylimidazol-2-yl)ethoxy)quinazoline
4-(4-chloro-2-fluoroanilino)-7-((2-cyano-4-pyridyl)methoxy)-6-methoxyquinazoline
and salts thereof, especially hydrochloride salts thereof,
of which the following are particularly preferred:
4-(4-chloro-2-fluoroanilino)-6-methoxy-7-(2-(4-pyridyloxy)ethoxy)quinazoline
4-(4-chloro-2-fluoroanilino)-6-methoxy-7-[2-(4-oxo-1,4-dihydro-1-pyridyl)ethoxy]quinazoline
4-(4-chloro-2-fluoroanilino)-7-(2-(imidazol-1-yl)ethoxy)-6-methoxyquinazoline
4-(4-chloro-2-fluoroanilino)-6-methoxy-7-(3-(4-pyridyl)propoxy)quinazoline
4-(4-chloro-2-fluoroanilino)-6-methoxy-7-(2-(4-pyridyl)ethoxy)quinazoline
4-(4-chloro-2-fluoroanilino)-6-methoxy-7-((4-pyridyl)methoxy)quinazoline
4-(4-chloro-2-fluoroanilino)-6-methoxy-7-(2-(2-methylimidazol-1-yl)ethoxy)quinazoline
4-(4-chloro-2-fluoroanilino)-6-methoxy-7-(2-(1-methylimidazol-2-ylthio)ethoxy)quinazoline
4-(4-chloro-2-fluoroanilino)-6-methoxy-7-(2-(1,2,4-triazol-1-yl)ethoxy)quinazoline
4-(4-chloro-2-fluoroanilino)-6-methoxy-7-(2-(N-(4-pyridyl)amino)ethoxy)quinazoline
4-(4-chloro-2-fluoroanilino)-6-methoxy-7-(2-(1-methylimidazol-2-yl)ethoxy)quinazoline
4-(4-chloro-2-fluoroanilino)-7-((2-cyano-4-pyridyl)methoxy)-6-methoxyquinazoline
and salts thereof, especially hydrochloride salts thereof.

Another compound of interest is 4-(3-hydroxy-4-methylanilino)-6-methoxy-7-(4-pyrimidinylmethoxy)quinazoline and salts thereof especially hydrochloride salts thereof.

For the avoidance of doubt it is to be understood that where in this specification a group is qualified by 'defined hereinbefore' the said group encompasses the first occurring and broadest definition as well as each and all of the preferred definitions for that group.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. The term "alkoxy" as used herein, unless stated otherwise includes "alkyl"-O-groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"-O-groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes alkylC=O groups in which "alkyl" is as defined hereinbefore, for example ethanoyl refers to $CH_3C$=O. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–6 carbon atoms, preferably 4–5 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–6 carbon atoms, preferably 4–5 carbon atoms.

In formula I, as hereinbefore defined, hydrogen will be present at positions 2 and 8 of the quinazoline group.

Within the present invention it is to be understood that a quinazoline of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain quinazolines of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $Y^1$ is, for example, a group of formula —$NR^5CO$—, it is the nitrogen atom bearing the $R^5$ group which is attached to the quinazoline ring and the carbonyl (CO) group is attached to $R^4$, whereas when $Y^1$ is, for example, a group of formula —CONR$^6$-, it is the carbonyl group which is attached to the quinazoline ring and the nitrogen atom bearing the $R^6$ group is attached to $R^4$. A similar convention applies to the other two atom $Y^1$ linking groups such as —NR$^8$SO$_2$— and —SO$_2$NR$^7$-. When $Y^1$ is —NR$^9$- it is the nitrogen atom bearing the $R^9$ group which is linked to the quinazoline ring and to $R^4$. An analogous convention applies to other groups. It is further to be understood that when $Y^1$ represents —NR$^9$- and $R^9$ is $C_{1-3}$alkoxyC$_{2-3}$alkyl it is the $C_{2-3}$alkyl moiety which is linked to the nitrogen atom of $Y^1$ and an analogous convention applies to other groups.

For the avoidance of any doubt, it is to be understood that in a compound of the formula I when $R^4$ is, for example, a group of formula $C_{1-5}$alkylY$^5$C$_{1-5}$alkylX$^1$, it is the terminal $C_{1-5}$alkyl moiety which is bound to $Y^1$, similarly when $R^4$ is, for example, a group of formula $C_{2-5}$alkenylX$^1$ it is the $C_{2-5}$alkenyl moiety which is bound to $Y^1$ and an analgous convention applies to other groups. When $R^4$ is a group 1-X$^1$prop-1-en-3-yl it is the first carbon to which the group $X^1$ is attached and it is the third carbon which is linked to $Y^1$, similarly when $R^4$ is a group 2-X$^1$pent-3-en-5-yl it is the second carbon to which the group $X^1$ is attached and it is the fifth carbon which is linked to $Y^1$, and an analogous convention applies to other groups.

For the avoidance of any doubt, it is to be understood that when $X^1$ carries a $C_{1-4}$aminoalkyl substituent it is the $C_{1-4}$alkyl moiety which is attached to $X^1$ whereas when $X^1$ carries a $C_{1-4}$alkylamino substituent it is the amino moiety which is attached to $X^1$ and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic acids such as with hydrogen halides (especially hydrochloric or hydrobromic acid of which hydrochloric acid is particularly preferred) or with sulphuric or phosphoric acid as well as salts with organic acids affording pharmaceutically acceptable anions, such as for example trifluoroacetic, citric or maleic acid. In addition where the compounds of formula I are sufficiently acidic, pharmaceutically acceptable salts may be formed with an inorganic substance or organic base which affords a pharmaceutically acceptable cation. Such salts include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications Nos. 0520722, 0566226, 0602851 and 0635498. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (g) and (i) to (v) constitute further features of the present invention.

SYNTHESIS OF COMPOUNDS OF FORMULA I (a) Compounds of the formula I and salts thereof may be prepared by the reaction of a compound of the formula III:

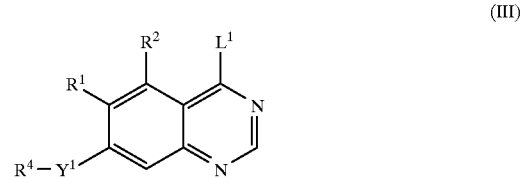

(wherein $R^1$, $R^2$, $R^4$ and $Y^1$ are as defined hereinbefore and $L^1$ is a displaceable group), with a compound of the formula IV:

(wherein Z, $R^3$ and m are as defined hereinbefore) whereby to obtain compounds of the formula I and salts thereof. A convenient displaceable group $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, isopropanol or ethyl acetate, a halogenated solvent such as methylene chloride, trichloromethane or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 20 to 80° C.

The compound of the invention may be obtained from this process in the form of the free base or alternatively it may be obtained in the form of a salt with the acid of the formula H-L¹ wherein L¹ has the meaning defined hereinbefore. When it is desired to obtain the free base from the salt, the salt may be treated with a base as defined hereinbefore using a conventional procedure.

(b) Where the group of formula IIb:

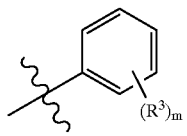

(IIb)

(wherein $R^3$ and m are as hereinbefore defined) represents a phenyl group carrying one or more hydroxy groups, a compound of the formula I and salts thereof can be prepared by the deprotection of a compound of formula V:

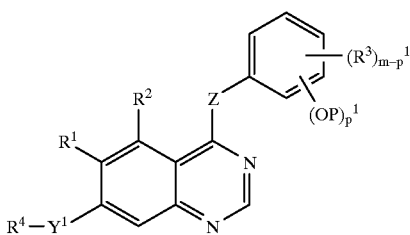

(V)

(wherein $Y^1$, m, $R^1$, $R^2$, $R^3$, $R^4$ and Z are as hereinbefore defined, P represents a phenolic hydroxy protecting group and $p^1$ is an integer from 1 to 5 equal to the number of protected hydroxy groups and such that $m-p^1$ is equal to the number of $R^3$ substituents which are not protected hydroxy). The choice of phenolic hydroxy protecting group P is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl), silyl ethers (for example, t-butyldiphenylsilyl and t-butyldimethylsilyl), esters (for example, acetate and benzoate) and carbonates (for example, methyl and benzyl). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P is acetate, the transformation may conveniently be effected by treatment of the quinazoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at or near 20° C.

(c) Production of those compounds of formula I and salts thereof wherein the substituent $Y^1$ is —O—, —S— or —NR⁹- can be achieved by the reaction, conveniently in the presence of a base as defined hereinbefore, of a compound of the formula VI:

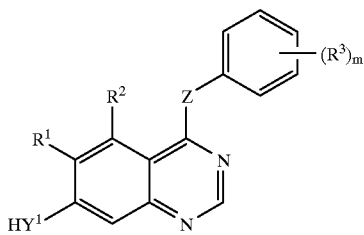

(VI)

(wherein m, $Y^1$, $R^1$, $R^2$, $R^3$ and Z are as hereinbefore defined) with a compound of formula VII:

$R^4$-$L^1$ (VII)

(wherein $R^4$ and $L^1$ are as hereinbefore defined); $L^1$ is a displaceable group for example a halogeno or sulphonyloxy group such as a bromo or methanesulphonyloxy group. The reaction is preferably effected in the presence of a base (as defined hereinbefore in process (a)) and advantageously an inert solvent or diluent (as defined hereinbefore in process (a)), advantageously at a temperature in the range, for example 10 to 150° C., conveniently at or near 50° C.

(d) Compounds of the formula I and salts thereof may be prepared by the reaction of a compound of the formula VIII:

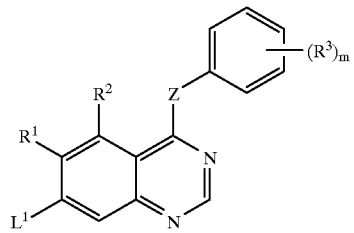

(VIII)

with a compound of the formula IX:

$R^4$-$Y^1$—H (IX)

(wherein $L^1$, $R^1$, $R^2$, $R^3$, $R^4$, Z, m and $Y^1$ are all as hereinbefore defined). The reaction may conveniently be effected in the presence of a base (as defined hereinbefore in process (a)) and advantageously in an inert solvent or diluent (as defined hereinbefore in process (a)), advantageously at a temperature in the range, for example 10 to 150° C., conveniently at or near 100° C.

(e) Compounds of the formula I and salts thereof wherein $R^4$ is $C_{1-5}$alkyl$X^2$, [wherein $X^2$ is selected from one of the following three groups:

1) $X^1$ (wherein $X^1$ is as defined hereinbefore);
2) $Y^7X^1$ (wherein $Y^7$ represents —O—, —S—, —SO₂—, —NR⁴⁷CO—, —NR⁴⁸SO₂— or —NR⁴⁹- (wherein $R^{47}$, $R^{48}$ and $R^{49}$ each independently represents hydrogen, $C_{1-3}$alkyl or $C_{1-3}$alkoxy$C_{2-3}$alkyl) and $X^1$ is as defined hereinbefore); and
3) $Y^8C_{1-5}$alkyl$Y^5X^1$ (wherein $Y^8$ represents —O—, —S—, —SO₂—, —NR⁵⁰CO—, —NR⁵¹SO₂— or —NR⁵²- (wherein $R^{50}$, $R^{51}$ and $R^{52}$ each independently represents hydrogen, $C_{1-3}$alkyl or $C_{1-3}$alkoxy$C_{2-3}$alkyl) and $Y^5$ and $X^1$ are as defined hereinbefore);]
may be prepared by reacting a compound of the formula X:

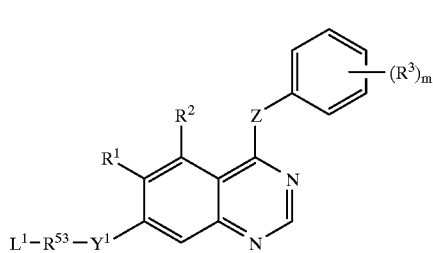

(X)

(wherein $L^1$, $Y^1$, $R^1$, $R^2$, $R^3$, Z and m are as hereinbefore defined and $R^{53}$ is $C_{1-5}$alkyl) with a compound of the formula XI:

$X^2$—H (XI)

(wherein $X^2$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

(f) The production of those compounds of the formula I and salts thereof wherein the substituent $R^1$ is represented by $NR^{10}R^{11}$, where one or both of $R^{10}$ and $R^{11}$ are $C_{1-3}$alkyl, may be effected by the reaction of compounds of formula I wherein the substituent $R^1$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature.

(g) The production of compounds of formula I and salts thereof wherein one or more of the substituents $R^1$, $R^2$ or $R^3$ is an amino group may be effected by the reduction of a corresponding compound of formula I wherein the substituent(s) at the corresponding position(s) of the quinazoline and/or phenyl ring is/are a nitro group(s). The reduction may conveniently be effected as described in process (i) hereinafter. The production of a compound of formula I and salts thereof wherein the substituent(s) at the corresponding position(s) of the quinazoline and/or phenyl ring is/are a nitro group(s) may be effected by the processes described hereinbefore and hereinafter in processes (a–e) and (i–v) using a quinazoline compound selected from the compounds of the formulae (I-XXVII) in which the substituent(s) at the corresponding position(s) of the quinazoline and/or phenyl ring is/are a nitro group(s).

SYNTHESIS OF INTERMEDIATES (i) The compounds of formula III and salts thereof, constitute a further feature of the present invention. Such compounds in which $L^1$ is halogeno may for example be prepared by halogenating a compound of the formula XII:

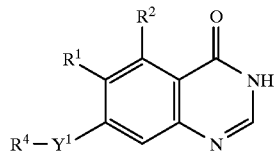

(XII)

(wherein $R^1$, $R^2$, $R^4$ and $Y^1$ are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula XII and salts thereof which constitute a further feature of the present invention may for example be prepared by reacting a compound of the formula XIII:

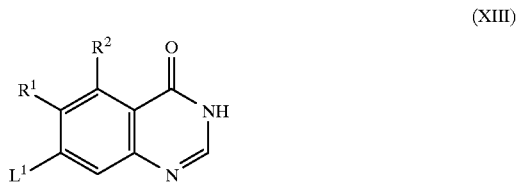

(XIII)

(wherein $R^1$, $R^2$ and $L^1$ are as hereinbefore defined) with a compound of the formula IX as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at or near 100° C.

The compounds of formula XII and salts thereof may also be prepared by cyclising a compound of the formula XIV:

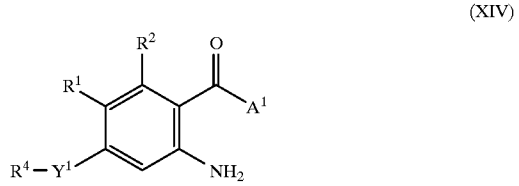

(XIV)

(wherein $R^1$, $R^2$, $R^4$ and $Y^1$ are as hereinbefore defined, and $A^1$ is an hydroxy, alkoxy (preferably $C_{1-4}$alkoxy) or amino group) whereby to form a compound of formula XII or salt thereof. The cyclisation may be effected by reacting a compound of the formula XIV, where $A^1$ is an hydroxy or alkoxy group, with formamide or an equivalent thereof effective to cause cyclisation whereby a compound of formula XII or salt thereof is obtained, such as [3-(dimethylamino)-2-azaprop-2-enylidene] dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XII may also be prepared by cyclising a compound of the formula XIV, where $A^1$ is an amino group, with formic acid or an equivalent thereof effective to cause cyclisation whereby a compound of formula XII or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and an inert solvent or diluent such as for example a halogenated solvent such as methylene chloride, trichloromethane or carbon tetrachloride, an ether such as diethylether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof, which constitute a further feature of the present invention, may for example be prepared by the reduction of the nitro group in a compound of the formula XV:

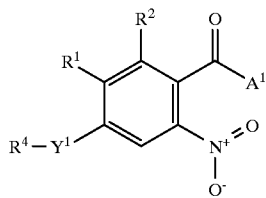

(XV)

(wherein $R^1$, $R^2$, $R^4$, $Y^1$ and $A^1$ are as hereinbefore defined) to yield a compound of formula XIV as hereinbefore defined. The reduction of the nitro group may conveniently be effected by any of the procedures known for such a transformation. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal catalyst such as palladium or platinum. A further reducing agent is, for example, an activated metal such as activated iron (produced for example by washing iron powder with a dilute solution of an acid such as hydrochloric acid). Thus, for example, the reduction may be effected by heating a mixture of the nitro compound and the activated metal in the presence of a solvent or diluent such as a mixture of water and alcohol, for example methanol or ethanol, to a temperature in the range, for example 50 to 150° C., conveniently at or near 70° C.

Compounds of the formula XV and salts thereof which constitute a further feature of the present invention, may for example be prepared by the reaction of a compound of the formula XVI:

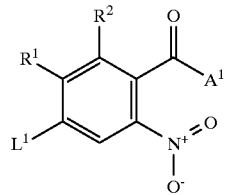

(XVI)

(wherein $R^1$, $R^2$, $L^1$ and $A^1$ are as hereinbefore defined) with a compound of the formula IX as hereinbefore defined to give a compound of the formual XV. The reaction of the compounds of formulae XVI and IX is conveniently effected under conditions as described for process (d) hereinbefore.

Compounds of formula XV and salts thereof, may for example also be prepared by the reaction of a compound of the formula XVII:

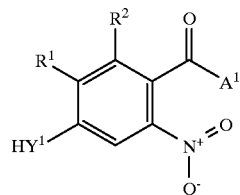

(XVII)

(wherein $R^1$, $R^2$, $Y^1$ and $A^1$ are as hereinbefore defined with the proviso that $Y^1$ is not —$CH_2$—) with a compound of the formula VII as hereinbefore defined to yield a compound of formula XV as hereinbefore defined. The reaction of the compounds of formulae XVII and VII is conveniently effected under conditions as described for process (c) hereinbefore.

The compounds of formula III and salts thereof may also be prepared for example by reacting a compound of the formula XVIII:

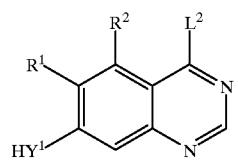

(XVIII)

(wherein $R^1$, $R^2$ and $Y^1$ are as hereinbefore defined with the proviso that $Y^1$ is not —$CH_2$— and $L^2$ represents a displaceable protecting group) with a compound of the formula VII as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (c) hereinbefore.

The compounds of formula XVIII and salts thereof as hereinbefore defined may for example be prepared by deprotecting a compound of the formula XIX:

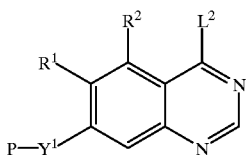

(XIX)

(wherein $R^1$, $R^2$, P, $Y^1$ and $L^2$ are as hereinbefore defined with the proviso that $Y^1$ is not —$CH_2$—). Deprotection may be effected by techniques well known in the literature, for example where P represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XII as hereinbefore defined, followed by introduction of halide to the compound of formula XII, thus obtained as hereinbefore defined, to yield a compound of formula III in which $L^1$ represents halogen.

(ii) The compounds of formula V and salts thereof, constitute a further feature of the present invention, and may for example be prepared by the reaction of a compound of formula III as hereinbefore defined with a compound of the formula XX:

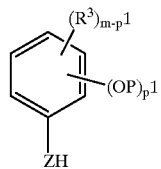

(XX)

(wherein $R^3$, m, $p^1$, P and Z are as hereinbefore defined). The reaction may for example be effected as described for process (a) hereinbefore.

The compounds of formula V and salts thereof may also be prepared by reacting a compound of formula XXI:

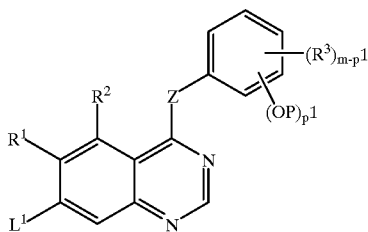

(XXI)

(wherein $R^1$, $R^2$, $L^1$, Z, $R^3$, m, $p^1$ and P are as hereinbefore defined) with a compound of formula IX as hereinbefore defined. The reaction may for example be effected as described for process (d) above.

The compounds of formula V and salts thereof may also be prepared by reacting a compound of formula XXII:

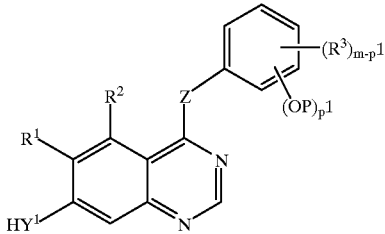

(XXII)

(wherein $R^1$, $R^2$, $R^3$, $Y^1$, Z, P, $p^1$ and m are as hereinbefore defined with the proviso that $Y^1$ is not —$CH_2$—) with a compound of the formula VII as hereinbefore defined. The reaction may for example be effected as described for process (c) hereinbefore.

The compounds of formula XXI and salts thereof may for example be prepared by reaction of a compound of formula XXIII:

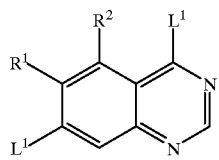

(XXIII)

(wherein $R^1$, $R^2$, and $L^1$ are as hereinbefore defined, and $L^1$ in the 4- and 7-positions may be the same or different) with a compound of the formula XX as hereinbefore defined. The reaction may be effected for example by a process as described in (a) above.

Compounds of the formula XXII and salts thereof may be made by reacting compounds of the formulae XIX and XX as hereinbefore defined, under conditions described in (a) hereinbefore, to give a compound of formula XXIV:

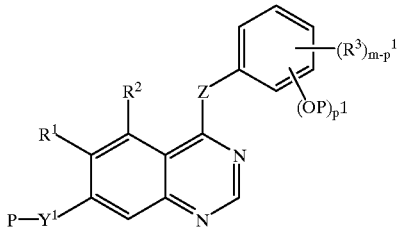

(XXIV)

(wherein $R^1$, $R^2$, $R^3$, P, Z, $Y^1$, $p^1$ and m are as hereinbefore defined with the proviso that $Y^1$ is not —$CH_2$—) and then deprotecting the compound of formula XXIV for example as described in (i) above.

(iii) Compounds of the formula VI and salts thereof, as hereinbefore defined, may be made by deprotecting the compound of formula XXV:

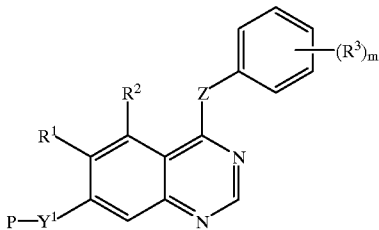

(XXV)

(wherein $R^1$, $R^2$, $R^3$, P, Z, $Y^1$ and m are as hereinbefore defined) by a process for example as described in (i) above.

Compounds of the formula XXV and salts thereof may be made by reacting compounds of the formulae XIX and IV as hereinbefore defined, under the conditions described in (a) hereinbefore, to give a compound of the formula XXV or salt thereof.

(iv) Compounds of the formula VIII and salts thereof as hereinbefore defined may be made by reacting compounds of the formulae XXIII and IV as hereinbefore defined, the reaction may be effected by a process as described in (a) above.

(v) Compounds of the formula X as defined hereinbefore and salts thereof may for example be made by the reaction of a compound of formula VI as defined hereinbefore with a compound of the formula XXVI:

$$L^1-R^{53}-L^1 \qquad (XXVI)$$

(wherein $L^1$ and $R^{53}$ are as hereinbefore defined) to give a compound of the formula X. The reaction may be effected for example by a process as described in (c) above.

Compounds of the formula X and salts thereof may also be made for example by deprotecting a compound of the formula XXVII:

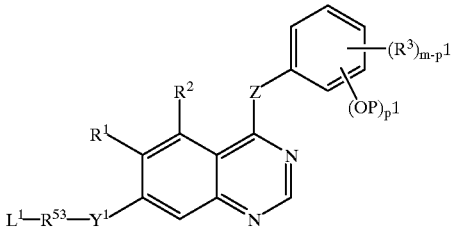

(XXVII)

(wherein $L^1$, $R^{53}$, $Y^1$, $R^1$, $R^2$, $R^3$, P, m and $p^1$ are as defined hereinbefore) by a process for example as described in (b) above.

Compounds of the formula XXVII and salts thereof may be made for example by reacting compounds of the formulae XXII and XXVI as defined hereinbefore, under the conditions described in (c) above.

When a pharmaceutically acceptable salt of a compound of the formula I is required, it may be obtained, for example, by reaction of said compound with, for example, an acid using a conventional procedure.

Many of the intermediates defined herein are novel, for example, those of the formulae III, V, XII, XIV and XV and these are provided as a further feature of the invention.

Intermediates of the formulae VIII, X, XXI, XXII, XXIV, XXV and XXVII are also provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example Spodoptera frugiperda 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM NaCl, 2.7 mM KCl) then resuspended in ice cold HNTG/PMSF (20 mM Hepes pH7.5, 150 mM NaCl, 10% v/v glycerol, 1% v/v Triton X100, 1.5 mM $MgCl_2$, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM $Na_3VO_4$, 0.1% v/v Triton X100, 0.2 mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 μl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 μl of diluted compound was transferred to wells in the washed assay plates. "Total" control wells contained 10% DMSO instead of compound. Twenty five microliters of 40 mM $MnCl_2$ containing 8 μM adenosine-5'-triphosphate (ATP) was added to all test wells except "blank" control wells which contained $MnCl_2$ without ATP. To start the reactions 50 μl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 μg/ml heparin+1 μg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 μCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 μg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I, or a pharmaceutically acceptable salt thereof, as defined hereinbefore in association with a pharmaceutically acceptable excipient or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have now found that compounds of the present invention inhibit VEGF receptor tyrosine kinase activity and are therefore of interest for their antiangiogenic effects and/or their ability to cause a reduction in vascular permeability.

Thus according to this aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example EGF, FGFs, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisatine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus;

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet;

(vii) intermediates were not generally fully characterised and purity was assessed by thin layer chromatography (TLC), high-performance liquid chromatography (HPLC), infra-red (IR) or NMR analysis;

(viii) the following abbreviations have been used:

DMF N,N-dimethylformamide
DMSO dimethylsulphoxide
NMP 1-methyl-2-pyrrolidinone
THF tetrahydrofuran
TFA trifluoroacetic acid.]

Example 1

To a solution of 4-(3-acetoxy-4-methylanilino)-6-methoxy-7-(4-pyridylmethoxy)quinazoline (93 mg, 0.2 mmol) in a mixture of methanol (6 ml) and methylene chloride (3 ml) was added at ambient temperature a 2M aqueous sodium hydroxide solution (0.3 ml, 0.6 mmol). The mixture was stirred for 10 minutes at ambient temperature, the solvents were partially evaporated, water was added to the residue and the solution was acidified with 0.1M hydrochloric acid to pH6. The precipitate was filtered off, washed with water and dried under vacuum to give 4-(3-hydroxy-4-methylanilino)-6-methoxy-7-(4-pyridylmethoxy)quinazoline hydrochloride (67 mg, 87%).

m.p. 249–251° C.

$^1$H NMR Spectrum: (DMSOd$_6$) 2.13 (s, 3H); 4.01 (s, 3H); 5.40 (s, 2H); 7.05 (br s, 2H); 7.24 (s, 1H); 7.34 (s, 1H); 7.51 (d, 2H); 7.92 (s, 1H); 8.44 (s, 1H); 8.63 (d, 2H); 9.34 (s, 1H); 9.47 (br s, 1H)

MS-ESI: 389 [MH]$^+$

Elemental analysis: Found C 61.4 H 5.3 N 12.8
C$_{22}$H$_{20}$N$_4$O$_3$ 1.8H$_2$O, 0.2HCl Requires C 61.7 H 5.6 N 13.1%

The starting material was prepared as follows:

A mixture of 2-amino-4-benzyloxy-5-methoxybenzamide (10 g, 0.04 mol), (J. Med. Chem. 1977, vol 20, 146–149), and Gold's reagent (7.4g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The mixture was evaporated, water was added to the residue, the solid was filtered off, washed with water and dried (MgSO$_4$). Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin-4-one (2.82 g, 0.01 mol), thionyl chloride (40 ml) and DMF (0.28 ml) was stirred and heated at reflux for 1 hour. The mixture was evaporated, the residue was taken up in toluene and evaporated to dryness to give 7-benzyloxy-4-chloro-6-methoxyquinazoline hydrochloride (3.45 g).

A mixture of 7-benzyloxy-4-chloro-6-methoxyquinazoline hydrochloride (2.18 g, 6.47 mmol), 3-acetoxy-4-methylaniline (1.32 g, 8 mmol) and isopropanol (50 ml) was stirred and heated at reflux for 1 hour. The mixture was cooled to ambient temperature. The precipitate was filtered off, washed with isopropanol and ether to give 4-(3-acetoxy-4-methylanilino)-7-benzyloxy-6-methoxyquinazoline hydrochloride (2.69 g, 89%).

A mixture of 4-(3-acetoxy-4-methylanilino)-7-benzyloxy-6-methoxyquinazoline hydrochloride (2.68 g, 5.75 mmol), 10% palladium-on-charcoal catalyst (0.27 g) in methanol (50 ml), DMF (12 ml) and trichloromethane (50 ml) was stirred at ambient temperature under an atmosphere of hydrogen (1.5 atmospheres) for 30 minutes. The catalyst was filtered off and the filtrate evaporated. The residual solid was triturated in ether, filtered off and dried under vacuum at 50° C. to give 4-(3-acetoxy-4-methylanilino)-7-hydroxy-6-methoxyquinazoline hydrochloride (2.1 g, 100%).

To a solution of 4-(3-acetoxy-4-methylanilino)-7-hydroxy-6-methoxyquinazoline hydrochloride (375 mg, 1 mmol) in DMF (16 ml) were added at ambient temperature potassium carbonate (415 mg, 3 mmol) and 4-(bromomethyl)pyridine hydrobromide (J. Org. Chem. 1958, 23, 575, 278 mg, 1.1 mmol). The reaction mixture was heated at 60° C. for 2 hours. The mixture was evaporated and the residue was partitioned between ethyl acetate and water. The organic layer was washed with a saturated aqueous sodium chloride solution, dried (MgSO$_4$) and evaporated. The residue was purified by column flash chromatography, eluting with methylene chloride/methanol (95/5) to give 4-(3-acetoxy-4-methylanilino)-6-methoxy-7-(4-pyridylmethoxy)quinazoline (93 mg, 22%).

m.p. 201–202° C.

$^1$H NMR Spectrum: (DMSOd$_6$) 2.12 (s, 3H); 2.34 (s, 3H); 4.02 (s, 3H); 5.40 (s, 2H); 7.27 (s, 1H); 7.30 (d, 1H); 7.51 (d, 2H); 7.62 (s, 1H); 7.65 (d, 1H); 7.91 (s, 1H); 8.47 (s, 1H); 8.63 (d, 2H); 9.53 (s, 1H)

MS-ESI: 453 [MNa]$^+$, 431 [MH]$^+$

Elemental analysis: Found C 65.4 H 5.5 N 12.7
C$_{24}$H$_{22}$N$_4$O$_4$ 0.6H$_2$O Requires C 65.3 H 5.3 N 12.7%

3-Acetoxy-4-methylaniline used as a starting material was prepared as follows:

To a mixture of 2-methyl-5-nitrophenol (2.5 g, 16.3 mmol) and 1M aqueous sodium hydroxide (24.5 ml) was added at ambient temperature acetic anhydride (1.9 ml, 20.3 mmol). The mixture was stirred for 40 minutes, the solid was filtered off and the filtrate extracted with ethyl acetate. The organic layers were combined, washed with an aqueous saturated sodium chloride solution, dried (MgSO$_4$) and evaporated to yield 2-acetoxy-4-nitrotoluene (3.1 g, 100%). A mixture of this material (3.1 g, 15.9 mmol) and 10% palladium-on-charcoal catalyst (0.12 g) in ethyl acetate (50 ml) was stirred at ambient temperature under an atmosphere of hydrogen for 2 hours. The catalyst was filtered off and the filtrate evaporated to give 3-acetoxy-4-methylaniline (2.45 g, 94%).

Example 2

Using an analogous procedure to that described for the starting material in Example 1, 4-(3-acetoxy-4-methylanilino)-7-hydroxy-6-methoxyquinazoline hydrochloride (750 mg) was reacted with 3-(bromomethyl)pyridine hydrobromide (Can. J. Chem. 1978, 56, 3068) (378 mg) to give 4-(3-acetoxy-4-methylanilino)-6-methoxy-7-(3-pyridylmethoxy)quinazoline (293 mg, 34%).

m.p. 113–115° C.

$^1$H NMR Spectrum: (DMSOd$_6$) 2.09 (s, 3H); 2.30 (s, 3H); 3.94 (s, 3H); 5.32 (s, 2H); 7.27 (d, 1H); 7.32 (s, 1H); 7.43–7.46 (m, 1H); 7.58 (s, 1H); 7.59–7.63 (m, 1H); 7.85 (s, 1H); 7.89–7.92 (m, 1H); 8.45 (s, 1H); 8.57 (dd, 1H); 8.71 (d, 1H); 9.48 (s, 1H)

MS-ESI: 453 [MNa]$^+$, 431 [MH]$^+$

Elemental analysis: Found C 64.4 H 5.7 N 11.7
C$_{24}$H$_{22}$N$_4$O$_4$ 0.85H$_2$O Requires C 64.7 H 5.4 N 12.6%

Example 3

The compound synthesised in Example 2 was further subjected to basic cleavage of the acetoxy protecting group using an analogous procedure to that described in Example 1 to give 4-(3-hydroxy-4-methylanilino)-6-methoxy-7-(3-pyridylmethoxy)quinazoline (215 mg, 83%).

m.p. 258–259° C.

$^1$H NMR Spectrum: (DMSOd$_6$) 2.12 (s, 3H); 3.94 (s, 3H); 5.34 (s, 2H); 7.05 (s, 2H); 7.32 (s, 1H); 7.35 (s, 1H); 7.46–7.49 (m, 1H); 7.88 (s, 1H); 7.93–7.95 (m, 1H); 8.43 (s, 1H); 8.60 (dd, 1H); 8.74 (d, 1H); 9.33 (s, 1H); 9.35 (s, 1H)

MS-ESI: 411 [MNa]$^+$, 389 [MH]$^+$

Elemental analysis: Found C 59.2 H 5.5 N 12.6
C$_{22}$H$_{20}$N$_4$O$_3$ 3H$_2$O 0.07HCl Requires C 59.4 H 5.9 N 12.6%

Example 4

4-(3-Acetoxy-4-methylanilino)-6-methoxy-7-(2-pyridylmethoxy)quinazoline (170 mg, 0.39 mmol) was subjected to basic cleavage of the acetoxy protecting group using an analogous procedure to that described in Example 1 to give 4-(3-hydroxy-4-methylanilino)-6-methoxy-7-(2-pyridylmethoxy)quinazoline hydrochloride (58 mg, 38%).

m.p. 236–238° C.

$^1$H NMR Spectrum: (DMSOd$_6$) 2.30 (s, 3H); 3.97 (s, 3H); 5.34 (s, 2H); 7.02 (s, 2H); 7.23 (s, 1H); 7.33 (s, 1H); 7.36–7.39 (m, 1H); 7.56 (d, 1H); 7.84–7.88 (m, 1H); 7.87 (s, 1H); 8.39 (s, 1H); 8.91 (d, 1H); 9.32 (s, 2H)

MS-ESI: 389 [MH]$^+$

Elemental analysis: Found C 55.8 H 5.5 N 11.8 C$_{22}$H$_{20}$N$_4$O$_3$ 3H$_2$O 0.75HCl Requires C 56.2 H 5.7 N 11.9%

The starting material was prepared as follows:

Using an analogous procedure to that described for the starting material in Example 1, 4-(3-acetoxy-4-methylanilino)-7-hydroxy-6-methoxyquinazoline hydrochloride (376 mg) was reacted with 2-(chloromethyl)pyridine hydrochloride (328 mg) to give 4-(3-acetoxy-4-methylanilino)-6-methoxy-7-(2-pyridylmethoxy)quinazoline (170 mg, 40%).

$^1$H NMR Spectrum: (DMSOd$_6$) 2.12 (s, 3H); 2.34 (s, 3H); 4.00 (s, 3H); 5.37 (s, 2H); 7.29 (s, 1H); 7.31 (s, 1H); 7.39–7.42 (m, 1H); 7.58–7.66 (m, 3H); 7.87–7.90 (m, 1H); 7.91 (s, 1H); 8.47 (s, 1H); 8.64 (d, 1H); 9.52 (s, 1H)

Example 5

4-(3-Acetoxy-4-methylanilino)-6-methoxy-7-(pyrimidin-4-ylmethoxy)quinazoline (496 mg, 1.15 mmol) was subjected to basic cleavage of the acetoxy protecting group using an analogous procedure to that described in Example 1 to give 4-(3-hydroxy-4-methylanilino)-6-methoxy-7-(pyrimidin-4-ylmethoxy)quinazoline (278 mg, 62%).

m.p. 290–291° C.

$^1$H NMR Spectrum: (DMSOd$_6$) 2.13 (s, 3H); 4.02 (s, 3H); 5.43 (s, 2H); 7.05 (s, 2H); 7.24 (s, 1H); 7.35 (s, 1H); 7.67 (d, 1H); 7.92 (s, 1H); 8.41 (s, 1H); 8.89 (d, 1H); 9.24 (s, 1H); 9.36 (s, 1H); 9.38 (s, 1H)

MS-ESI: 390 [MH]$^+$

Elemental analysis: Found C 58.8 H 5.4 N 16.3 C$_{21}$H$_{19}$N$_5$O$_3$ 2.2H$_2$O Requires C 58.8 H 5.5 N 16.3%

The starting material was prepared as follows:

Using an analogous procedure to that described for the starting material in Example 1, 4-(3-acetoxy-4-methylanilino)-7-hydroxy-6-methoxyquinazoline hydrochloride (560 mg) was reacted in the presence of catalytic potassium iodide with 4-(chloromethyl)pyrimidine (375 mg) to give 4-(3-acetoxy-4-methylanilino)-6-methoxy-7-(pyrimidin-4-ylmethoxy)quinazoline (496 mg, 74%).

$^1$H NMR Spectrum: (DMSOd$_6$) 2.13 (s, 3H); 2.35 (s, 3H); 4.03 (s, 3H); 5.44 (s, 2H); 7.27 (s, 1H); 7.31 (d, 1H); 7.62–7.68 (m, 3H); 7.93 (s, 1H); 8.47 (s, 1H); 8.89 (d, 1H); 9.24 (d, 1H); 9.54 (s, 1H)

4-(Chloromethyl)pyrimidine was synthesised as follows:

A mixture of 4-methylpyrimidine (2 g, 21.2 mmol), N-chlorosuccinimide (4.26 g, 31.9 mmol) and dibenzoylperoxide (500 mg) in carbon tetrachloride (100 ml) was heated at 80° C. for 2 hours. After cooling, the mixture was filtered and the filtrate was evaporated. The resulting oil was purified by flash chromatography using methylene chloride as eluant to give 4-(chloromethyl)pyrimidine as an orange oil (1 g, 37%).

Example 6

A solution of 4-(3-acetoxy-4-methylanilino)-7-hydroxy-6-methoxyquinazoline hydrochloride (400 mg, 1.06 mmol), (prepared as described for the starting material in Example 1), 2-chloromethyl-1-methylimidazole hydrochloride (354 mg, 2.12 mmol), and potassium carbonate (585 mg) in DMF (15 ml) was heated at 60° C. for 15 hours. After cooling to ambient temperature the reaction mixture was partitioned between ethyl acetate and water. The organic layer was washed with brine, dried (MgSO$_4$) and evaporated. The residue was diluted with methanol (20 ml) and 2M sodium hydroxide (1 ml) was added. After stirring for 1 hour, the reaction mixture was diluted with water (20 ml) and 2M hydrochloric acid (3 ml) was added. The resulting solid was filtered off, washed with water and dried under vacuum to give 4-(3-hydroxy-4-methylanilino)-6-methoxy-7-(1-methylimidazol-2-ylmethoxy)quinazoline hydrochloride (150 mg, 29%).

m.p. 257–260° C.

$^1$H NMR Spectrum: (DMSOd$_6$) 2.17 (s, 3H); 3.95 (s, 3H); 4.03 (s, 3H); 5.68 (s, 2H); 7.02 (dd, 1H); 7.16 (s, 2H); 7.64 (s, 1H); 7.72 (s, 1H); 7.80 (s, 1H); 8.42 (s, 1H); 8.8 (s, 1H); 9.7 (s, 1H); 11.38 (s, 1H)

MS-ESI: 392 [MH]$^+$

Elemental analysis: Found C 51.7 H 5.5 N 14.2 C$_{21}$H$_{21}$N$_5$O$_3$ 1.65H$_2$O 1.9HCl Requires C 51.4 H 5.4 N 14.3%

Example 7

A solution of 4-(3-acetoxy-4-methylanilino)-7-hydroxy-6-methoxyquinazoline hydrochloride (400 mg, 1.06 mmol), (prepared as described for the starting material in Example 1), 4-chloromethyl-2-methylthiazole hydrochloride (390 mg, 2.12 mmol), potassium carbonate (438 mg) and potassium iodide (40 mg) in DMF (15 ml) was heated at 60° C. for 15 hours. After cooling to ambient temperature the reaction mixture was partitioned between ethyl acetate and water. The organic layer was washed with brine, dried (MgSO$_4$) and evaporated. The residue was diluted with methanol (10 ml) and 2M sodium hydroxide (2 ml) was added. After stirring for 1 hour, the reaction mixture was diluted with water (20 ml) and 2M hydrochloric acid (3 ml) was added. The resulting solid was filtered off, washed with water and dried under vacuum to give 4-(3-hydroxy-4-methylanilino)-6-methoxy-7-(2-methylthiazol-4-ylmethoxy) quinazoline hydrochloride (300 mg, 59%).

m.p. 243–245° C.

$^1$H NMR Spectrum: (DMSOd$_6$) 2.17 (s, 3H); 2.7 (s, 3H); 4.0 (s, 3H); 5.35 (s, 2H); 7.0 (dd, 1H); 7.12 (d, 1H); 7.16 (d, 1H); 7.58 (s, 1H); 7.75 (s, 1H); 8.3 (s, 1H); 8.8 (s, 1H); 9.5–9.8 (br s, 1H); 11.3 (s, 1H)

MS-ESI: 409 [MH]$^+$

Elemental analysis: Found C 51.9 H 5.0 N 11.6 S 6.8 C$_{21}$H$_{20}$N$_4$O$_3$S 1H$_2$O 1.7HCl Requires C 51.6 H 4.9 N 11.5 S 6.6%

Example 8

To a solution of 4-(3-acetoxy-4-methylanilino)-6-methoxy-7-(3-thienylmethoxy)quinazoline (200 mg, 0.45 mmol) in methylene chloride/methanol (1/1) (20 ml) was added, a 2M aqueous sodium hydroxide solution (0.67 ml, 1.35 mmol). The mixture was stirred for 35 minutes at ambient temperature, the solvents were evaporated, water was added to the residue and the solution was extracted with ethyl acetate. The organic layer was washed with water, brine, then dried (MgSO$_4$) and evaporated to give a white solid. This solid was then dissolved into a saturated solution of hydrochloric acid in methanol (10 ml) and stirred for 10 minutes. The solid product was filtered and dried under a vacuum, to give 4-(3-hydroxy-4-methylanilino)-6-methoxy-7-(3-thienylmethoxy)quinazoline hydrochloride (127 mg, 66%).

m.p. 246–248° C.

$^1$H NMR Spectrum: (DMSOd$_6$) 2.15 (s, 3H); 3.98 (s, 3H); 5.32 (s, 2H); 6.98 (dd, 1H); 7.10 (s, 1H); 7.14 (d, 1H); 7.25 (d, 1H); 7.40 (s, 1H); 7.61 (dd, 1H); 7.70 (d, 1H); 8.12 (s, 1H); 8.74 (s, 1H); 9.60 (s, 1H)

MS-ESI: 394 [MH]$^+$

Elemental analysis: Found C 58.3 H 4.8 N 9.4 S 7.3 Cl 7.5 C$_{21}$H$_{19}$N$_3$O$_3$S 0.2H$_2$O 0.95HCl Requires C 58.4 H 4.8 N 9.7 S 7.4 Cl 7.8%

The starting material was prepared as follows:

Using an analogous procedure to that described for the starting material in Example 1,4-(3-acetoxy-4-methylanilino)-7-hydroxy-6-methoxyquinazoline hydrochloride (400 mg) was reacted in the presence of catalytic potassium iodide with 3-chloromethylthiophene (Journal of the Chemical Society 1958, 4202) (168 mg) to give 4-(3-acetoxy-4-methylanilino)-6-methoxy-7-(3-thienylmethoxy)quinazoline (210 mg, 46%).

m.p. 201–203° C.

$^1$H NMR Spectrum: (DMSOd$_6$) 2.11 (s, 3H); 2.32 (s, 3H); 3.95 (s, 3H); 5.27 (s, 2H); 7.23 (dd, 1H); 7.28 (d, 1H); 7.32 (s, 1H); 7.58–7.66 (m, 4H); 7.85 (s, 1H); 8.46 (s, 1H); 9.49 (s, 1H)

MS-ESI: 436 [MH]$^+$

Elemental analysis: Found C 63.0 H 5.2 N 9.1 S 7.3 C$_{23}$H$_{21}$N$_3$O$_4$S 0.3H$_2$O Requires C 62.7 H 5.0 N 9.5 S 7.3%

Example 9

7-(2-Acetamidothiazol-4-ylmethoxy)-4-(3-acetoxy-4-methylanilino)-6-methoxyquinazoline (220 mg, 0.44 mmol) was subjected to basic cleavage of the acetoxy protecting group using an analogous procedure to that described in Example 8 to give, 7-(2-acetamidothiazol-4-ylmethoxy)4-(3-hydroxy-4-methylanilino)-6-methoxyquinazoline hydrochloride (41 mg, 19%).

m.p. 202–204° C.

$^1$H NMR Spectrum: (DMSOd$_6$) 2.16 (s, 3H); 2.17 (s, 3H); 4.01 (s, 3H); 5.31 (s, 2H); 6.98 (dd, 1H); 7.10 (d, 1H); 7.17 (d, 1H); 7.34 (s, 1H); 7.47 (s, 1H); 8.22 (s, 1H); 8.80 (s, 1H); 9.68 (br s, 1H)

MS-ESI: 452 [MH]$^+$

Elemental analysis: Found C 47.1 H 4.7 N 12.5 S 5.8 Cl 12.2 C$_{22}$H$_{21}$N$_5$O$_4$S 2H$_2$O 2HCl Requires C 47.2 H 4.9 N 12.5 S 5.7 Cl 12.7%

The starting material was prepared as follows:

Using an analogous procedure to that described for the starting material in Example 1,4-(3-acetoxy-4-methylanilino)-7-hydroxy-6-methoxyquinazoline hydrochloride (400 mg) was reacted in the presence of catalytic potassium iodide with 2-acetamido-4-chloromethylthiazole (252 mg) to give 7-(2-acetamidothiazol-4-ylmethoxy)-4-(3-acetoxy-4-methylanilino)-6-methoxyquinazoline (220 mg, 42%).

$^1$H NMR Spectrum: (DMSOd$_6$) 2.13 (s, 3H); 2.15 (s, 3H); 2.35 (s, 3H); 3.97 (s, 3H); 5.24 (s, 2H); 7.24–7.31 (m, 2H); 7.37 (s, 1H); 7.63–7.66 (m, 2H); 7.87 (s, 1H); 8.48 (s, 1H); 9.50 (s, 1H)

MS-ESI: 494 [MH]$^+$

Example 10

4-(3-Acetoxy-4-methylanilino)-7-(3,5-dimethylisoxazol-4-ylmethoxy)-6-methoxyquinazoline (342 mg, 0.76 mmol) was subjected to basic cleavage of the acetoxy protecting group using an analogous procedure to that described in Example 8 to give 4-(3-hydroxy-4-methylanilino)-7-(3,5-dimethylisoxazol-4-ylmethoxy)-6-methoxyquinazoline hydrochloride (209 mg, 62%).

m.p. 252–254° C.

$^1$H NMR Spectrum: (DMSOd$_6$) 2.20 (s, 3H); 2.29 (s, 3H); 2.52 (s, 3H); 4.03 (s, 3H); 5.23 (s, 2H); 7.03 (dd, 1H); 7.15 (d, 1H); 7.19 (d, 1H); 7.44 (s, 1H); 8.22 (s, 1H); 8.82 (s, 1H); 9.67 (s, 1H)

MS-ESI: 407 [MH]$^+$

Elemental analysis: Found C 59.1 H 5.4 N 12.6 Cl 8.0 C$_{22}$H$_{22}$N$_4$O$_4$ 0.25H$_2$O 1HCl Requires C 59.1 H 5.3 N 12.5 Cl 7.9%

The starting material was prepared as follows:

Using an analogous procedure to that described for the starting material in Example 1,4-(3-acetoxy-4-methylanilino)-7-hydroxy-6-methoxyquinazoline hydrochloride (400 mg) was reacted in the presence of potassium iodide (16 mg) with 4-chloromethyl-3,5-dimethylisoxazole (177 mg) to give 4-(3-acetoxy-4-methylanilino)-7-(3,5-dimethylisoxazol-4-ylmethoxy)-6-methoxyquinazoline (342 mg, 72%).

$^1$H NMR Spectrum: (DMSOd$_6$) 2.18 (s, 3H); 2.33 (s, 3H); 2.35 (s, 3H); 2.46 (s, 3H); 3.98 (s, 3H); 4.98 (s, 2H); 7.00 (s, 1H); 7.15 (s, 1H); 7.22–7.25 (m, 1H); 7.32 (s, 1H); 7.43 (dd, 1H); 7.51 (s, 1H); 8.66 (s, 1H)

Example 11

A solution of 4-(3-acetoxy-4-methylanilino)-7-hydroxy-6-methoxyquinazoline hydrochloride (400 mg, 1.06 mmol), (prepared as described for the starting material in Example 1), 4-(3-chloropropyl)pyridyl hydrochloride 410 mg, 2.1 mmol), potassium carbonate (438 mg) and potassium iodide (40 mg) in DMF (15 ml) was heated at 60° C. for 15 hours. After cooling to ambient temperature the reaction mixture was partitioned between ethyl acetate and water. The organic layer was washed with brine, dried (MgSO$_4$) and evaporated. The residue was diluted with methanol (20 ml) and 2M sodium hydroxide (2 ml) was added. After stirring for 1 hour, the reaction mixture was diluted with water (20 ml) and concentrated hydrochloric acid (1 ml) was added. The resulting solid was filtered off and was purified by preparative C18 HPLC using a gradient of methanol/water (0% to 80%) as eluant. After evaporation of the methanol, concentrated hydrochloric acid (0.3 ml) was added and the solution was evaporated to dryness. After trituration with acetone, the solid was filtered off and dried under vacuum to give 4-(3-hydroxy-4-methylanilino)-6-methoxy-7-(4-pyridylpropoxy)quinazoline hydrochloride (305 mg, 59%).

m.p. 278–282° C.

$^1$H NMR Spectrum: (DMSO-d$_6$) 2.15 (s, 3H); 2.3 (m, 2H); 3.1 (m, 2H); 3.96 (s, 3H); 4.24 (t, 2H); 6.98 (dd, 1H); 7.15 (m,2H); 7.44 (s, 1H); 7.96 (d, 2H); 8.31 (s, 1H); 8.77 (s, 1H); 8.81 (d, 2H); 9.7 (br s, 1H); 11.34 (s, 1H)

MS-ESI: 417 [MH]+

Elemental analysis: Found C 57.3 H 5.4 N 11.0 $C_{24}H_{24}N_4O_3$ $0.7H_2O$ 1.95HCl Requires C 57.6 H 5.5 N 11.2%

The starting material was prepared as follows:

Thionyl chloride (1.6 ml) was added to a solution of 4-pyridine propanol (2 g, 14.5 mmol) in trichloromethane (20 ml) cooled at 0° C. After stirring for 1 hour at ambient temperature followed by 1 hour at 60° C., the solvent was evaporated and the residue was triturated with ether to give 4-(3-chloropropyl)pyridyl hydrochloride as a white solid.

$^1$H NMR Spectrum: (DMSOd$_6$) 2.15 (m, 2H); 3.02 (t, 2H); 3.69 (t, 2H); 7.96 (d, 2H); 8.84 (d, 2H)

Example 12

A solution of 4-(2-fluoro-5-methoxycarbonyloxy-4-methylanilino)-7-hydroxy-6-methoxyquinazoline hydrochloride (410 mg, 1.00 mmol), 4-(3-chloropropyl)pyridyl hydrochloride (480 mg, 2.5 mmol), potassium carbonate (480 mg) and potassium iodide (40 mg) in DMF (15 ml) was heated at 60° C. for 15 hours. After cooling to ambient temperature the reaction mixture was partitioned between ethyl acetate and water. The organic layer was washed with brine, dried (MgSO$_4$) and evaporated. The residue was diluted with methanol (10 ml) and 2M sodium hydroxide (2 ml) was added. After stirring for 1 hour, the reaction mixture was diluted with water (20 ml) and concentrated hydrochloric acid (0.5 ml) was added. The resulting solid was filtered off and was purified by preparative C18 HPLC using a gradient of methanol/water (0% to 80%) as eluant. After evaporation of the methanol, concentrated hydrochloric acid (0.3 ml) was added and the solution was evaporated to dryness. After trituration with acetone, the solid was filtered off and dried under vacuum to give 4-(2-fluoro-5-hydroxy-4-methylanilino)-6-methoxy-7-(4-pyridylpropoxy)quinazoline hydrochloride (243 mg, 48%).

m.p. 246–248° C.

$^1$H NMR Spectrum: (DMSOd$_6$) 2.16 (s, 3H); 2.30 (m, 2H); 3.09 (t, 2H); 3.95 (s, 3H); 4.26 (t, 2H); 6.90 (d, 1H); 7.11 (d, 1H); 7.41 (s, 1H); 7.94 (d, 2H); 8.3 (s, 1H); 8.77 (s, 1H); 8.80 (d, 2H); 9.7 (br s, 1H); 11.46 (s, 1H)

MS-ESI: 435 [MH]+

Elemental analysis: Found C 55.3 H 5.3 N 10.2 Cl 13.0 $C_{24}H_{23}N_4O_3F$ $0.9H_2O$ 1.95HCl Requires C 55.3 H 5.2 N 10.7 Cl 13.3%

The starting material was prepared as follows:

A solution of (4-fluoro-2-methyl-5-nitrophenyl) methyl carbonate (3 g, 13 mmol), (prepared as described in EP 0307777 A2), in ethanol (60 ml) containing platinum(IV) oxide (300 mg) was stirred under hydrogen at 0.3 atmosphere for 1 hour. After filtration and evaporation of the solvent, 2-fluoro-5-methoxycarbonyloxy-4-methylaniline was isolated as a solid (2.6 g, 100%).

$^1$H NMR Spectrum: (CDCl$_3$) 2.07 (s, 3H); 3.87 (s, 3H); 6.52 (d, 1H); 6.80 (d, 1H)

A solution of 7-benzyloxy-4-chloro-6-methoxyquinazoline hydrochloride (800 mg, 2.4 mmol), (prepared as described for the starting material in Example 1), and 2-fluoro-5-methoxycarbonyloxy-4-methylaniline (570 mg, 2.89 mmol) in isopropanol (20 ml) was refluxed for 2 hours. After cooling to ambient temperature, the solid was filtered, washed with isopropanol and dried under vacuum to give 7-benzyloxy-4-(2-fluoro-5-methoxycarbonyloxy-4-methylanilino)-6-methoxyquinazoline hydrochloride (1.0 g, 87%)

$^1$H NMR Spectrum: (DMSOd$_6$; CF$_3$COOD) 2.2 (s, 3H); 3.85 (s, 3H); 4.0 (s, 3H); 5.37 (s, 2H); 7.3–7.55 (m, 8H); 8.13 (s, 1H); 8.86 (s, 1H)

MS-ESI: 464 [MH]+

A solution of 7-benzyloxy-4-(2-fluoro-5-methoxycarbonyloxy-4-methylanilino)-6-methoxyquinazoline hydrochloride (700 mg, 1.45 mmol) in DMF (10 ml), methanol (10 ml) and trichloromethane (10 ml) containing 10% palladium-on-charcoal (100 mg) was stirred under an atmosphere of hydrogen for 1 hour. After filtration and evaporation of the solvent, the residue was triturated with ether, filtered and dried under vacuum to give 4-(2-fluoro-5-methoxycarbonyloxy-4-methylanilino)-7-hydroxy-6-methoxyquinazoline hydrochloride (570 mg, 98%).

$^1$H NMR Spectrum: (DMSOd$_6$) 2.23 (s, 3H); 3.87 (s, 3H); 4.01 (s, 3H); 7.37 (s, 1H); 7.45 (d, 1H); 7.5 (d, 1H); 8.20 (s, 1H); 8.77 (s, 1H); 11.35 (s, 1H); 11.79 (s, 1H)

MS-ESI: 374 [MH]+

Example 13

A stirred solution of 4-chloro-6-methoxy-7-(4-pyridylmethoxy)quinazoline (35 mg, 0.1 mmol) and 2-fluoro-5-hydroxy-4-methylaniline (15 mg, 0.1 mmol) in a mixture of ethereal hydrogen chloride (2 ml) and isopropanol (5 ml) was heated at reflux for 4 hours. The precipitated product was collected by filtration, washed with acetone and dried under vacuum to give 4-(2-fluoro-5-hydroxy-4-methylanilino)-6-methoxy-7-(4-pyridylmethoxy)quinazoline hydrochloride (23 mg, 47%).

m.p. 257–260° C.

$^1$H NMR Spectrum: (DMSOd$_6$) 2.15 (s, 3H); 4.08 (s, 3H); 5.60 (s, 2H); 6.90 (d, 1H); 7.07 (d, 1H); 7.47 (s, 1H); 7.93 (br d, 2H); 8.74 (s, 1H); 8.89 (br d, 2 H); 9.62 (br s, 1H); 11.46 (s, 1H)

MS-ESI: 407 [MH]+

Elemental analysis: Found C 52.8 H 4.6 N 10.9 $C_{22}H_{19}N_4O_3F$ $1H_2O$ 2HCl Requires C 53.1 H 4.6 N 11.3%

The starting chloroquinazoline was prepared as follows:

Sodium hydride (400 mg of an 80% suspension in paraffin oil, 13.3 mmol) was added to a solution of phenol (1.26 g, 13.3 mmol) in dry N-methylpyrrolidone (20 ml) and the mixture stirred for 10 minutes.

7-Benzyloxy-4-chloro-6-methoxyquinazoline hydrochloride (1.6 g, 4.7 mmol), (prepared as described for the starting material in Example 1), was then added and the reaction mixture heated at 110° C. for 2 hours. The mixture was allowed to cool, water was added and the mixture extracted with ethyl acetate (3×100 ml). The combined extracts were then washed with 2M sodium hydroxide solution, water and brine. Removal of the solvent under reduced pressure gave 7-benzyloxy-6-methoxy-4-phenoxyquinazoline (1.6 g, 95%) as a yellowish solid.

$^1$H NMR Spectrum: (DMSOd$_6$) 3.98 (s, 3H); 5.37 (s, 2H); 7.25–7.6 (m, 11 H); 7.60 (s, 1H); 8.54 (s, 1H)

MS-ESI: 359 [MH]+

7-Benzyloxy-6-methoxy-4-phenoxyquinazoline (160 mg, 0.44 mmol) in TFA (3 ml) was heated at reflux for 30 minutes. The solvent was removed by evaporation and the residue treated with aqueous sodium hydrogen carbonate solution. The precipitated product was collected by filtration, washed with water and dried to give 7-hydroxy-6-methoxy-4-phenoxyquinazoline (105 mg, 88%).

1H NMR Spectrum: (DMSOd$_6$) 4.00 (s, 3H); 7.20 (s, 1H); 7.25–7.35 (m, 3H); 7.4–7.55 (m, 2H); 7.58 (s, 1H); 10.73 (s, 1H)

MS-ESI: 269 [MH]+

A mixture of 7-hydroxy-6-methoxy-4-phenoxyquinazoline (95 mg, 0.35 mmol), 4-chloromethyl pyridine hydrochloride (120 mg, 0.74 mmol) and potassium carbonate (200 mg, 1.4 mmol) in DMF (5 ml) were heated at 80° C. for 2 hours. The reaction mixture was allowed to cool, water was added and the mixture extracted with ethyl acetate (3×50 ml). The combined extracts were then washed with water and dried (MgSO$_4$). The solvent was removed by evaporation and the residue triturated with an ethyl acetate/hexane mixture to give 6-methoxy-4-phenoxy-7-(4-pyridylmethoxy)quinazoline (44 mg, 35%) as a white solid.

$^1$H NMR Spectrum: (DMSOd$_6$) 4.02 (s, 3H); 5.47 (s, 2H); 7.25–7.35 (m, 3H); 7.45 (s, 1H); 7.4–7.55 (m, 4H); 7.62 (s, 1H); 8.52 (s, 1H); 8.63 (dd, 2H)

MS-ESI: 360 [MH]+

A solution of 6-methoxy-4-phenoxy-7-(4-pyridylmethoxy)quinazoline (200 mg, 0.56 mmol) in 2M hydrochloric acid (15 ml) was heated at reflux for 90 minutes. The reaction mixture was allowed to cool and neutralised to pH6–7 with aqueous ammonia. The precipitated product was extracted with methanol/methylene chloride (1:9) and the extract solution dried (MgSO$_4$). Removal of the solvent by evaporation gave 6-methoxy-7-(4-pyridylmethoxy)-3,4-dihydroquinazolin-4-one (90 mg, 57%) as a grey solid.

$^1$H NMR Spectrum: (DMSOd$_6$) 3.93 (s, 3H); 5.35 (s, 2H); 7.18 (s, 1H); 7.48 (s, 1H); 7.50 (m, 2H); 8.04 (s, 1H); 8.62 (m, 2H)

MS-ESI: 284 [MH]+

Phosphorus oxytrichloride (0.1 ml) was added to a mixture of 6-methoxy-7-(4-pyridylmethoxy)-3,4-dihydroquinazolin-4-one (81 mg, 0.29 mmol) and N,N-dimethylaniline (0.1 ml) in toluene (5 ml), and the mixture heated at reflux for 1 hour. The volatiles were removed by evaporation and the residue partitioned between methylene chloride and aqueous ammonia. The organic extract was separated, dried (MgSO$_4$) and the solvent removed by evaporation. The residue was purified by chromatography on silica eluting with ethyl acetate progressing through increasingly polar mixtures to methanol/methylene chloride (⅑) to give 4-chloro-6-methoxy-7-(4-pyridylmethoxy)quinazoline (40mg, 41%).

1H NMR Spectrum: (DMSOd$_6$) 4.04(s, 3H); 5.47(s, 2H); 7.46(s, 1H); 7.50(d, 2H); 7.53(s, 1H); 8.60(d, 2H); 8.85(s, 1 H)

MS - ESI: 302 [MH]+

The starting aniline was prepared as described below:

Methyl chloroformate (6.8ml, 88mmol) was added over 30 minutes to a solution of 4-fluoro-2-methylphenol (10 g, 79mmol) in 6% aqueous sodium hydroxide solution at 0° C. The mixture was stirred for 2 hours, then extracted with ethyl acetate (100 ml). The ethyl acetate extract was washed with water (100 ml) and dried (MgSO$_4$) and the solvent removed by evaporation to give 4-fluoro-2-methylphenyl methyl carbonate (11.4 g, 78%) as an oil. $^1$H NMR Spectrum: (DMSOd$_6$) 2.14(s, 3H); 3.81(s, 3H); 7.05(m, 1H); 7.1–7.25(m, 2 H) A mixture of concentrated nitric acid (6 ml) and concentrated sulphuric acid (6 ml) was added slowly to a solution of 4-fluoro-2-methylphenyl methyl carbonate (11.34 g, 62 mmol) in concentrated sulphuric acid (6 ml) such that the temperature of the reaction mixture was kept below 50° C. The mixture was stirred for 2 hours, then ice/water was added and the precipitated product collected by filtration. The crude product was purified by chromatography on silica eluting with methylene chloride/hexane progressing through increasingly polar mixtures to methanol/methylene chloride (¹/₁₉) to give 4-fluoro-2-methyl-5-nitrophenol (2.5 g, 22%) as a solid.

$^1$HNMR Spectrum: (DMSOd$_6$; CD$_3$COOD) 2.31(s, 3H); 7.38(d, 1H); 7.58(d, 1H)

MS - ESI: 171 [MH]+

A mixture of 4-fluoro-2-methyl-5-nitrophenol (2.1 g, 13 mmol), iron powder (1 g, 18 mmol) and iron(II)sulphate (1.5 g, 10 mmol) in water (40 ml) was refluxed for 4 hours. The reaction mixture was allowed to cool, neutralised with 2M aqueous sodium hydroxide and extracted with ethyl acetate (100 ml). The ethyl acetate extract was dried (MgSO$_4$) and the solvent removed by evaporation to give 2-fluoro-5-hydroxy-4-methylaniline (0.8 g, 47%) as a solid.

$^1$H NMR Spectrum: (DMSOd$_6$) 1.94(s, 3H); 4.67(s, 2H); 6.22(d, 1H); 6.65(d, 1H); 8.68(s, 1H)

MS - ESI: 142 [MH]+

Example 14

A solution of 7-benzyloxy-4-(2-fluoro-5-methoxycarbonyloxy-4-methylanilino)-6-methoxyquinazoline hydrochloride (259 mg, 0.54 mmol), (prepared as described for the starting material in Example 12), in methanol (15 ml) containing 1M sodium hydroxide (1.6 ml) was stirred at ambient temperature for 1 hour. After addition of water (15 ml), concentrated hydrochloric acid (1 ml) was added and the mixture was stirred at ambient temperature for 15 minutes. After evaporation of methanol, the precipitate was filtered, washed with water and dried under vacuum to give 7-benzyloxy-4-(2-fluoro-5-hydroxy-4-methylanilino)-6-methoxyquinazoline hydrochloride (192 mg, 80%).

m.p. 294–298° C.

$^1$H NMR Spectrum: (DMSOd$_6$) 2.2(s, 3H); 4.05(s, 3H); 5.35(s, 2H); 6.9(d, 1H); 7.12(d, 1H); 7.35–7.5(m, 4H); 7.55–7.6(m, 2H); 8.25(s, 1H); 8.8(s, 1H); 9.7(s, 1H); 11.35 (s, 1H)

MS - ESI: 406 [MH]+

Elemental analysis: Found C 62.3 H 4.9 N 9.3 C$_{23}$H$_{20}$N$_3$O$_3$F 0.16H$_2$O 1HCl Requires C 62.1 H 4.8 N 9.5%

Example 15

A mixture of 4-(4-chloro-2-fluoroanilino)-7-hydroxy-6-methoxyquinazoline (200 mg, 0.63 mmol), 2-(2-chloroethoxy)pyridine hydrochloride (120 mg, 0.61 mmol) and potassium carbonate (260 mg, 1.9 mmol) in DMF (25 ml) was heated at 90° C. for 16 hours. The mixture was diluted with water and extracted with ethyl acetate. The extract was dried (MgSO$_4$) and the solvent removed by evaporation. The residue was purified by column chromatography eluting with ethyl acetate/methanol mixtures (100/0 increasing to 90/10) to give 4-(4-chloro-2-fluoroanilino)-6-methoxy-7-(2-(2-pyridyloxy)ethoxy) quinazoline (20 mg, 7%) as an off-white solid.

$^1$H NMR Spectrum: (DMSOd$_6$) 3.99(s, 3H); 4.35(t, 2H); 4.42(t, 2H); 6.22(t, 1H); 6.40(d, 1H); 7.42(s, 1H); 7.55(d, 2H); 7.71(d, 1H); 7.85(t, 1H); 8.55(d, 1H); 9.62(s, 1H)

MS - ESI: 441 [MH]+

The starting material was prepared as follows:

A solution of 7-benzyloxy-4-chloro-6-methoxyquinazoline hydrochloride (1.34 g, 4 mmol), (prepared as described for the starting material in Example 1), and 4-chloro-2-fluoroaniline (444 μ, 4 mmol) in isopropanol (40 ml) was refluxed for 1.5 hours. After cooling, the precipitate was collected by filtration, washed with isopropanol then ether and dried under vacuum to give 7-benzyloxy-4-(4-chloro-2-fluoroanilino)-6-methoxyquinazoline hydrochloride (1.13 g, 64%).

m.p. 239–242° C.

$^1$H NMR Spectrum: (DMSOd$_6$) 4.0(s, 3H); 5.36(s, 2H); 7.39–7.52(m, 9H); 8.1(s, 1H); 8.75(s, 1H)

MS - ESI: 410 [MH]$^+$

Elemental analysis: Found C 59.2 H 4.3 N 9.4 $C_{22}H_{17}N_3ClFO_2$ 1HCl Requires C 59.2 H 4.1 N 9.41%

A solution of 7-benzyloxy-4-(4-chloro-2-fluoroanilino)-6-methoxyquinazoline hydrochloride (892 mg, 2 mmol) in TFA (10 ml) was refluxed for 50 minutes. After cooling, the mixture was poured onto ice. The precipitate was collected by filtration, dissolved in methanol (10 ml) and basified to pH11 with aqueous ammonia. After concentration by evaporation, the solid product was collected by filtration, washed with water then ether and dried under vacuum to give 4-(4-chloro-2-fluoroanilino)-7-hydroxy-6-methoxyquinazoline as a yellow solid (460 mg, 72%).

m.p. 141–143° C.

$^1$H NMR Spectrum: (DMSOd$_6$) 3.95(s, 3H); 7.05(s, 1H); 7.35(d, 1H); 7.54–7.59(m, 2H); 7.78(s, 1H); 8.29(s, 1H)

MS - ESI: 320–322 [MH]$^+$

Thionyl chloride (0.55 ml, 7.55 mmol) was added to a solution of 2-(2-hydroxyethoxy)pyridine (700 mg, 5.04 mmol), (J. Org. Chem. 1977, 42, 1500), in trichloromethane (20 ml) at 5° C. The mixture was stirred for 1 hour at 5° C, allowed to warm to ambient temperature and stirred for a further 1 hour. The volatiles were removed by evaporation and by azeotroping with toluene to give 2-(2-chloroethoxy) pyridine hydrochloride (970 mg, 99%).

$^1$H NMR Spectrum: (DMSOd$_6$) 3.90(t, 2H); 4.20(t, 2H); 6.22(d, 1H); 6.40(d, 1H); 7.44(dd, 1H); 7.64(d, 1H)

MS - ESI: 158 [MH]$^+$

Example 16

Triphenylphosphine (5.5 g, 21 mmol) followed by 2-[N-methyl-N-(4-pyridyl)]aminoethanol (1.49 g, 9.8 mmol), (prepared as described in EP 0359389 A1), were added to a stirred solution of 4-(4-chloro-2-fluoroanilino)-7-hydroxy-6-methoxyquinazoline (2.23 g, 7 mmol), (prepared as described for the starting material in Example 15), in methylene chloride (60 ml) under nitrogen. Diethyl azodicarboxylate (3.65 g, 21 mmol) was then added dropwise and the mixture was stirred at ambient temperature for 2 hours. Ethyl acetate (200 ml) was added and the mixture was stirred for a further 2 hours. The solid product was collected by filtration, washed with ethyl acetate, dried under vacuum and finally purified by column chromatography eluting with methylene chloride/methanol (75/25 followed by 60/40 and 50/50) to give a white solid. The purified product was dissolved in methylene chloride/methanol and the insolubles removed by filtration. Ethereal hydrogen chloride (10 ml of 3M solution) was added to the filtrate and the volatiles were removed by evaporation. The residue was triturated with ether and the solid product collected by filtration and dried under vacuum to give 4-(4-chloro-2-fluoroanilino)-6-methoxy-7-(2-[N-methyl-N-(4-pyridyl)]aminoethoxy) quinazoline hydrochloride (2.75 g, 75%) as a white solid.

m.p. 222–227° C.

$^1$H NMR Spectrum: (DMSOd$_6$; CF$_3$COOD) 3.29(s, 3H); 3.95(s, 3H); 4.16(t, 2H); 4.48(t, 2H); 7.05(br s, 1H); 7.37(s, 2H); 7.42(d, 1H); 7.58(t, I1H); 7.65(dd, 1H); 8.18(s, 1H); 8.28(br s, 2H); 8.86(s, 1H)

MS - ESI: 454 [MH]$^+$

Elemental Analysis: Found C 51.2 H 4.8 N 12.9 $C_{23}H_{21}N_5O_2ClF$ 0.9H$_2$O 2HCl Requires C 50.9 H 4.6 N 12.9%

Example 17

A mixture of 4-(4-chloro-2-fluoroanilino)-7-hydroxy-6-methoxyquinazoline (300 mg, 0.94 mmol), (prepared as described for the starting material in Example 15), 4-(2-chloroethoxy)pyridine hydrochloride (155 mg, 0.79 mmol) and potassium carbonate (260 mg, 1.9 mmol) in NMP (20 ml) was heated at 90° C. for 2 hours, allowed to cool to ambient temperature and stirred for a further 18 hours. The mixture was diluted with water and extracted with ethyl acetate. The extract was washed with water, dried (MgSO$_4$) and the solvent removed by evaporation. The residue was purified by column chromatography eluting with methylene chloride/methanol mixtures (100/0 increasing to 95/5) to give 4-(4-chloro-2-fluoroanilino)-6-methoxy-7-(2-(4-pyridyloxy)ethoxy)quinazoline (20 mg, 7%).

m.p. 200–202° C.

$^1$H NMR Spectrum: (DMSOd$_6$) 3.90(s, 3H); 4.50(s, 4H); 7.04(d, 2H); 7.26(s, 1H); 7.33(dd, 1H); 7.5–7.6(m, 2H); 7.80(s, 1H); 8.35(s, 1H); 8.39(d, 2H); 9.52(s, 1H)

MS - ESI: 441 [MH]$^+$

The starting material was prepared as follows:

Thionyl chloride (0.75 ml, 10 mmol) was added to a solution of 4-(2-hydroxyethoxy)pyridine (0.9 g, 6.5 mmol), (J. Chem. Soc. Perkin II, 1987, 1867), in trichloromethane (20 ml) at 5° C. The mixture was stirred for 1 hour at 5° C., allowed to warm to ambient temperature and stirred for a further 2 hours. The volatiles were removed by evaporation and by azeotroping with toluene to give 4-(2-chloroethoxy) pyridine hydrochloride (1.3 g, 100%).

$^1$H NMR Spectrum: (DMSOd$_6$) 4.03(t, 2H); 4.62(t, 2H); 7.58(d, 2H); 8.77(d, 2H)

MS - ESI: 158 [MH]$^+$

Example 18

A mixture of 4-(4-chloro-2-fluoroanilino)-7-hydroxy-6-methoxyquinazoline (300 mg, 0.94 mmol), (prepared as described for the starting material in Example 15), 1-(2-chloroethyl)-1,2-dihydro-2-pyridone (175 mg, 1.11 mmol), (J. Am. Chem. Soc. 1951, 73, 3635), and potassium carbonate (260 mg, 1.9 mmol) in DMF (30 ml) was heated at 80° C. for 3 hours, allowed to cool to ambient temperature and stirred for a further 18 hours. The mixture was diluted with water and extracted with ethyl acetate. The extract was washed with water, dried (MgSO$_4$) and the solvent removed by evaporation. The residue was purified by column chromatography eluting with methylene chloride/methanol/triethylamine mixtures (100/0/0 increasing to 70/30/0.5) to give 4-(4-chloro-2-fluoroanilino)-6-methoxy-7-[2-(2-oxo-1,2-dihydro-1-pyridyl)ethoxy]quinazoline (50 mg, 12%).

m.p. 209–211° C.

$^1$H NMR Spectrum: (DMSOd$_6$) 3.94(s, 3H); 4.35(t, 2H); 4.41(t, 2H); 6.22(dd, 1H); 6.40(d, 1H); 7.14(s, 1H); 7.35(dd, 1H); 7.42(ddd, 1H); 7.5–7.6(m, 2H); 7.70(d, 1H); 7.80(s, 1H); 8.35(s, 1H); 9.53(s, 1H)

MS - ESI: 441 [MH]$^+$

Example 19

1-(3-Hydroxypropyl)-1,4-dihydro-4-pyridone ($^2$20 mg, 1.44 mmol) in methylene chloride (4 ml) followed by 1,1'-(Azodicarbonyl)dipiperidine (720 mg, 2.86 mmol) were added to a stirred solution of 4-(4-chloro-2-fluoroanilino)-7-hydroxy-6-methoxyquinazoline (300 mg, 0.94 mmol), (prepared as described for the starting material in Example 15), and tributylphosphine (0.69 ml, 2.8 mmol) in methylene chloride (20 ml) under nitrogen at 5° C. The mixture was stirred at 5° C. for 3 hours, allowed to warm to ambient temperature and stirred for a further 18 hours. The solvent was removed by evaporation and the residue partitioned between ethyl acetate and water. The organic phase was separated, dried (MgSO$_4$), and solvent removed by evaporation. The residue was purified by column chromatography eluting with methylene chloride/methanol/triethylamine mixtures (100/0/0 increasing to 70/30/0.5) to give 4-(4-chloro-2-fluoroanilino)-6-methoxy-7-[3-(4-oxo-1,4-dihydro-1-pyridyl)propoxy]quinazoline (48 mg, 11%).

m.p. >250° C.

$^1$H NMR Spectrum: (DMSOd$_6$) 3.56(m, 2H); 4.00(s, 3H); 3.54(t, 2H); 4.38(t, 2H); 7.42(d, 1H); 7.5–7.65(m, 5H); 8.43(s, 1H); 8.65–8.75(m, 4H)

MS - ESI: 455 [MH]$^+$

The starting material was prepared as follows:

Sodium hydride (946 mg of a 50% suspension in mineral oil, 19.7 mmol) was added to a solution of 4-hydroxypyridine (1.88 g, $^1$9.7 mmol) in DMF (50 ml) and the mixture stirred for 30 minutes. 2-($^3$-Bromopropoxy)tetrahydropyran (4.0 g, 17.9 mmol), (J. Chem. Soc. 1963, 3440), was added and the mixture heated at 100° C. for 3 hours. The reaction mixture was allowed to cool, diluted with water and extracted with ethyl acetate. The extract was washed with water, dried (MgSO$_4$) and the solvent removed by evaporation. The residue was purified by column chromatography eluting with methylene chloride/methanol mixtures (100/0 increasing to 95/5) to give 1-[3-(tetrahydropyran-2-yloxy)propyl]-1,4-dihydro-4-pyridone (1.5 g, 35%).

$^1$H NMR Spectrum: (DMSOd$_6$) 1.35–1.75(m, 6H); 1.95(t, 2H); 3.35–3.5(m, 2H); 3.65–3.8(m, 2H); 4.12(t, 2H); 4.57(s, 1H); 6.95(s, 2H); 7.94(s, 2H).

A solution of 1-[3-(tetrahydropyran-2-yloxy)propyl]-1,4-dihydro4-pyridone (0.75 g, 3.16 mmol) in acetic acid (8 ml), THF (4 ml) and water (4 ml) was heated at 50° C. for 4 hours. The volatiles were removed by evaporation to give 1-(3-hydroxypropyl)-l,4-dihydro-4-pyridone (480 mg, 99%) as an off-white solid.

$^1$H NMR Spectrum: (DMSOd$_6$) 1.9–1.95(m, 2H); 1.97–2.05(m, 2H); 4.0–4.1(m, 2H); 6.91(m, 2H); 8.36(m, 2H)

MS - ESI: 154 [MH]$^+$

Example 20

1-(2-Hydroxyethyl)-1,4-dihydro-4-pyridone (221 mg, 1.6 mmol) was added to a stirred solution of 4-(4-chloro-2-fluoroanilino)-7-hydroxy-6-methoxyquinazoline (230 mg, 0.7 mmol), (prepared as described for the starting material in Example 15), and tributylphosphine (0.53 ml, 2.1 mmol) in methylene chloride (20 ml) under nitrogen at 5° C. 1,1'-(Azodicarbonyl)dipiperidine (552 mg, 2.2 mmol) was added in portions over 10 minutes and the mixture was stirred at 5° C. for 2 hours, allowed to warm to ambient temperature and stirred for a further 18 hours. The mixture was diluted with ether, the insolubles removed by filtration and the solvent was removed from the filtrate by evaporation. The residue was partitioned between ethyl acetate and water, the organic phase was separated and dried (MgSO$_4$), and solvent was removed by evaporation. The residue was dissolved in acetone and ethereal hydrogen chloride (1.2 ml of a 3M solution) was added. The mixture was left to stand for 15 minutes and the precipitated product was collected by filtration, washed with ether and dried to give 4-(4-chloro-2-fluoroanilino)-6-methoxy-7-[2-(4-oxo-1,4-dihydro-1-pyridyl)ethoxy]quinazoline hydrochloride (54 mg, 16%).

$^1$H NMR Spectrum: (DMSOd$_6$) 3.98(s, 3H); 4.63(dd, 2H); 4.83(dd, 2H); 7.42(d, 1H); 7.50(s, 1H); 7.56(d, 1H); 7.6–7.65(m, 3H); 8.39(s, 1H); 8.77(s, 1H); 8.80(s, 2H)

MS - ESI: 441 [MH]$^+$

The starting material was prepared as follows:

Sodium hydride (1.27 g of a 50% suspension in mineral oil, 26.4 mmol) was added to a solution of 4-hydroxypyridine (2.5 g, 26 mmol) in DMF (50 ml) and the mixture stirred for 30 minutes. 2-(2-Bromoethoxy)tetrahydropyran (5.0 g, 23.9 mmol), (J. Am. Chem. Soc. 1948, 70, 4187), in DMF (5 ml) was added and the mixture heated at 80° C. for 3 hours. The reaction mixture was allowed to cool, diluted with water and extracted with ethyl acetate. The extract was washed with water, dried (MgSO$_4$) and the solvent removed by evaporation. The residue was purified by column chromatography eluting with methylene chloride/methanol mixtures (100/0 increasing to 97/3) to give 1-[2-(tetrahydropyran-2-yloxy)ethyl]-1,4-dihydro-4-pyridone (1.5 g, 28%).

$^1$H NMR Spectrum: (DMSOd$_6$) 1.39–1.68(m, 6H); 3.39–3.44(m, 1H); 3.64–3.78(m, 2H); 3.86–3.92(m, 1H); 4.20(t, 2H); 4.64(s, 1H); 6.95(d, 2H); 8.36(d, 2H)

MS - ESI: 224 [MH]$^+$

A solution of 1-[2-(tetrahydropyran-2-yloxy)ethyl]-1,4-dihydro-4-pyridone (500 mg, 2.23 mmol) in acetic acid (4 ml), THF (2 ml) and water (1 ml) was heated at 45° C. for 4 hours. The volatiles were removed by evaporation to give 1-(2-hydroxyethyl)-1,4-dihydro-4-pyridone (221 mg, 71%) as an off-white solid.

$^1$H NMR Spectrum: (DMSOd$_6$) 3.70(t, 2H); 4.06(t, 2H); 6.95(d, 2H); 8.37(d, 2H)

Example 21

A solution of 7-benzyloxy-4-chloro-6-methoxyquinazoline hydrochloride (132 mg, 0.4 mmol), (prepared as described for the starting material in Example 1), and 2-fluoro-5-methoxycarbonyloxy-4-methylphenol (96 mg, 0.48 mmol) in pyridine (2 ml) was heated at reflux for 3 hours. The mixture was allowed to cool, the solvent was removed by evaporation and the residue was partitioned between ethyl acetate and water. The organic layer was separated, washed with water, brine, dried (MgSO$_4$) and the solvent removed by evaporation. The residue was purified by column chromatography eluting with methylene chloride/ether (70/30). The resulting solid was crystallised from methylene chloride and methanol to give 7-benzyloxy-4-(2-fluoro-5-hydroxy-4-methylphenoxy)-6-methoxyquinazoline (120 mg, 64%).

$^1$H NMR Spectrum: (DMSOd$_6$) 2.15(s, 3H); 3.98(s, 3H); 5.35(s, 2H); 6.75(d, 1H); 7.13(d, 1H); 7.37(d, 1H); 7.45(t, 2H); 7.48–7.56(m, 3H); 7.58(s, 1H); 8.54 (s, 1H); 9.65(br s, 1H)

MS - ESI: 454 [MH]$^+$

Elemental Analysis: Found C 67.8 H 4.9 N 6.9 C$_{23}$H$_{19}$N$_2$O$_4$F 0.1H$_2$O Requires C 67.7 H 4.7 N 6.9%

The starting material was prepared as follows:

A mixture of (4-fluoro-2-methyl-5-nitrophenyl) methyl carbonate (8 g, 35 mmol), (EP 0307777 A2), and platinum (IV)oxide (174 mg) in ethanol (100 ml) and ethyl acetate (70 ml) was stirred under hydrogen at 1.3 atmospheres pressure for 1.5 hours. The catalyst was removed by filtration through diatomaceous earth and the solvent removed by evaporation. The residue was purified by column chromatography eluting with petroleum ether/ethyl acetate (7/3) to give 2-fluoro-5-methoxycarbonyloxy4-methylaniline (6.56 g, 94%) as an oil which crystallised.

$^1$H NMR Spectrum (CDCl$_3$): 2.09(s, 3H); 3.66(br s, 2H); 3.90(s, 3H); 6.54(d, 1H); 6.83(d, 1H)

A solution of sodium nitrite (1.63 g, 23 mmol) in water (19ml) and ice (48 g) was added dropwsie to a solution of 2-fluoro-5-methoxycarbonyloxy-4-methylaniline (3.93 g, 20 mmol) in 35% sulphuric acid (48 ml) at 0° C. The reaction mixture was stirred at 0° C. for 30 minutes and a solution of copper(II)nitrate trihydrate (467 g, 1.93mol) in water (780 ml). followed by copper(II)oxide (2.65 g, 18 mmol) were added. The solution was extracted with ethyl acetate, the organic layer was washed with brine, dried (MgSO$_4$) and the solvent removed by evaporation. The residue was purified by column chromatography eluting with petroleum ether/ethyl acetate (8/2) to give 2-fluoro-5-methoxycarbonyloxy-4-methylphenol (2.13 g, 53%) as a yellow solid.

$^1$H NMR Spectrum (CDCl$_3$): 2.13(s, 3H); 3.91(s, 3H); 5.11(br s, 1H); 6.78(d, 1H); 6.93(d, 1H)

Example 22

A mixture of 4-(2-fluoro-5-methoxycarbonyloxy-4-methylanilino)-7-hydroxy-6-methoxyquinazoline hydrochloride (470 mg, 1 mmol), 4-chloromethyl-2-methylthiazole hydrochloride (368 mg, 2 mmol), potassium carbonate (414 mg, 3 mmol) and potassium iodide (40 mg) in DMF (15 ml) was heated at 60° C. for 24 hours. The mixture was allowed to cool and partitioned between ethyl acetate and water. The organic layer was washed with water and brine, dried (MgSO$_4$) and the solvent removed by evaporation. The residue was dissolved in methanol (15 ml) and 1M sodium hydroxide (2 ml) was added and the mixture stirred for 30 minutes. Concentrated hydrochloric acid (0.5 ml) was added. The solvent was removed by evaporation. The residue was purified by reverse phase HPLC eluting with a gradient (0–70%) of methanol in water. Concentrated hydrochloric acid (0.3 ml) was added to the combined fractions of pure product and the solvent was removed by evaporation. The residue was triturated with acetone, collected by filtration, washed with acetone and dried under vacuum at 55° C. to give 4-(2-fluoro-5-hydroxy-4-methylanilino)-6-methoxy-7-((2-methylthiazol-4-yl)methoxy)quinazoline hydrochloride (225 mg, 48%).

$^1$H NMR Spectrum: (DMSOd$_6$) 2.17(s, 3H); 2.69(s, 3H); 4.00(s, 3H); 4.7(br s, 1H); 5.34(s, 2H); 6.91(d, 1H); 7.1(d, 1H); 7.60(s, 1H); 7.74(s, 1H); 8.33(s, 1H); 8.79(s, 1H); 11.5(s, 1H)

MS - ESI: 427 [MH]$^+$

The starting material was prepared as follows:

A mixture of (4-fluoro-2-methyl-5-nitrophenyl) methyl carbonate (3 g, 13 mmol), (EP 0307777 A2), and platinum (IV)oxide (300 mg) in ethanol (60 ml) was stirred under hydrogen at 0.3 atmosphere for 1 hour. The catalyst was removed by filtration through diatomaceous earth and the solvent removed by evaporation to give 2-fluoro-5-methoxycarbonyloxy-4-methylaniline (2.6 g, 100%) as a solid.

1H NMR Spectrum: (CDCl$_3$) 2.07(s, 3H); 3.87(s, 3H); 6.52(d, 1 H); 6.80(d, 1H)

A solution of 7-benzyloxy-4-chloro-6-methoxyquinazoline hydrochloride (800 mg, 2.4 mmol), (prepared as described for the starting material in Example 1), and 2-fluoro-5-methoxycarbonyloxy-4-methylaniline (570 mg, 2.89 mmol) in isopropanol (20 ml) was heated at reflux for 2 hours. The mixture was allowed to cool to ambient temperature, the precipitated solid was collected by filtration, washed with isopropanol and dried under vacuum to give 7-benzyloxy-4-(2-fluoro-5-methoxycarbonyloxy-4-methylanilino)-6-methoxyquinazoline hydrochloride (1.0 g, 77%).

$^1$H NMR Spectrum: (DMSOd$_6$; CF$_3$COOD) 2.2(s, 3H); 3.85(s, 3H); 4.0(s, 3H); 5.37(s, 2H); 7.3–7.55(m, 8H); 8.13(s, 1H); 8.86(s, 1H)

MS - ESI: 464 [MH]$^+$

A mixture of 7-benzyloxy-4-(2-fluoro-5-methoxycarbonyloxy-4-methylanilino)-6-methoxyquinazoline hydrochloride (700 mg, 1.4 mmol) and 10% palladium-on-charcoal (100 mg) in DMF (10 ml), methanol (10 ml) and trichloromethane (10 ml) was stirred under hydrogen at 1 atmosphere pressure for 1 hour. The catalyst was removed by filtration through diatomaceous earth and the solvent was removed by evaporation. The residue was triturated with ether, collected by filtration and dried under vacuum to give 4-(2-fluoro-5-methoxycarbonyloxy-4-methylanilino)-7-hydroxy-6-methoxyquinazoline hydrochloride (570 mg, 98%).

$^1$H NMR Spectrum: (DMSOd6) 2.23(s, 3H); 3.87(s, 3H); 4.01(s, 3H); 7.37(s, 1H); 7.45(d, 1H); 7.5(d, 1H); 8.20(s, 1H); 8.77(s, 1H); 11.35(s, 1H); 11.79(s, 1H)

MS - ESI: 374 [MH]$^+$

Example 23

A mixture of 4-chloro-7-(4-pyridylmethoxy)quinazoline hydrochloride (350 mg, 1 mmol) and 2-fluoro-5-hydroxy-4-methylaniline (155 mg, 1.1 mmol), (prepared as described for the starting material in Example 13), in isopropanol (15 ml) was heated at reflux for 1 hour. The resulting precipitate was collected by filtration and purified by reverse phase HPLC using a gradient (0–75%) of methanol in water. Concentrated hydrochloric acid (0.5 ml) was added to the combined fractions of pure product and the solvent was removed by evaporation to give 4-(2-fluoro-5-hydroxy-4-methylanilino)-7-(4-pyridylmethoxy)quinazoline hydrochloride (140 mg, 28%).

$^1$H NMR Spectrum: (DMSOd6) 2.16(s, 3H); 5.69(s, 2H); 6.19(d, 1H); 7.1(d, 1H); 7.48(d, 1H); 7.66(dd, 1H); 8.06(d, 2H); 8.84(s, 1H); 8.86(d, 1H); 8.90(d, 2H); 9.7(br s, 1H); 11.71(s, 1H)

MS - ESI: 377 [MH]$^+$

Elemental Analysis: Found C 50.9 H 4.9 N 11.1 C$_{21}$H$_{17}$N$_4$O$_2$F 2.4H$_2$O 2HCl Requires C 51.2 H 4.9 N 11.4%

The starting material was prepared as follows:

Sodium hydride (0.72 g of a 60% suspension in mineral oil, 18 mmol) was added to a solution of 4-hydroxymethylpyridine (4 g, 36 mmol) in THF (30 ml) and the mixture heated at reflux for 15 minutes. 7-Fluoro-3,4-dihydroquinazolin-4-one (1 g, 6 mmol), (J. Chem. Soc. section B 1967, 449), was added, the THF was removed by evaporation, and the mixture was heated at 120° C. for 30 minutes. The mixture was allowed to cool, diluted with water (40 ml) and was adjusted to pH8 with concentrated hydrochloric acid. The resulting precipitate was collected by filtration, washed with water, then ether and dried under vacuum to give 7-(4-pyridylmethoxy)-3,4-dihydroquinazolin-4-one (1.12 g, 71 %).

¹H NMR Spectrum (DMSOd₆) 5.35(s, 2H); 7.15–7.22(m, 2H); 7.5(d, 2H); 8.05(d, 1H); 8.07 (s, 1H); 8.6(d,2H).

A mixture of 7-(4-pyridylmethoxy)-3,4-dihydroquinazolin-4-one (320 mg, 1.26 mmol), DMF (1 drop) and thionyl chloride (10 ml) was heated at 60° C. for 1 hour. The volatiles were removed by evaporation, the residue was triturated with ether, collected by filtration, washed with ether and dried under vacuum to give 4-chloro-7-(4-pyridylmethoxy)quinazoline hydrochloride (435 mg, 98%).

¹H NMR Spectrum (DMSOd₆) 5.7(s, 2H); 7.32(s, 1H); 7.35(d, 1H); 8.1–8.2(m,3H); 8.62(s,1 H); 9.0(d,2H).

MS - ESI: 272 [MH]⁺

Example 24

A solution of 1,1'-(azodicarbonyl)dipiperidine (378 mg, 1.5 mmol) in methylene chloride (5 ml) was added dropwise to a suspension of 4-(4-chloro-2-fluoroanilino)-7-hydroxy-6-methoxyquinazoline (160 mg, 0.5 mmol), tributylphosphine (303 mg, 1.5 mmol) and 2-(imidazol-1-yl)ethanol (67 mg, 0.6 mmol), (J. Med. Chem. 1993, 25, 4052–4060), in methylene chloride (8 ml) and the mixture was stirred for 3 hours at ambient temperature. Acetic acid (60 mg, 1 mmol) was added and the solvent was removed by evaporation. The solid residue was adsorbed on silica and purified by column chromatography eluting with methylene chloride/methanol (9/1 followed by 8/2). The resulting white solid was dissolved in methylene chloride/methanol and a solution of 5M hydrochloric acid in isopropanol was added. The solvent was removed by evaporation and the solid was triturated with ether, filtered, washed with ether and dried under vacuum to give 4-(4-chloro-2-fluoroanilino)-7-(2-(imidazol-1-yl)ethoxy)-6-methoxyquinazoline hydrochloride (1 80 mg, 74%).

¹H NMR Spectrum: (DMSOd₆) 4.01(s, 3H); 4.62(t, 2H); 4.76(t, 2H); 7.44(dd, 1H); 7.48(s, 1H); 7.59(t, 1H); 7.66(dd, 1H); 7.72(s, 1H); 7.84(s, 1H); 8.41(s, 1H); 8.78(s, 1H); 9.22(s, 1H)

MS - ESI: 414 [MH]⁺

Elemental Analysis: Found C 48.3 H 4.1 N 14.0 C₂₀H₁₇N₅O₂ClF 0.4H₂O 2HCl Requires C 48.6 H 4.0 N 14.2%

The starting material was prepared as follows:

A solution of 7-benzyloxy-4-chloro-6-methoxyquinazoline hydrochloride (1.2 g, 3.6 mmol), (prepared as described for the starting material in Example 1), and 4-chloro-2-fluoroaniline (444 μl, 4 mmol) in isopropanol (40 ml) was heated at reflux for 1.5 hours. The mixture was allowed to cool, the precipitate was collected by filtration, washed with isopropanol then ether and dried under vacuum to give 7-benzyloxy4-(4-chloro-2-fluoroanilino)-6-methoxyquinazoline hydrochloride (1.13 g, 71%).

m.p. 239–242° C.

¹H NMR Spectrum: (DMSOd₆) 4.0(s, 3H); 5.36(s, 2H); 7.39–7.52(m, 9H); 8.1(s, 1H); 8.75(s, 1H)

MS - ESI: 410 [MH]⁺

Elemental analysis: Found C 59.2 H 4.3 N 9.4 C₂₂H₁₇N₃O₂ClF HCl Requires C 59.2 H 4.1 N 9.4%

A solution of 7-benzyloxy-4-(4-chloro-2-fluoroanilino)-6-methoxyquinazoline hydrochloride (892 mg, 2 mmol) in TFA (10 ml) was heated at reflux for 50 minutes. The mixture was allowed to cool and then poured on to ice. The precipitate was collected by filtration, dissolved in methanol (10 ml) and basified to pH11 with aqueous ammonia. The mixture was concentrated by evaporation, the resulting solid product was collected by filtration, washed with water then ether and dried under vacuum to give 4-(4-chloro-2-fluoroanilino)-7-hydroxy-6-methoxyquinazoline (460 mg, 72%) as a yellow solid.

m.p. 141–143° C.

¹H NMR Spectrum: (DMSOd₆) 3.95(s, 3H); 7.05(s, 1H); 7.35(d, 1H); 7.54–7.59(m, 2H); 7.78(s, 1H); 8.29(s, 1H)

MS - ESI: 320 [MH]⁺

Example 25

A mixture of 4-(4-chloro-2-fluoroanilino)-7-hydroxy-6-methoxyquinazoline (448 mg, 1.4 mmol), (prepared as described for the starting material in Example 24), and potassium carbonate (676 mg, 4.9 mmol) in DMF (10 ml) was stirred at ambient temperature for 10 minutes. 4-Chloromethyl-2-methylthiazole hydrochloride (310 mg, 1.68 mmol) was added and the mixture was heated at 70° C. for 3.5 hours. The reaction mixture was allowed to cool and was partitioned between ethyl acetate and water. The organic layer was separated, washed with water, brine, dried (MgSO₄) and the solvent removed by evaporation. The solid residue was purified by column chromatography eluting with a mixture of methylene chloride/acetonitrile/methanol (50/45/5 followed by 50/40/10). The resulting purified solid was dissolved in methylene chloride/methanol and a solution of 5M hydrogen chloride in isopropanol (1 ml) was added. Partial evaporation led to the precipitation of a white solid. This solid was collected by filtration and dried under vacuum to give 4-(4-chloro-2-fluoroanilino)-6-methoxy-7-((2-methylthiazol-4-yl)methoxy)quinazoline hydrochloride (240 mg, 35%).

m.p. 220–225° C.

¹H NMR Spectrum: (DMSOd₆) 2.68(s, 3H); 4.0(s, 3H); 5.36(s, 2H); 7.46(dd, 1H); 7.54(s, 1H); 7.61(t, 1H); 7.7(d, 1H); 7.71(s, 1H); 8.26(s, 1H); 8.83(s, 1H)

MS - ESI: 431 [MH]⁺

Elemental Analysis: Found C 49.3 H 4.0 N 11.3 C₂₀H₁₆N₄O₂ClFS 0.3H₂O 1.5HCl Requires C 48.9 H 3.7 N 11.4%

Example 26

Using an analogous procedure to that described in Example 25, 4-(4-chloro-2-fluoroanilino)-7-hydroxy-6-methoxyquinazoline (224 mg, 0.7 mmol), (prepared as described for the starting material in Example 24), and 2-chloromethyl-1-methylimidazole hydrochloride (140 mg, 0.8 mmol) were combined to give 4-(4-chloro-2-fluoroanilino)-6-methoxy-7-((1-methylimidazol-2-yl)methoxy)quinazoline hydrochloride (150 mg, 44%).

¹H NMR Spectrum: (DMSOd₆) 3.94(s, 3H); 4.02(s, 3H); 5.69(s, 2H); 7.44(dd, 1H); 7.6(t, 1H); 7.64(s, 1H); 7.67(dd, 1H); 7.72(d, 1H); 7.81(d, 1H); 8.46(s, 1H); 8.81(s, 1H)

MS - ESI: 414 [MH]⁺

Elemental Analysis: Found C 48.7 H 4.6 N 13.6 C₂₀H₁₇N₅O₂ClF 0.5H₂O 2HCl Requires C 48.8 H 4.3 N 13.7% 0.25isopropanol

Example 27

A mixture of 4-(2-fluoro-5-methoxycarbonyloxy-4-methylanilino)-7-hydroxy-6-methoxyquinazoline hydrochloride (470 mg, 1 mmol), (prepared as described for the starting material in Example 22), 2-chloromethyl-1- methylimidazole hydrochloride (335 mg, 2 mmol), potassium carbonate (414 mg, 3 mmol) and potassium iodide (20 mg) in DMF (15 ml) was heated at 60° C. for 2 hours. The mixture was allowed to cool and partitioned between ethyl acetate and water. The organic layer was separated, washed with water and brine, dried ($MgSO_4$) and the solvent removed by evaporation. The crude product was dissolved in methanol (20 ml), 2M sodium hydroxide (1 ml) was added and the mixture stirred for 15 minutes. Concentrated hydrochloric acid (0.5 ml) was added and the solvent was removed by evaporation. The crude product was purified by reverse phase chromatography eluting with methanol/water (1/1). Concentrated hydrochloric acid (0.3 ml) was added to the combined fractions containing the pure product and the solvent was removed by evaporation to give 4-(2-fluoro-5-hydroxy-4-methylanilino)-6-methoxy-7-((1-methylimidazol-2-yl)methoxy)quinazoline hydrochloride (100 mg, 21%).

$^1$H NMR Spectrum: ($DMSOd_6$) 2.17(s, 3H); 3.95(s, 3H); 4.01(s, 3H); 5.70(s, 2H); 6.92(d, 1H); 7.12(d, 1H); 7.63(s, 1H); 7.77(s, 1H); 7.83(s, 1H); 8.43(s, 1H); 8.82(s, 1H); 9.7(br s, 1H); 11.62(br s, 1H)

MS - ESI: 410 [MH]$^+$

Example 28

Using an analogous procedure to that described in Example 27, 4-(2-fluoro-5-methoxycarbonyloxy-4-methylanilino)-7-hydroxy-6-methoxyquinazoline hydrochloride (470 mg 1.14 mmol), (prepared as described for the starting material in Example 22), and 2-acetamido-4-chloromethylthiazole (381 mg, 1.68 mmol) were combined to give 7-((2-acetamidothiazol-4-yl)methoxy)4-(2-fluoro-5-hydroxy-4-methylanilino)-6-methoxyquinazoline (135 mg, 25%).

$^1$H NMR Spectrum: ($DMSOd_6$; $CF_3COOD$) 2.16(s, 3H); 2.19(s, 3H); 4.00(s, 3H); 5.33(s, 2H); 6.91(d, 1H); 7.12(d, 1H); 7.33(s, 1H); 7.49(s, 1H); 8.16(s, 1H); 8.82(s, 1H)

MS - ESI: 470 [MH]$^+$

Elemental Analysis: Found C 51.5 H 4.5 N 13.8 $C_{22}H_{20}N_5O_4FS$ 0.4$H_2O$ 0.95HCl Requires C 51.7 H 4.3 N 13.7%

Example 29

A suspension of 7-benzyloxy-4-chloro-6-methoxyquinazoline hydrochloride (169 mg, 0.5mmol), (prepared as described for the starting material in Example 1), and 4-chloro-2-fluoro-5-hydroxyaniline (97 mg, 0.6 mmol), (EP 061741 A2), in isopropanol (5 ml) was heated at reflux for 2 hours. The resulting precipitate was collected by filtration, washed with isopropanol and ether and dried under vacuum to give 7-benzyloxy4-(4-chloro-2-fluoro-5-hydroxyanilino)-6-methoxyquinazoline hydrochloride (1 97 mg, 85%).

$^1$H NMR Spectrum: ($DMSOd_6$) 4.0(s, 3H); 5.36(s, 2H); 7.15(d, 1H); 7.4–7.5(m, 4H); 7.52(s, 1H); 7.54(d, 2H); 8.23(s, 1H); 8.8(s, 1H); 10.6(s, 1H); 11.39(br s, 1H)

MS - ESI: 426 [MH]$^+$

Elemental Analysis: Found C 57.1 H 4.2 N 8.9 $C_{22}H_{17}N_3O_3ClF$ 0.15$H_2O$ 1HCl Requires C 56.8 H 4.0 N 9.0% 0.4isopropanol

Example 30

1,1'-(Azodicarbonyl)dipiperidine (1.06 g, 4.2 mmol) in methylene chloride (15 ml) was added dropwise to a solution of 4-(4-chloro-2-fluoroanilino)-7-hydroxy-6-methoxyquinazoline (448 mg, 1.4 mmol), (prepared as described for the starting material in Example 24), tributylphosphine (848 mg, 4.2 mmol) and 4-(3-hydroxypropyl) pyridine (322 mg, 2.4 mmol) in methylene chloride (15 ml) and the mixture stirred for 3 hours at ambient temperature. Acetic acid (1 26 mg, 2.1 mmol) was added and the solvent was removed by evaporation. The residue was purified by column chromatography eluting with methylene chloride/methanol (95/5). The purified product was triturated with ether, the resulting solid collected and dissolved in methylene chloride (20 ml). 5M Hydrogen chloride in isopropanol solution (0.7 ml) was added, the solution was diluted with isopropanol (5 ml) and concentrated by evaporation to a total volume of 4 ml. Ether was added and the resulting soild was collected by filtration, washed with ether and dried under vacuum to give 4-(4-chloro-2-fluoroanilino)-6-methoxy-7-(3-(4-pyridyl)propoxy)quinazoline hydrochloride (520 mg, 73%).

$^1$H NMR Spectrum: ($DMSOd_6$) 2.30(m, 2H); 3.09(t, 2H); 3.97(s, 3H); 4.27(f,2H); 7.42(s, 1H); 7.44(d, 1H); 7.59(t, 1H); 7.67(dd, 1H); 7.95(d, 2H); 8.34(s, 1H); 8.8(s, 1H); 8.82(d, 2H)

MS - ESI: 439 [MH]$^+$

Elemental Analysis: Found C 53.6 H 4.8 N 10.7 $C_{23}H_{20}N_4O_2ClF$ 0.5$H_2O$ 2HCl Requires C 53.1 H 4.6 N 10.6% 0.1 isopropanol

Example 31

2M Aqueous sodium hydroxide (1.5 ml, 3 mmol) was added to a solution of 4-(4-chloro-2-fluoro-5-methoxycarbonyloxyanilino)-6-methoxy-7-(3-(4-pyridyl) propoxy)quinazoline (1.28 g, 2.5 mmol) in methanol (13 ml) and the mixture stirred for 2 hours at ambient temperature. Water was added and the mixture was adjusted to pH7 with 2M hydrochloric acid. The resulting precipitate was collected by filtration, washed with water and dried under vacuum. This solid was dissolved in methylene chloride (30 ml) and methanol (5 ml) and a solution of 5M hydrogen chloride in isopropanol (2.5 ml) was added. The solution was diluted with isopropanol and concentrated under vacuum to a total volume of 10 ml. The resulting solid was collected by filtration, washed with isopropanol and then ether and dried under vacuum to give 4-(4-chloro-2-fluoro-5-hydroxyanilino)-6-methoxy-7-(3-(4-pyridyl)propoxy) quinazoline hydrochloride (924 mg, 70%).

$^1$HNMR Spectrum: ($DMSOd_6$) 2.3(t, 2H); 3.12(t, 2H); 4.0(s, 3H); 4.28(t, 2H); 7.18(d, 1H); 7.4(s, 1H); 7.52(d, 1H); 7.95(d, 2H); 8.32(s, 1H); 8.82(s, 1H); 8.84(d, 2H); 10.65(s, 1H); 11.65(brs, 1H)

MS - ESI: 455 [MH]$^+$

Elemental Analysis: Found C 51.9 H 4.5 N 10.7 $C_{23}H_{20}N_4O_3ClF$ 0.55$H_2O$ 1.9HCl Requires C 51.5 H 4.7 N 10.5%

The starting material was prepared as follows:

1,1'-(Azodicarbonyl)dipiperidine (2.52 g, 10 mmol) in methylene chloride (10 ml) was added dropwise to a solution of 4-(2-fluoro-5-methoxycarbonyloxy-4-methylanilino)-7-hydroxy-6-methoxyquinazoline hydrochloride (1.38 g, 3.5 mmol), (prepared as described for the starting material in Example 22), tributylphosphine (2 g, 10.5 mmol) and 4-(3-hydroxypropyl)pyridine (720 mg, 5.25 mmol) in methylene chloride (25 ml) and the mixture stirred for 2.5 hours at ambient temperature. The solvent was removed by evaporation and the residue was triturated with petroleum ether. The solid product was collected by filtration and purified by column chromatography eluting with methylene chloride/methanol (95/5) to give 4-(4-chloro-2-fluoro-5-methoxycarbonyloxyanilino)-6-methoxy-7-(3-(4-pyridyl)propoxy)quinazoline (1.2 g, 67%).

$^1$H NMR Spectrum: (DMSOd$_6$) 2.18(m, 2H); 2.84(t, 2H); 3.90(s, 3H); 3.97(s, 3H); 4.2(t, 2H); 7.21(s, 1H); 7.3(d, 2H); 7.72–7.82(m, 3H); 8.41(s, 1H); 8.47(d, 2H); 9.67(s, 1H)

MS - ESI: 513 [MH]$^+$

Example 32

2M Aqueous sodium hydroxide (0.3ml, 6 mmol) was added to a solution of 4-(2-fluoro-5-methoxycarbonyloxy-4-methylanilino)-7-(2-(imidazol-1-yl)ethoxy)-6-methoxyquinazoline (257 mg, 5.5 mmol) in methanol (5 ml) and the mixture stirred for 1 hour at 40° C. Water and 1M hydrochloric acid (0.6 ml) were added and the mixture concentrated to half volume by evaporation. The resulting solid was collected by filtration, dissolved in methylene chloride/methanol and a solution of 7M hydrogen chloride in isopropanol (0.4 ml) was added. The volatiles were removed by evaporation, the solid residue was triturated with ether, collected by filtration and dried under vacuum to give 4-(2-fluoro-5-hydroxy-4-methylanilino)-7-(2-(imidazol-1-yl)ethoxy)-6-methoxyquinazoline hydrochloride (160 mg, 60%).

m.p. 195–220° C.

$^1$HNMR Spectrum: (DMSOd$_6$) 2.16(s, 3H); 4.0(s, 3H); 4.63(t, 2H); 4.76(t, 2H); 6.90(d, 1H); 7.1(d, 1H); 7.44(s, 1H); 7.72(s, 1H); 7.83(s, 1H); 8.31(s, 1H); 8.76(s, 1H); 9.20(s, 1H); 9.7(s, 1H); 11.4(br s, 1H)

MS - ESI: 410 [MH]$^+$

Elemental Analysis: Found C 52.3 H 5.1 N 13.7 C$_{21}$H$_{20}$N$_5$O$_3$F 0.3H$_2$O 1.9HCl Requires C 52.3 H 4.9 N 14.1% 0.22isopropanol The starting material was prepared as follows:

Diethyl azodicarboxylate (160 mg, 1.4 mmol) was added to a solution of 4-(2-fluoro-5-methoxycarbonyloxy-4-methylanilino)-7-hydroxy-6-methoxyquinazoline hydrochloride (261 mg, 0.7 mmol), (prepared as described for the starting material in Example 22), triphenylphosphine (367 mg, 1.4 mmol) and 2-(imidazol-1-yl)ethanol (94 mg, 0.84 mmol), (J. Med. Chem. 1993, 25, 4052–4060), in methylene chloride (5 ml) and the mixture stirred for 1 hour at ambient temperature. Acetic acid (42 mg, 0.7 mmol) was added and the solvent was removed by evaporation. The residue was triturated with ether, the solid collected by filtration, dried under vacuum and purified by chromatography eluting with methylene chloride/methanol (9/1 followed by 8/2) to give 4-(2-fluoro-5-methoxycarbonyloxy-4-methylanilino)-7-(2-(imidazol-1-yl)ethoxy)-6-methoxyquinazoline (250 mg, 76%).

Example 33

A 1M solution of tetrabutylammonium fluoride in THF (560 μl, 0.56 mmol) was added to a suspension of 4-(4-chloro-5-diphenyl-t-butylsilyloxy-2-fluoroanilino)-7-(2-(imidazol-1-yl)ethoxy)-6-methoxyquinazoline (186 mg, 0.28 mmol) in THF (5 ml) and the mixture stirred at 40° C. for 1 hour. Water was added and the organic solvent was removed by evaporation. The resulting precipitate was collected by filtration, washed with water and dried by azeotroping with ethanol. The solid was dissolved in methylene chloride/methanol and a solution of 5M hydrogen chloride in isopropanol (0.5 ml) was added. The volatiles were removed by evaporation and the residue was dissolved in isopropanol (1 ml) and ether was added. The resulting precipitate was collected by filtration, washed with ether and dried under vacuum to give 4-(4-chloro-2-fluoro-5-hydroxyanilino)-7-(2-(imidazol-1-yl)ethoxy)-6-methoxyquinazoline hydrochloride (110 mg, 78%).

$^1$H NMR Spectrum: (DMSOd$_6$) 4.01(s, 3H); 4.63(t, 2H); 4.75(t, 2H); 7.17(d, 1H); 7.46(s, 1H); 7.51(d, 1H); 7.72(s, 1H); 7.83(s, 1H); 8.36(s, 1H); 8.79(s, 1H); 9.21(s, 1H); 10.63(br s, 1H); 11.6(brs, 1H)

MS - ESI: 430 [MH]$^+$

Elemental Analysis: Found C 45.7 H 3.9 N 12.8 C$_{20}$H$_{17}$N$_5$O$_3$ClF 1H$_2$O 2HCl Requires C 45.8 H 4.1 N 13.1% 0.09isopropanol 0.09methylene chloride The starting material was prepared as follows:

A mixture of 7-benzyloxy-4-(4-chloro-2-fluoro-5-hydroxyanilino)-6-methoxyquinazoline (2.35 g, 7 mmol), (prepared as described for Example 29), imidazole (1.2 g, 17.5 mmol), t-butyldiphenylsilylchloride (2.1 g, 7.7 mmol) and 4-(dimethylamino)pyridine (20 mg, 0.16 mmol) in DMF (10 ml) was stirred for 2 hours at ambient temperature. Water (100 ml) and ethyl acetate (30 ml) were added, the resulting precipitate was collected by filtration, washed with water and dried under vacuum to give 7-benzyloxy-4-(4-chloro-5-diphenyl-t-butylsilyloxy-2-fluoroanilino)-6-methoxyquinazoline (2 g, 43%).

$^1$H NMR spectrum (DMSOd$_6$) 1.09(s, 9H); 3.86(s, 3H); 5.25(s, 2H); 7.04(d, 1H); 7.23(s, 1H); 7.32–7.5(m, 11H); 7.58(d, 1H); 7.65–7.72(m, 5H); 8.1(s, 1H); 9.25 (br s, 1H)

MS - ESI: 663 [MH]$^+$

A mixture of 7-benzyloxy-4-(4-chloro-5-diphenyl-t-butylsilyloxy-2-fluoroanilino)-6-methoxyquinazoline (2 g, 3 mmol) and 10% palladium-on-charcoal catalyst (400 mg) in DMF (20 ml), methanol (20 ml) and ethyl acetate (20 ml) was stirred under hydrogen at 1.7 atmospheres pressure for 2 hours. The catalyst was removed by filtration and the solvent removed by evaporation. The residue was purified by column chromatography eluting with methylene chloride/methanol (95/5 followed by 90/1 0). The purified product was triturated with ether, collected by filtration and dried under vacuum to give 4-(4-chloro-5-diphenyl-t-butylsilyloxy-2-fluoroanilino)-7-hydroxy-6-methoxyquinazoline (1.65 g, 95%).

$^1$H NMR spectrum (DMSOd$_6$) 1.09(s, 9H); 3.87(s, 3H); 7.00(s, 1H); 7.07(d, 1H); 7.4–7.5(m, 6H); 7.55(d, 1H); 7.62(s, 1H); 7.7(m, 4H); 8.04(s, 1H); 9.15(br s, 1H); 10.34 (br s, 1H)

Diethyl azodicarboxylate (174 mg, 1 mmol) was added to a solution of 4-(4-chloro-5-diphenyl-t-butylsilyloxy-2-fluoroanilino)-7-hydroxy-6-methoxyquinazoline (288 mg, 0.5 mmol), triphenylphosphine (262 mg, 1 mmol) and 2-(imidazol-1-yl)ethanol (62 mg, 0.55 mmol), (J. Med. Chem. 1993, 25, 4052–4060), in methylene chloride (5 ml) and the mixture stirred for 1 hour at ambient temperature. Acetic acid (30 mg, 0.5 mmol) was added and the volatiles were removed by evaporation. The residue was triturated with ether, the solid collected by filtration and dried under vacuum to give 4-(4-chloro-5-diphenyl-t-butylsilyloxy-2-fluoroanilino)-7-(2-(imidazol-1-yl)ethoxy)-6-methoxyquinazoline (186 mg, 55%).

MS - ESI: 668 [MH]$^+$

Example 34

A suspension of 4-(2-fluoro-5-methoxycarbonyloxy-4-methylanilino)-6-methoxy-7-(2-(4-pyridyl)ethoxy)

quinazoline (300 mg, 0.63 mmol) and 2M aqueous sodium hydroxide (0.38 ml, 0.76 mmol) in methanol (6 ml) was stirred at ambient temperature for 2 hours. Water was added and the mixture adjusted to pH7 with 2M hydrochloric acid. The precipitate was collected by filtration, washed with water, and dried under vacuum. The solid was dissolved in methylene chloride/methanol and a 5M solution of hydrogen chloride in isopropanol (0.5 ml) was added. The mixture was diluted with isopropanol, and the methylene chloride and methanol solvents were removed by evaporation. The resulting precipitate was collected by filtration, washed with methylene chloride and dried under vacuum to give 4-(2-fluoro-5-hydroxy4-methylanilino)-6-methoxy-7-(2-(4-pyridyl)ethoxy)quinazoline hydrochloride (270 mg, 94%).

1H NMR Spectrum: (DMSOd$_6$) 2.16(s, 3H); 3.5(t, 2H); 3.99(s, 3H); 4.57(t, 2H); 6.89(d, 1H); 7.12(d, 1H); 7.44(s, 1H); 7.98(d, 2H); 8.24(s, 1H); 8.78(s, 11H); 8.81(d, 2H); 9.7(br s, 1H); 11.38(brs, 1H)

MS - ESI: 421 [MH]$^+$

Elemental Analysis: Found C 55.5 H 5.3 C$_{23}$H$_{21}$N$_4$O$_3$F 0.3H$_2$O 1HCl Requires C 55.6 H 5.1 0.3isopropanol The starting material was prepared as follow:

Diethyl azodicarboxylate (244 mg, 1.4 mmol) was added to a suspension of 4-(2-fluoro-5-methoxycarbonyloxy-4-methylanilino)-7-hydroxy-6-methoxyquinazoline hydrochloride (261 mg, 0.7 mmol), (prepared as described for the starting material in Example 22), triphenylphosphine (367 mg, 1.4 mmol) and 2-(4-pyridyl)ethanol (104 mg, 0.84 mmol), (Zhur. Obshchei. Khim. 1958, 28, 103–110), in methylene chloride and the mixture stirred for 30 minutes at ambient temperature. The solvent was removed by evaporation. The residue was suspended in ether and the ether then decanted. The resulting crude oil was purified by column chromatography eluting with methylene chloride/methanol (90/10) to give 4-(2-fluoro-5-methoxycarbonyloxy-4-methylanilino)-6-methoxy-7-(2-(4-pyridyl)ethoxy) quinazoline (300 mg, 90%).

$^1$H NMR Spectrum: (DMSOd$_6$) 2.18(s, 3H); 3.16(t, 2H); 3.84(s, 3H); 3.92(s, 3H); 4.44(t, 2H); 7.24(s, 1H); 7.29(d, 1H); 7.40(d, 2H); 7.79(s, 1H); 8.35(s, 1H); 8.49(d, 2H); 9.51(s, 1H)

MS - ESI: 501 [MNa]$^+$

Example 35

Using an analogous procedure to that described in Example 34. 4-(2-fluoro-5-methoxycarbonyloxy-4-methylanilino)-6-methoxy-7-(3-thienylmethoxy) quinazoline (220 mg, 0.47 mmol) was treated with 2M aqueous sodium hydroxide (0.47 ml) to give 4-(2-fluoro-5-hydroxy-4-methylanilino)-6-methoxy-7-(3-thienylmethoxy)quinazoline hydrochloride (180 mg, 86%).

$^1$H NMR Spectrum: (DMSOd$_6$) 2.17(s, 3H); 3.98(s, 3H); 5.34(s, 2H); 6.89(d, 1H); 7.15(d, 1H); 7.27(d, 1H); 7.47(s, 1H); 7.65(dd, 1H); 7.75(s, 1H); 8.18(s, 1H); 8.77(s, 1H); 9.7(br s, 1H)

MS - ESI: 412 [MH]$^+$

Elemental Analysis: Found C 55.5 H 4.5 N 9.0 C$_{21}$H$_{18}$N$_3$O$_3$FS 0.2H$_2$O 1HCl Requires C 55.9 H 4.4 N 9.2% 0.09isopropanol The starting material was prepared as follows:

Using an analogous procedure to that described for the starting material in Example 34, 4-(2-fluoro-5-methoxycarbonyloxy-4-methylanilino)-7-hydroxy-6-methoxyquinazoline hydrochloride (261 mg, 0.77 mmol), (prepared as described for the starting material in Example 22), was combined with 3-thiophenemethanol (96 mg, 0.84 mmol) to give, after purification by flash chromatography eluting with methylene chloride/methanol (98/2), 4-(2-fluoro-5-methoxycarbonyloxy-4-methylanilino)-6-methoxy-7-(3-thienylmethoxy)quinazoline (220 mg, 67%).

$^1$H NMR Spectrum: (DMSOd$_6$) 2.18(s, 3H); 3.85(s, 3H); 3.93(s, 3H); 5.27(s, 2H); 7.23(d, 1H); 7.30(d, 1H); 7.32(s, 1H); 7.40(d, 1H); 7.59(dd, 1H); 7.66(s, 1H); 7.81(s, 1H); 8.35(s, 1H); 9.53(s, 1H)

MS - ESI: 492 [MNa]$^+$

Example 36

A mixture of 4-(2-fluoro-5-methoxycarbonyloxy-4-methylanilino)-7-hydroxy-6-methoxyquinazoline hydrochloride (187 mg, 0.75 mmol), (prepared as described for the starting material in Example 22), 4-bromomethylbenzonitrile (147 mg, 0.75 mmol) and potassium carbonate (173 mg, 1.25 mmol) in DMF (5 ml) was heated at 50° C. for 1 hour. Methanol (5 ml) and potassium carbonate (138 mg, 1 mmol) were added and the mixture stirred at 65° C. for 2 hours. The solvent was removed by evaporation, water was added to the residue and the mixture adjusted to pH7 with 2M hydrochloric acid. The resulting precipitate was collected by filtration, washed with water and dried under vacuum. The solid was purified by column chromatography eluting with methylene chloride/methanol (95/5). The purified product was triturated with ether, collected by filtration and dried. The solid was dissolved in methylene chloride/isopropanol and a 5M solution of hydrogen chloride in isopropanol (0.5 ml) was added. The mixture was concentrated by evaporation and the resulting precipitate collected by filtration, washed with methylene chloride and dried under vacuum to give 7-(4-cyanobenzyloxy)-4-(2-fluoro-5-hydroxy-4-methylanilino)-6-methoxyquinazoline hydrochloride (60 mg, 25%).

m.p. 265–270° C.

$^1$H NMR Spectrum: (DMSOd$_6$) 2.17(s, 3H); 4.02(s, 3H); 5.47(s, 2H); 6.89(d, 1H); 7.1 1(d, 1H); 7.38(s, 1H); 7.71(d, 2H); 7.93(d, 2H); 8.23(s, 1H); 8.75(s, 1H); 9.67(s, 1H); 11.24(br s, 1H)

MS - ESI: 431 [MH]$^+$

Elemental Analysis: Found C 61.2 H 4.5 N 11.7 C$_{24}$H$_{19}$N$_4$O$_3$F 0.1H$_2$O 1HCl Requires C 61.5 H 4.3 N 12.0%

Example 37

Diethyl azodicarboxylate (315 μl, 2 mmol) was added dropwise to a solution of 4-(4-chloro-2-fluoroanilino)-7-hydroxy-6-methoxyquinazoline (319.5 mg, 1 mmol), (prepared as described for the starting material in Example 24), triphenylphosphine (524 mg, 2 mmol) and 2-(4-pyridyl) ethanol (160 mg, 1.25 mmol), (Zhur. Obshchei. Khim. 1958, 28, 103–110), in methylene chloride (7 ml). The mixture was stirred for 1 hour at ambient temperature and the solvent was removed by evaporation. The residue was triturated with ether, the solid collected by filtration and purified by column chromatography eluting with methylene chloride/ acetonitrile/methanol (85/10/5). The purified solid product was dissolved in a mixture of methylene chloride (50 ml) and methanol (50 ml) and 5M hydrochloric acid in isopropanol (0.5 ml) was added. After diluting with isopropanol (20 ml), the mixture was concentrated by evaporation. The precipitated solid was collected by filtration and dried under vacuum to give 4-(4-chloro-2-fluoroanilino)-6-methoxy-7-(2-(4-pyridyl)ethoxy)quinazoline hydrochloride (125 mg, 25%).

m.p. 189–191° C.

$^1$H NMR Spectrum: (DMSOd$_6$; CF$_3$COOD) 3.55(t, 2H); 3.99(s, 3H); 4.64(t, 2H); 7.46(s, 1H); 7.48(d, 1H); 7.62(t, 1H); 7.67(dd, 1H); 8.16(d, 2H); 8.17(s, 1H); 8.88(s, 1H); 8.94(d, 1H)

MS - ESI: 425 [MH]$^+$

Elemental Analysis: Found C 52.0 H 4.3 N 11.1 C$_{22}$H18N$_4$O$_2$ClF 0.5H$_2$O 1.95HCl Requires C 52.3 H 4.2 N 11.1%

Example 38

3-(Chloromethyl)pyridine hydrochloride (328 mg, 2 mmol) was added to a mixture of 4-(4-chloro-2-fluoroanilino)-7-hydroxy-6-methoxyquinazoline (319.5 mg, 1 mmol), (prepared as described for the starting material in Example 24), potassium carbonate (442 mg, 3.2 mmol) and potassium iodide (33 mg, 0.2 mmol) in DMF (25 ml) at ambient temperature and the reaction mixture then heated at 80° C. for 2.5 hours. The mixture was allowed to cool and the volatiles were removed by evaporation. The residue was dissolved in a mixture of ethyl acetate (19 ml) and methanol (1 ml) and the insolubles removed by filtration. The solvent was removed from the filtrate by evaporation and the residue was purified by column chromatography eluting with methylene chloride/acetonitrile/methanol (50/45/5). The purified product was dissolved in hot methylene chloride and saturated ethereal hydrogen chloride was added. The mixture was concentrated to half volume by evaporation, the resulting precipitate was collected by filtration and dried under vacuum at 70° C. to give 4-(4- chloro-2-fluoroanilino)-6-methoxy-7-((3-pyridyl)methoxy)quinazoline hydrochloride (103 mg, 25%).

m.p. 216–221° C.

$^1$H NMR Spectrum: (DMSOd$_6$) 4.03(s, 3H); 5.48(s, 2H); 7.47(d, 1H); 7.54(s, 1H); 7.65(t, 1H); 7.7–7.8(m, 2H); 8.25(d, 1H); 8.35(s, 1H); 8.75(d, 1H); 8.84(s, 1H); 8.90(s, 1H); 11.65(br s, 1H)

MS - ESI: 411 [MH]$^+$

Elemental Analysis: Found C 51.9 H 4.2 N 11.4 C$_{21}$H$_{16}$N$_4$O$_2$ClF 0.8H$_2$O 1.6HCl Requires C 52.2 H 4.0 N 11.6%

Example 39

Using an analogous procedure to that described in Example 38, 4-(4-chloro-2-fluoroanilino)-7-hydroxy-6-methoxyquinazoline (319.5 mg, 1 mmol), (prepared as described for the starting material in Example 24), was reacted with 2-(chloromethyl)pyridine hydrochloride (310 mg, 1.9 mmol) to give 4-(4-chloro-2-fluoroanilino)-6-methoxy-7-((2-pyridyl)methoxy)quinazoline (146 mg, 33%).

m.p. 215–218° C.

$^1$H NMR Spectrum: (DMSOd$_6$) 3.98(s, 3H); 5.4(s, 2H); 7.3(s, 1H); 7.32–7.42(m, 2H); 7.52–7.62(m, 3H); 7.85(s, 1H); 7.90(t, 1H); 8.35(s, 1H); 8.65(d, 1H); 9.6(s, 1H)

MS - ESI: 411 [MH]$^+$

Elemental Analysis: Found C 59.7 H 3.9 N 13.1 C$_{21}$H$_{16}$N$_4$O$_2$ClF 0.5H$_2$O Requires C 60.1 H 4.1 N 13.3%

Example 40

Diethyl azodicarboxylate (128 μl, 1.5 mmol) was added dropwise to a solution of 4-(4-chloro-2-fluoroanilino)-7-hydroxy-6-methoxyquinazoline (250 mg, 0.78 mmol), (prepared as described for the starting material in Example 24), triphenylphosphine (410 mg, 1.5 mmol) and 2-(1-methylimidazol-2-yl)ethanol (147 mg, 1.15 mmol), (EP 0675112 A1), in methylene chloride (4 ml) and the mixture was stirred for 30 minutes at ambient temperature. Further triphenylphosphine (143 mg, 0.52 mmol) and diethyl azodicarboxylate (85 μl, 1 mmol) were added and the mixture stirred for 1 hour at ambient temperature. The solid product was collected by filtration and washed with methylene chloride. The solid was dissolved in a mixture of methylene chloride (25 ml) and methanol (25 ml), and a solution of 2.9M ethereal hydrogen chloride (2 ml) was added. The mixture was concentrated by evaporation and the resulting precipitate was collected by filtration, washed with ether and dried under vacuum to give 4-(4-chloro-2-fluoroanilino)-6-methoxy-7-(2-(1-methylimidazol-2-yl)ethoxy)quinazoline hydrochloride (133 mg, 34%).

m.p. 224–229° C.

$^1$H NMR Spectrum: (DMSOd$_6$) 3.62(t, 2H); 3.94(s, 3H); 4.0(s, 3H); 4.59(t, 2H); 7.43(d, 1H); 7.46(s, 1H); 7.6(t, 1H); 7.6–7.7(m, 3H); 8.41(s, 1H); 8.78(s, 1H); 11.75(br s, 1H)

MS - ESI: 428 [MH]$^+$

Elemental Analysis: Found C 48.8 H 4.4 N 13.4 C$_{21}$H$_{19}$N$_5$O$_2$ClF 1H$_2$O 2HCl Requires C 48.6 H 4.5 N 13.5%

Example 41

A mixture of 4-(4-chloro-2-fluoroanilino)-7-hydroxy-6-methoxyquinazoline (319.5 mg, 1 mmol), (prepared as described for the starting material in Example 24), potassium carbonate (414 mg, 3 mmol), potassium iodide (16 mg, 0.1 mmol) and 4-chloromethylpyrimidine (257 mg, 2 mmol) in DMF (20 ml) was heated at 80° C. for 2 hours. The solvent was removed by evaporation and the residue was triturated with water. The solid was collected by filtration and dried under vaccum. The solid was purified by column chromatography eluting with methylene chloride/methanol (95/5). The purified white solid was suspended in methanol (25 ml) and a solution of 7.5M hydrogen chloride in methanol (20 ml) was added. The resulting solid product was collected by filtration, washed with methanol and then pentane and dried under vacuum to give 4-(4-chloro-2-fluoroanilino)-6-methoxy-7-((pyrimidin-4-yl)methoxy) quinazoline hydrochloride (172 mg, 42%).

m.p. 237–239° C.

$^1$H NMR Spectrum: (DMSOd$_6$; CF$_3$COOD) 4.07(s, 3H); 5.53(s, 2H); 7.40(s, 1H); 7.46(dd, 1H); 7.65(t, 1H); 7.68–7.72(m, 2H); 8.26(s, 1H); 8.85(s, 1H); 8.91(d, 1H); 9.25(s, 1H)

MS - ESI: 412 [MH]$^+$

Elemental Analysis: Found C 49.5 H 3.6 N 14.1 C$_{20}$H$_{15}$N$_5$O$_2$ClF 0.5H$_2$O 1.85HCl Requires C 49.2 H 3.7 N 14.3%

The starting material was prepared as follows:

A solution of 4-methylpyrimidine (2 g, 21.2 mmol), N-chlorosuccinimide (4.26 g, 31.9 mmol) and benzoyl peroxide (500 mg, 2.1 mmol) in carbon tetrachloride (100 ml) was heated at 80° C. for 2 hours. The mixture was allowed to cool, the insolubles were removed by filtration and the solvent was removed from the filtrate by evaporation. The residue was purified by column chromatography eluting with methylene chloride to give 4-chloromethylpyrimidine (257 mg, 10%).

$^1$H NMR Spectrum: (DMSOd$_6$) 4.81(s, 2H); 7.70(d, 1H); 8.88(d,1 H); 9.21(s, 1H)

Example 42

2M Aqueous sodium hydroxide solution (900 μl) was added to a solution of 4-(3-acetoxy-4-methylanilino)-6- methoxy-7-((1-methylbenzimidazol-2-yl)methoxy)quinazoline (290 mg, 0.6 mmol) in methanol (15 ml) and methylene chloride (12 ml) and the mixture stirred for 25 minutes at ambient temperature. The solvent was removed by evaporation and the residue was partitioned between ethyl acetate and water. The organic layer was separated, washed with water and brine, dried (MgSO$_4$) and the solvent removed by evaporation. The solid residue was purified by column chromatography eluting with methylene chloride/methanol (97/3 and 95/5). The purified white solid was suspended in methanol (20 ml) and a solution of 7.5M hydrochloric acid in methanol (2 equivalents) was added. The solid was collected by filtration, washed with methanol and then pentane and dried under vacuum at 50° C. to give 4-(3-hydroxy-4-methylanilino)-6-methoxy-7-((1-methylbenzimidazol-2-yl)methoxy)quinazoline hydrochloride (106 mg, 37%).

$^1$H NMR Spectrum: (DMSOd$_6$; CF$_3$COOD) 2.17(s, 3H); 4.04(s, 3H); 4.15(s, 3H); 6.01(s, 2H); 7.0(dd, 1H); 7.11 (d, 1H); 7.18(d, 1H); 7.6–7.75(m, 3H); 7.89(d, 1H); 8.05(d, 1H); 8.27(s, 1H); 8.86(s, 1H)

MS - ESI: 469 [MNa]$^+$

The starting material was prepared as follows:

A solution of 1-methylbenzimidazole (2.5 g, 19 mmol), (J. Chem. Soc. 1929, 2820–2828), and paraformaldehyde (2 g) was heated at 165° C. for 30 minutes. Further paraformaldehyde (1 g) was added and heating continued for 2 hours. The mixture was allowed to cool and was purified by column chromatography eluting with methylene chloride, followed by methylene chloride/methanol (95/5) to give 2-hydroxymethyl-1-methylbenzimidazole (1.34 g, 45%).

$^1$H NMR Spectrum: (DMSOd$_6$) 3.84(s, 3H); 4.73(s, 2H); 5.57(br s, 1H); 7.19(t, 1H); 7.25(t, 1H); 7.54(d, 1H); 7.60(d, 1H)

MS - ESI: 185 [MNa]$^+$

A solution of 2-hydroxymethyl-1-methylbenzimidazole (1.1 g, 6.7 mmol) in thionyl chloride (10 ml) was stirred at ambient temperature for 15 minutes and then heated at reflux for 15 minutes. The volatiles were removed by evaporation and the residue purified by column chromatography eluting with methylene chloride/methanol (95/5) to give 2-chloromethyl-1-methylbenzimidazole (506 mg, 36%).

$^1$H NMR Spectrum: (DMSOd$_6$; CF$_3$COOD) 4.07(s, 3H); 5.38(s, 2H); 7.6–7.7(m, 2H); 7.9(d, 1H); 8.05(dd, 1H)

MS-ESI: 181 [MH]$^+$

A mixture of 4-(3-acetoxy4-methylanilino)-7-hydroxy-6-methoxyquinazoline hydrochloride (240 mg, 0.64 mmol), (prepared as described for the starting material in Example 1), potassium carbonate (310 mg, 2.25 mmol), potassium iodide (10 mg, 0.064 mmol) and 2-chloromethyl-1-methylbenzimidazole (153 mg, 0.7 mmol) in DMF (12 ml) was heated at 65° C. for 3 hours. Further 2-chloromethyl-1-methylbenzimidazole (90 mg, 0.41 mmol) and potassium carbonate (165 mg, 1.2 mmol) were added and heating continued for 2 hours. The solvent was removed by evaporation and the residue was partitioned between ethyl acetate and water. The organic layer was separated, washed with water and brine, dried (MgSO$_4$) and the solvent removed by evaporation. The residue was triturated with water and the solid product collected by filtration, washed with ether and dried under vacuum to give 4-(3-acetoxy-4-methylanilino)-6-methoxy-7-((1-methylbenzoimidazol-2-yl)methoxy)quinazoline (292 mg, 95%).

MS - ESI: 506 [MNa]$^+$

Example 43

2M Aqueous sodium hydroxide solution (700 μl, 1.4 mmol) was added to a suspension of 7-((2-chloro-6-methyl-4-pyridyl)methoxy)-4-(2-fluoro-5-methoxycarbonyloxy-4-methylanilino)-6-methoxyquinazoline (360 mg, 0.7 mmol) in methanol (10 ml) cooled at 5° C. and the mixture was then stirred for 30 minutes at ambient temperature. The solvent was removed by evaporation, the residue diluted with water (10 ml) and the mixture adjusted to pH7 with 1M hydrochloric acid. The resulting solid was collected by filtration, washed with water and ether, and dried under vacuum. This solid was dissolved in methanol (5 ml) and a 7M solution of hydrogen chloride in methanol (3 ml) was added. The precipitate was collected by filtration, washed with methanol and dried under vacuum to give 7-((2-chloro-6-methyl-4-pyridyl)methoxy)-4-(2-fluoro-5-hydroxy4-methylanilino)-6-methoxyquinazoline hydrochloride (273 mg, 74%).

$^1$H NMR Spectrum: (DMSOd$_6$; CF$_3$COOD) 2.18(s, 3H); 2.50(s, 3H); 4.04(s, 3H); 5.42(s, 2H); 6.9(d, 1H); 7.12(d, 1H); 7.35(s, 1H); 7.38(s, 1H); 7.42(s, 1H); 8.21(s, 1H); 8.81(s, 1H)

MS - ESI: 455 [MH]$^+$

Elemental Analysis: Found C 49.8 H 4.8 N 10.0
C$_{23}$H$_{20}$N$_4$O$_3$ClF 1.5H$_2$O 1.9HCl Requires C 50.1 H 4.6 N 10.2%

The starting material was prepared as follows:

A solution of 2-chloro-6-methyl-4-pyridinecarboxylic acid (2 g, 12 mmol) in ethanol (100 ml) and concentrated sulphuric acid (10 ml) was heated at reflux for 2 hours. The volatiles were removed by evaporation and the residue was dissolved in methylene chloride. The solution was washed with a saturated aqueous sodium hydrogen carbonate solution and brine, dried (MgSO$_4$) and the solvent removed by evaporation. The residue was purified by column chromatography eluting with ethyl acetate/petroleum ether (1/9) to give ethyl 2-chloro-6-methyl-4-pyridinecarboxylate (2 g, 86%).

$^1$H NMR Spectrum: (CDCl$_3$) 1.41(t, 3H); 2.6(s, 3H); 4.40(q, 2H); 7.63(s, 1H); 7.69(s, 1H)

MS - ESI: 200 [MH]$^+$

Elemental Analysis: Found C 54.4 H 5.3 N 7.0
C$_9$H$_{10}$NO$_2$Cl Requires C 54.1 H 5.0 N 7.0%

Lithium aluminium hydride (350 mg, 9.26 mmol) was added in portions to a solution of ethyl 2-chloro-6-methyl-4-pyridinecarboxylate (1.85 g, 9.26 mmol) in THF (40 ml) cooled at 0° C. The mixture was stirred for 15 minutes at 0° C. and acetic acid (2 ml) was added. The mixture was partitioned between ethyl acetate and water and the aqueous layer was adjusted to pH7.5 with 5 % aqueous sodium hydrogen carbonate solution. The organic layer was separated, washed with water and brine, dried (MgSO$_4$) and the solvent removed by evaporation. The residue was purified by column chromatography eluting with ethyl acetate/petroleum ether (35/65) to give 2-chloro-4-hydroxymethyl-6-methylpyridine (1.28 g, 88%).

$^1$H NMR Spectrum: (CDCl$_3$) 1.92(t, 1H); 2.53(s, 3H); 4.70(d, 2H); 7.06(s, 1H); 7.16(s, 1H)

MS - ESI: 157 [MH]$^+$

Elemental Analysis: Found C 53.1 H 5.3 N 8.7
C$_7$H$_8$NOCl Requires C 53.3 H 5.1 N 8.9%

Diethyl azodicarboxylate (296 μl, 1.88 mmol) was added dropwise to a solution of 4-(2-fluoro-5-methoxycarbonyloxy-4-methylanilino)-7-hydroxy-6-methoxyquinazoline hydrochloride (350 mg, 0.94 mmol), (prepared as described for the starting material in Example 22), triphenylphosphine (492 mg, 1.88 mmol) and 2-chloro-4-hydroxymethyl-6-methylpyridine (178 mg, 1.12 mmol) in methylene chloride (30 ml) and the mixture stirred for 30 minutes at ambient temperature. The solvent was removed by evaporation and the residue was purified by column chromatography eluting with ethyl acetate/methylene chloride (75/25). The purified product was triturated with ether, the solid collected by filtration, washed with ether and dried under vacuum to give 7-((2-chloro-6-methyl-4-pyridyl) methoxy)-4-(2-fluoro-5-methoxycarbonyloxy-4-methylanilino)-6-methoxyquinazoline (373 mg, 78%).

$^1$H NMR Spectrum: (DMSOd$_6$) 2.15(s, 3H); 2.5(s, 3H); 3.85(s, 3H); 3.98(s, 3H); 5.35(s, 2H); 7.25(s, 1H); 7.3(d, 1H); 7.35(s, 1H); 7.4(m, 2H); 7.85(s, 1H); 8.35(s, 1H); 9.58(s, 1H)

MS - ESI: 513 [MH]$^+$

Example 44

A mixture of 4-(4-chloro-2-fluorophenoxy)-7-hydroxy-6-methoxyquinazoline (112 mg, 0.35 mmol), potassium carbonate (138 mg, 1 mmol) and 4-(chloromethyl)pyridine hydrochloride (59 mg, 0.36 mmol) in DMF (2 ml) was heated at 80° C. for 1 hour. The mixture was allowed to cool and partitioned between ethyl acetate and water. The organic layer was separated, washed with water and brine, dried (MgSO$_4$) and the solvent removed by evaporation. The residue was purified by column chromatography eluting with methylene chloride/methanol (95/5) to give 4-(4-chloro-2-fluorophenoxy)-6-methoxy-7-((4-pyridyl)methoxy)quinazoline (115 mg, 80%).

m.p. 197–198° C.

$^1$H NMR Spectrum: (DMSOd$_6$) 4.03(s, 3H); 5.46(s, 2H); 7.45(d, 1H); 7.49(s, 1H); 7.5(d, 2H); 7.58(t, 1H); 7.62(s, 1H); 7.72(dd, 1H); 8.58(s, 1H); 8.65(d, 2H)

MS - ESI: 412 [MH]$^+$

Elemental Analysis: Found C 59.5 H 3.9 N 9.6 C$_{21}$H$_{15}$N$_3$O$_3$ClF 0.8H$_2$O Requires C 59.2 H 3.9 N 9.9%

The starting material was prepared as follows:

4-Chloro-2-fluoro-phenol (264 mg, 1.8 mmol) was added to a solution of 7-benzyloxy-4-chloro-6-methoxyquinazoline hydrochloride (506 mg, 1.5 mmol), (prepared as described for the starting material in Example 1), in pyridine (8 ml) and the mixture heated at reflux for 45 minutes. The solvent was removed by evaporation and the residue partitioned between ethyl acetate and water. The organic layer was washed with 0.1M hydrochloric acid, water and brine, dried (MgSO$_4$) and the solvent removed by evaporation. The solid residue was triturated with petroleum ether and the crude product collected by filtration and purified by flash chromatography eluting with methylene chloride/ether (9/1) to give 7-benzyloxy-4-(4-chloro-2-fluorophenoxy)-6-methoxyquinazoline (474 mg, 77%) as a cream solid.

m.p. 179–180° C.

$^1$H NMR Spectrum: (DMSOd$_6$) 3.99(s, 3H); 5.36(s, 3H); 7.35–7.5(m, 4H); 7.55–7.65(m, 5H); 7.72(d, 1H); 8.6(s, 1H)

MS-ESI:411 [MH]$^+$

Elemental analysis: Found C 63.4 H 4.1 N 6.8 C$_{22}$H$_{16}$ClFN$_2$O$_3$ 0.06H$_2$O 0.05CH$_2$Cl$_2$ Requires C 63.6 H 3.9 N 6.7%

A solution of 7-benzyloxy-4-(4-chloro-2-fluorophenoxy)-6-methoxyquinazoline (451 mg, 1.1 mmol) in TFA (4.5 ml) was heated at reflux for 3 hours. The mixture was diluted with toluene and the volatiles removed by evaporation. The residue was triturated with methylene chloride, collected by filtration, washed with ether and dried under vacuum to give 4-(4-chloro-2-fluorophenoxy)-7-hydroxy-6-methoxyquinazoline (320 mg, 90%).

$^1$H NMR Spectrum: (DMSOd$_6$) 4.0(s, 3H); 7.27(s, 1H); 7.43(dd, 1H); 7.56(t, 1H); 7.57(s, 1H); 7.72(dd, 1H); 8.5(s, 1H)

MS - ESI: 321 [MH]$^+$

Example 45

A mixture of 4-(4-chloro-2-fluoroanilino)-7-hydroxy-6-methoxyquinazoline (320 mg, 1 mmol), (prepared as described for the starting material in Example 24), potassium carbonate (414 mg, 3 mmol), potassium iodide (40 mg) and 4-(chloromethyl)pyridine hydrochloride (250 mg, 1.5 mmol) in DMF (15 ml) was heated at 60° C. for 2 hours. The mixture was allowed to cool and partitioned between ethyl acetate and water. The organic layer was separated, washed with water and brine, dried (MgSO$_4$) and the solvent removed by evaporation. The residue was suspended in ethanol (20 ml) and concentrated hydrochloric acid (0.5 ml) was added. The volatiles were removed by evaporation and the solid residue was azeotroped with toluene. The solid product was recrystallised from isopropanol to give 4-(4-chloro-2-fluoroanilino)-6-methoxy-7-((4-pyridyl)methoxy)quinazoline hydrochloride (335 mg, 70%).

$^1$H NMR Spectrum: (DMSOd$_6$) 4.1(s, 3H); 5.69(s, 2H); 7.46(dd, 1H); 7.52(s, 1H); 7.62(t, 1H); 7.69(dd, 1H); 8.03(d, 2H); 8.55(s, 1H); 8.83(s, 1H); 8.93(d, 2H)

MS - ESI: 411 [MH]$^+$

Elemental Analysis: Found C 51.0 H 3.9 N 11.2 C$_{21}$H$_{16}$N$_4$O$_2$ClF 0.5H$_2$O 1.95HCl Requires C 51.4 H 3.9 N 11.4%

Example 46

Diethyl azodicarboxylate (261 mg, 1.5 mmol) was added dropwise to a suspension of 4-(4-chloro-2-fluoroanilino)-7-hydroxy-6-methoxyquinazoline (160 mg, 0.5 mmol), (prepared as described for the starting material in Example 24), triphenylphosphine (393 mg, 1.5 mmol) and 2-(N-(2, 6-dimethyl-4-pyridyl)-N-methylamino)ethanol (125 mg, 0.7 mmol) in methylene chloride (5 ml) and the mixture stirred for 2 hours at ambient temperature. Methanol (10 drops) was added and the mixture was poured on to a column of neutral aluminium oxide and the product was separated by elution with methylene chloride/acetonitrile/methanol (60/35/35). The purified solid product was triturated with ether and collected by filtration. The solid was dissolved in methylene chloride/methanol and a solution of 3M ethereal hydrogen chloride (1 ml) was added. The solid was collected by filtration, washed with ether and dried under vacuum to give 4-(4-chloro-2-fluoroanilino)-7-(2-(N-(2,6-dimethyl-4-pyridyl)-N-methylamino)ethoxy)-6-methoxyquinazoline (170 mg, 61%).

m.p. 208–212° C.

$^1$H NMR Spectrum: (DMSOd$_6$; CF$_3$COOD) 2.52(s, 6H); 3.26(s, 3H); 3.98(s, 3H); 4.12(t, 2H); 4.46(t, 2H); 6.8(br s, 1H); 7.1(br s, 1H); 7.38(s, 1H); 7.46(dd, 1H); 7.62(t, 1H); 7.67(dd, 1H); 8.18(s, 1H); 8.89(s, 1H)

MS - ESI: 482 [MH]$^+$

Elemental Analysis: Found C 52.2 H 5.2 N 12.2 C$_{25}$H$_{25}$N$_5$O$_2$ClF 1H$_2$O 2HCl Requires C 52.4 H 5.1 N 12.2%

The starting material was prepared as follows:

A solution of 4-chloro-2,6-dimethylpyridine (849 mg, 6 mmol), (J. Het. Chem. 1990, 1841), in 2-(methylamino) ethanol (1.35 g, 18 mmol) and 3M ethereal hydrogen chloride (3 drops) was heated at 140° C. for 1 hour. The reaction mixture was allowed to cool and was diluted with water. The insolubles were removed by filtration and the aqueous filtrate was poured onto a suspension of magnesium sulphate (50 g) in ethyl acetate (100 ml). The insolubles were removed by filtration and the filtrate dried (MgSO$_4$) and the solvent removed by evaporation. The solid residue was triturated with ether, collected by filtration and dried under vacuum at 50° C. to give 2-(N-(2,6-dimethyl-4-pyridyl)-N-methylamino)ethanol (960 mg, 90%).

m.p. 139–144° C.

$^1$H NMR Spectrum: (CDCl$_3$) 2.4(s, 6H); 3.0(s, 3H); 3.51 (t, 2H); 3.81 (t, 2H); 6.26(s, 2H)

MS - ESI: 181 [MH]$^+$

Example 47

Diethyl azodicarboxylate (261 mg, 1.5 mmol) was added dropwise to a suspension of of 4-(4-chloro-2-fluoroanilino)-7-hydroxy-6-methoxyquinazoline (160 mg, 0.5 mmol), (prepared as described for the starting material in Example 24), triphenylphosphine (393 mg, 1.5 mmol) and 2-(N-(4-pyridyl)amino)ethanol (97 mg, 0.7 mmol) in methylene chloride (8 ml) and the mixture stirred for 2 hours at ambient temperature. The mixture was diluted with ethyl acetate (5 ml), the solid product was collected by filtration and purified by chromatography on an aluminium oxide column eluting with methylene chloride/acetonitrile/methanol (60/35/5). The purified solid was triturated with ether and collected by filtration. The solid was dissolved in a mixture of methylene chloride/methanol and 3M ethereal hydrogen chloride (0.5 ml) was added. The volatiles were removed by evaporation, the solid residue was suspended in ether, collected by filtration, washed with ether and dried under vacuum to give 4-(4-chloro-2-fluoroanilino)-6-methoxy-7-(2-(N-(4-pyridyl)amino)ethoxy)quinazoline hydrochloride (95 mg, 37%).

$^1$H NMR Spectrum: (DMSOd$_6$; CF$_3$COOD) 3.87(t, 2H); 4.00(s, 3H); 4.43(t, 2H); 6.97(dd, 1H); 7.15(dd, 1H); 7.43(s, 1H); 7.46(dd, 1H); 7.66(t, 1H); 7.68(dd, 1H); 8.12(d, 1H); 8.21(s, 1H); 8.34(d, 1H); 8.89(s, 1H)

MS - ESI: 440 [MH]$^+$

Elemental Analysis: Found C 50.0 H 4.3 N 13.2
C$_{22}$H$_{19}$N$_5$O$_2$ClF 0.8H$_2$O 2HCl Requires C 50.0 H 4.3 N 13.2%

The starting material was prepared as follows:

Using a procedure analogous to that described for the starting material in Example 46, 4-chloropyridine (3 g, 20 mmol) was treated with aminoethanol (6.1 g, 0.1 mol) to give 2-(N-(4-pyridyl))aminoethanol (400 mg, 25%).

m.p. 110–111° C.

$^1$H NMR Spectrum: (CDCl$_3$) 3.3(m, 2H); 3.81(m, 2H); 4.94(br s, 1H); 6.44(d, 2H); 8.13(d, 2H)

MS - ESI: 138 [MH]$^+$

Example 48

Using a procedure analogous to that described in Example 47, 3-(N-methyl-N-(4-pyridyl)amino)propanol (116 mg, 0.7 mmol) was treated with 4-(4-chloro-2-fluoroanilino)-7-hydroxy-6-methoxyquinazoline (160 mg, 0.5 mmol), (prepared as described for the starting material in Example 24), to give 4-(4-chloro-2-fluoroanilino)-6-methoxy-7-(3-(N-methyl-N-(4-pyridyl)amino)propoxy)quinazoline hydrochloride (150 mg, 55%).

m.p. 243–248° C.

1H NMR Spectrum: (DMSOd$_6$; CD$_3$COOD) 2.2(t, 2H); 3.21(t, 3H); 3.82(t, 2H); 4.0(s, 3H); 4.31(t, 2H); 6.95(br s, 1H); 7.2(br s, 1H); 7.39(s, 1H); 7.46(dd, 1H); 7.62(t, 1H); 7.68(dd, 1H); 8.2(s, 1H); 8.3(br s, 2H); 8.87(s, 1H)

MS - ESI: 468 [MH]$^+$

Elemental Analysis: Found C 51.4 H 5.1 N 12.9
C$_{24}$H$_{23}$N$_5$O$_2$ClF 1.2H$_2$O 1.95HCl Requires C 51.4 H 4.9 N 12.5%

The starting material was prepared as follows:

Using a procedure analogous to that described for the starting material in Example 46, 4-chloropyridine (885 mg, 59 mmol) and 3-(methylamino)propanol (2.1 g, 0.23 mmol), (Tetrahedron Lett. 1994, 35, 1545–1548), were heated for 8 hours to give 3-(N-methyl-N-(4-pyridyl)amino)propanol (979 mg, 61%).

$^1$H NMR Spectrum: (CDCl$_3$; CD$_3$COOD) 1.8–1.9(m, 2H); 3.16(s, 3H); 3.6–3.75(m, 4H); 6.8(br s, 2H); 8.30(d, 2H)

MS - ESI: 166 [MH]$^+$

Example 49

Diethyl azodicarboxylate (261 mg, 1.5 mmol) was added dropwise to a suspension of 4-(4-chloro-2-fluoroanilino)-7-hydroxy-6-methoxyquinazoline (160 mg, 0.5 mmol), (prepared as described for the starting material in Example 24), triphenylphosphine (393 mg, 1.5 mmol) and 1-(2-hydroxyethyl)-2-methylimidazole (88 mg, 0.7 mmol), (Chem.Abs. 1964, 60, 2949), in methylene chloride (8 ml) and the mixture stirred for 2 hours at ambient temperature. The mixture was diluted with ether (8 ml) and the solid product was collected by filtration. The solid was dissolved in methylene chloride/methanol and a solution of 3M ethereal hydrogen chloride (0.5 ml) was added. The resulting precipitate was collected by filtration, washed with ether and dried under vacuum to give 4-(4-chloro-2-fluoroanilino)-6-methoxy-7-(2-(2-methylimidazol-1-yl)ethoxy)quinazoline hydrochloride (180 mg, 72%).

$^1$H NMR Spectrum: (DMSOd$_6$; CF$_3$COOD) 2.79(s, 3H); 4.02(s, 3H); 4.59(t, 2H); 4.72(t, 2H); 7.40(s, 1H); 7.45(d, 1H); 7.60(s, 1H); 7.62(t, 1H); 7.67(dd, 1H); 7.71(s, 1H); 8.23(s, 1H); 8.89(s, 1H)

MS - ESI: 428 [MH]$^+$

Elemental Analysis: Found C 47.9 H 4.7 N 13.3
C$_{21}$H$_{19}$N$_5$O$_2$ClF 1.4H$_2$O 2.1HCl Requires C 47.6 H 4.6 N 13.2%

Example 50

Diethyl azodicarboxylate (295 μl, 1.8 mmol) was added dropwise to a solution of 1-(3-hydroxypropyl)imidazole (102 mg, 0.81 mmol), (EP 0060696 A1), 4-(4-chloro-2-fluoroanilino)-7-hydroxy-6-methoxyquinazoline (200 mg, 0.62 mmol), (prepared as described for the starting material in Example 24), and triphenylphosphine (492 mg, 1.8 mmol) in methylene chloride (4 ml) and the mixture stirred for 2 hours at ambient temperature. The solvent was removed by evaporation and the residue was purified by column chromatography eluting with methylene chloride/acetonitrile/methanol (60/35/5). The purified solid was dissolved in methylene chloride/methanol and 5M ethereal hydrogen chloride (2 ml) was added. The volatiles were removed by evaporation, the solid residue was suspended in ether, collected by filtration, washed with ether and dried under vacuum to give 4-(4-chloro-2-fluoroanilino)-7-(3-(imidazol-1-yl)propoxy)-6-methoxyquinazoline hydrochloride (114 mg, 36%).

$^1$H NMR Spectrum: (DMSOd$_6$; CF$_3$COOD) 2.5(m, 2H); 3.99(s, 3H); 4.32(t, 2H); 4.45(t, 2H); 7.39(s, 1H); 7.45(dd, 1H); 7.61(t, 1H); 7.66(dd, 1H); 7.71(s, 1H); 7.84(s, 1H); 8.19(s, 1H); 8.77(s, 1H); 9.20(s, 1H)

MS - ESI: 428 [MH]$^+$

Elemental Analysis: Found C 48.2 H 4.5 N 13.2 $C_{21}H_{19}N_5O_2ClF$ 1.2$H_2O$ 1.9HCl Requires C 48.6 H 4.5 N 13.5%

Example 51

7-(2-Bromoethoxy)-4-(4-chloro-2-fluoroanilino)-6-methoxyquinazoline (98 mg, 0.23 mmol) was added to a solution of 4-methyl-4H-1,2,4-triazole-3-thiol (40 mg, 0.34 mmol) and potassium-t-butoxide (36 mg, 0.32 mmol) in DMF (1 ml) and the mixture heated at 40° C. for 30 minutes. The reaction mixture was allowed to cool and was partitioned between ammonium chloride and ethyl acetate. The organic layer was separated, washed with water and brine, dried (MgSO$_4$) and the solvent removed by evaporation. The residue was purified by column chromatography eluting with a gradient of methylene chloride/methanol (95/50 to 80/20). The purified solid product was triturated with ether and collected by filtration. The solid was dissolved in methylene chloride/methanol and 3M ethereal hydrogen chloride (0.5 ml) was added. The volatiles were removed by evaporation and the residue was crystallised from methylene chloride and ether. The solid was collected by filtration, washed with ether and dried under vacuum to give 4-(4-chloro-2-fluoroanilino)-6-methoxy-7-(2-(4-methyl-4H-1,2,4-triazol-3-ylthio)ethoxy)-quinazoline hydrochloride (90 mg, 79%).

$^1$H NMR Spectrum: (DMSOd$_6$; CF$_3$COOD) 3.78(s, 3H); 3.81(t, 2H); 3.99(s, 3H); 4.57(t, 2H); 7.40(s, 1H); 7.46(dd, 1H); 7.62(t, 1H); 7.67(dd, 1H); 8.16(s, 1H); 8.89(s, 1H); 9.68(s, 1H)

MS - ESI: 461 [MH]$^+$

Elemental Analysis: Found C 43.7 H 3.9 N 14.9 $C_{20}H_{18}N_6O_2ClFS$ 1$H_2O$ 2HCl Requires C 43.5 H 4.0 N 15.2%

The starting material was prepared as follows:

1,2-Dibromoethane (725 mg, 4 mmol) was added by portions of 70 µl every 30 minutes to a mixture of 4-(4-chloro-2-fluoroanilino)-7-hydroxy-6-methoxyquinazoline (320 mg, 1 mmol), (prepared as described for the starting material in Example 24), and potassium carbonate (552 mg, 4 mmol) in DMF (5 ml) heated at 35° C. The mixture was stirred for a further 30 minutes after the completion of the addition and then partitioned between ethyl acetate and water. The organic layer was separated, washed with water and brine, dried (MgSO$_4$) and the solvent removed by evaporation. The residue was triturated with petroleum ether/ether, the solid was collected by filtration and dried under vacuum to give 7-(2-bromoethoxy)-4-(4-chloro-2-fluoroanilino)-6-methoxyquinazoline (200 mg, 47%). $^1$H NMR Spectrum: (DMSOd$_6$) 3.89(t, 2H); 3.96(s, 3H); 4.51(t, 2H); 7.23(s, 1H); 7.35(dd, 1H); 7.55(dd, 1H); 7.59(t, 1H); 7.83(s, 1H); 8.36(s, 1H); 9.57(s, 1H)

MS - ESI: 428 [MH]$^+$

Example 52

Using an analogous procedure to that described in Example 51, 7-(2-bromoethoxy)-4-(4-chloro-2-fluoroanilino)-6-methoxyquinazoline (98 mg, 0.23 mmol), (prepared as described for the starting material in Example 51), was treated with 5-mercapto-1-methyltetrazole (40 mg, 0.35 mmol) to give 4-(4-chloro-2-fluoroanilino)-6-methoxy-7-(2-(1-methyltetrazol-5-ylthio)ethoxy)-quinazoline hydrochloride (50 mg, 44%).

$^1$H NMR Spectrum: (DMSOd$_6$; CF$_3$COOD) 3.8(t, 2H); 3.97(s, 6H); 4.57(t, 2H); 7.35(s, 1H); 7.46(dd, 1H); 7.62(t, 1H); 7.70(dd, 1H); 8.12(s, 1H); 8.87(s, 1H)

MS - ESI: 462 [MH]$^+$

Elemental Analysis: Found C 45.1 H 3.7 N 19.3 $C_{19}H_{17}N_7O_2ClFS$ 0.5$H_2O$ 1HCl Requires C 45.0 H 3.8 N 19.3%

Example 53

Diethyl azodicarboxylate (295 µl, 1.8mmol) was added dropwise to a solution of 2-methyl-1-(3-hydroxypropyl)imidazole (131 mg, 0.93 mmol), (EP 0060696 A1), triphenylphosphine (492 mg, 1.8 mmol) and 4-(4-chloro-2-fluoroanilino)-7-hydroxy-6-methoxyquinazoline (200 mg, 0.62 mmol), (prepared as described for the starting material in Example 24), in methylene chloride (4 ml) and the mixture stirred for 2 hours at ambient temperature. Further 2-methyl-1-(3-hydroxypropyl)imidazole(43 mg,0.31 mmol), triphenylphosphine (82 mg, 0.31 mmol) and diethyl azodicarboxylate (50 µl, 0.31 mmol) were added and the mixture stirred for a further 3 hours. The volatiles were removed by evaporation and the residue was purified by column chromatography eluting with methylene chloride/methanol (93/7). The purified solid was dissolved in methylene chloride and 3M ethereal hydrogen chloride (2 ml) was added. The volatiles were removed by evaporation and the solid residue was suspended in ether, collected by filtration, washed with ether and dried under vacuum to give 4-(4-chloro-2-fluoroanilino)-6-methoxy-7-(3-(2-methylimidazol-1-yl)propoxy)quinazoline hydrochloride (104 mg, 32%).

$^1$H NMR Spectrum: (DMSOd$_6$; CF$_3$COOD) 2.4(t, 2H); 2.60(s, 3H); 4.0(s, 3H); 4.3–4.4(m, 4H); 7.41(s, 1H); 7.46 (dd, 1H); 7.58(s, 1H); 7.62(t, 1H); 7.67(dd, 1H); 7.70(s, 1H); 8.21(s, 1H); 8.88(s, 1H)

MS - ESI: 442 [MH]$^+$

Elemental Analysis: Found C 49.8 H 5.0 N 12.5 $C_{22}H_{21}N_5O_2ClF$ 1$H_2O$ 2HCl Requires C 50.1 H 5.0 N 12.7% 0.23ether Example 54

A solution of 4-(4-chloro-2-fluoroanilino)-6-methoxy-7-(2-(methylaminoethoxy)quinazoline hydrochloride hydrate (13 5 mg, 0.3 mmol) and 2-chloropyrimidine (66 mg, 0.6 mmol) in N,N-diisopropylethylamine (2 ml) was heated at reflux for 1 hour. The mixture was allowed to cool and was triturated with ether. The solid product was collected by filtration and purified by column chromatography eluting with methylene chloride/methanol (95/5). The purified oil was crystallised from ether and the solid collected by filtration. The solid was dissolved in methylene chloride/methanol and a solution of 3M ethereal hydrogen chloride (0.5 ml) was added. The suspension was diluted with ether, the solid product collected by filtration, washed with ether and dried under vacuum to give 4-(4- chloro-2-fluoroanilino)-6-methoxy-7-(2-(N-methyl-N-(pyrimidin-2-yl)amino)ethoxy)quinazoline hydrochloride (52 mg, 33%).

$^1$H NMR Spectrum: (DMSOd$_6$; CF$_3$COOD) 3.36(s, 3H); 3.9(s, 3H); 4.22(t, 2H); 4.51 (t, 2H); 6.94(t, 1H); 7.36(s, 1H); 7.46(d, 1H); 7.63(t, 1H); 7.66(dd, 1H); 8.08(s, 1H); 8.62(d, 2H); 8.9(s, 1H)

MS - ESI: 455 [MH]$^+$

Elemental Analysis: Found C 49.8 H 4.4 N 15.9 $C_{22}H_{20}N_6O_2ClF$ 1 $H_2O$ 1.5HCl Requires C 49.9 H 4.5 N 15.9%

The starting material was prepared as follows:

A solution of di-t-butyl dicarbonate (4.52 g, 20 mmol) in THF (10 ml) was added to a solution of 2-(methylamino) ethanol (1.5 g, 20 mmol) in water (10 ml) and THF (10 ml) and the mixture was stirred for 18 hours at ambient temperature. The organic solvents was removed by evaporation and the residue was partitioned between water and ether. The organic layer was separated, washed with 0.1M hydrochloric acid and brine, dried ($MgSO_4$) and the solvent removed by evaporation to give 2-(N-methyl-N-t-butoxycarbonylamino) ethanol (3 g, 85%) as an oil.

$^1$H NMR Spectrum: ($CDCl_3$) 1.46(s, 9H); 2.92(s, 3H); 3.39(t, 2H); 3.74(t, 2H)

MS - ESI: 176 [MH]$^+$

A solution of 2-(N-methyl-N-t-butoxycarbonylamino) ethanol (116 mg, 0.7 mmol) in methylene chloride (1 ml) was added to a suspension of 4-(4-chloro-2-fluoroanilino)-7-hydroxy-6-methoxyquinazoline (160 mg, 0.5 mmol), (prepared as described for the starting material in Example 24), and triphenylphosphine (393 mg, 1.5 mmol) in methylene chloride (5 ml). Diethyl azodicarboxylate (261 mg, 1.5 mmol) was then added dropwise and the mixture was stirred at ambient temperature for 4 hours. The reaction mixture was poured onto a column of silica and eluted with a gradient of methylene chloride/acetonitrile/methanol (70/30/0 to 70/20/10). The partially purified product was further purified by column chromatography eluting with a gradient of methylene chloride/ether/methanol (60/40/0 to 60/10/30). The pure oil was crystallised from ether, collected by filtration and washed with ether to give 4-(4-chloro-2-fluoroanilino)-6-methoxy-7-(2-(N-methyl-N-t-butoxycarbonylamino)ethoxy)quinazoline (450 mg, 63%).

m.p. 194–196° C.

$^1$H NMR Spectrum: ($CDCl_3$) 1.46(s, 9H); 3.05(br s, 3H); 3.72(br s, 2H); 4.02(s, 3H); 4.27(br s, 2H); 7.0(s, 1H); 7.2–7.3(m, 3H); 8.54(t, 1H); 8.69(s, 1H)

MS - ESI: 499 [MNa]$^+$

Elemental Analysis: Found C 57.2 H 5.7 N 11.5 $C_{23}H_{26}N_4O_4ClF$ 0.3$H_2O$ Requires C 57.3 H 5.6 N 11.6%

TFA (4 ml) was added to a solution of 4-(4-chloro-2-fluoroanilino)-6-methoxy-7-(2-(N-methyl-N-t-butoxycarbonylamino)ethoxy)quinazoline (390 mg, 0.82 mmol) in methylene chloride (4 ml) and the mixture stirred for 2 hours at ambient temperature. Toluene was added and the volatiles were removed by evaporation. The residue was dissolved in methylene chloride and 3M ethereal hydrogen chloride (1 ml) was added. The resulting precipitate was collected by filtration, washed with ether and dried under vacuum to give 4-(4-chloro-2-fluoroanilino)-6-methoxy-7-(2-(methylamino)ethoxy)quinazoline hydrochloride hydrate (290 mg; 79%).

$^1$H NMR Spectrum: (DMSOd$_6$; $CF_3COOD$) 2.74(s, 3H); 3.53(t, 2H); 4.05(s, 3H); 4.53(t, 2H); 7.46(d, 1H); 7.47(s, 1H); 7.6–7.7(m, 2H); 8.24(s, 1H); 8.91(s, 1H)

MS - ESI: 377 [MH]$^+$

Elemental Analysis: Found C 45.8 H 5.0 N 12.0 $C_{18}H_{18}N_4O_2ClF$ 1.1$H_2O$ 2HCl Requires C 46.0 H 4.8 N 11.9%

Example 55

Isonicotinoyl chloride (36 mg, 0.2 mmol) was added to a suspension of 4-(4-chloro-2-fluoroanilino)-6-methoxy-7-(2-(methylamino)ethoxy)quinazoline hydrochloride hydrate (90 mg, 0.1 mmol), (prepared as described for the starting material in Example 54), in methylene chloride (3 ml) and triethylamine (80 mg, 0.8 mmol) was then added dropwise. The mixture was stirred for 30 minutes at ambient temperature and the solvent was then removed by evaporation. The residue was partitioned between ethyl acetate and water, the organic layer was separated, washed with brine, dried ($MgSO_4$) and the solvent removed by evaporation. The residue was dissolved in methylene chloride/methanol and 3M ethereal hydrogen chloride (0.5 ml) was added. The suspension was diluted with ether, the precipitate was collected by filtration, washed with ether and dried under vacuum to give 4-(4-chloro-2-fluoroanilino)-6-methoxy-7-(2-(N-methyl-N-(4-pyridylcarbonyl)amino)ethoxy) quinazoline hydrochloride (75 mg, 67%).

$^1$H NMR Spectrum: (DMSOd$_6$; $CF_3COOD$; 95° C.) 3.1(s, 3H); 3.8–3.9(br s, 2H); 4.1(s, 3H); 4.4–4.6(br s, 2H); 7.4–7.45(m, 2H); 7.55(dd, 1H); 7.65(t, 1H); 7.9–8.0(br s, 2H); 8.28(s, 1H); 8.8(s, 1H); 8.95(s, 2H)

MS - ESI: 482 [MH]$^+$

Elemental Analysis: Found C 51.7 H 4.6 N 12.0 $C_{24}H_{21}N_5O_3ClF$ 1$H_2O$ 1.7HCl Requires C 51.5 H 4.6 N 12.3% 0.1 ether

Example 56

A mixture of 7-(4-pyridylthio)-3,4-dihydroquinazolin-4-one (100 mg, 0.4 mmol), thionyl chloride (20 ml) and DMF (0.1 ml) was heated at reflux for 1.5 hours. The volatiles were removed by evaporation and the residue azeotroped with toluene. A solution of 3-hydroxy-4-methylaniline (53 mg, 0.04 mmol) in isopropanol (10 ml) was added to the solid residue and the mixture was heated at reflux for 2 hours. The mixture was allowed to cool and the precipitated product collected by filtration, washed with isopropanol and dried to give 4-(3-hydroxy4-methylanilino)-7-(4-pyridylthio)quinazoline hydrochloride(103 mg, 73%).

$^1$H NMR Spectrum: (DMSOd$_6$) 2.17(s, 3H); 7.05(dd, 1H); 7.17(d, 1H); 7.19(s, 1H); 7.64(d, 2H); 8.00(d, 1H); 8.20(s, 1H); 8.66(d, 2H); 8.92(s, 1H); 9.05(d, 1H)

MS - ESI: 361 [MH]$^+$

Elemental analysis: Found C 53.2 H 4.6 N 11.8 $C_{20}H_{16}N_4OS$ 1$H_2O$ 2HCl Requires C 53.2 H 4.4 N 12.4%

The starting material was prepared as follows:

A solution of 2-amino-4-fluorobenzoic acid (3 g, 19.3 mmol) in formamide (30 ml) was heated at 150° C. for 6 hours. The reaction mixture was poured onto ice/water 1/1 (250 ml). The precipitated solid was collected by filtration, washed with water and dried to give 7-fluoro-3,4-dihydroquinazolin-4-one (2.6 g, 82%).

Sodium hydride (3.3 g of a 50% suspension in mineral oil, 69 mmol) was added to a solution of 4-mercaptopyridine (8.12 g, 73 mmol) in DMF (100 ml) and the mixture stirred for 30 minutes. 7-Fluoro-3,4-dihydroquinazolin-4-one (1.5 g, 9 mmol) was added and the reaction heated at 100° C. for 4 hours. The mixture was allowed to cool, diluted with water and extracted with ethyl acetate. The organic extracts were washed with water and brine, dried ($MgSO_4$) and the solvent removed by evaporation. The residue was purified by column chromatography eluting with methylene chloride/methanol (97/3) to give 7-(4-pyridylthio)-3,4-dihydroquinazolin-4-one (500 mg, 6%).

$^1$H NMR Spectrum: (DMSOd$_6$) 7.24(d, 2H); 7.54(dd, 1H); 7.70(d, 1H); 8.10(s, 1H); 8.14(d, 1H); 8.44(d, 2H)

MS - ESI: 256 [MH]$^+$

Example 57

A mixture of 4-chloro-2-fluoro-3-hydroxyaniline (118 mg, 0.7 mmol), (EP 061741 A2), and 4-chloro-6-methoxy- 7-((4-pyridyl)methoxy)quinazoline (200 mg, 0.7 mmol), (prepared as described for the starting material in Example 13), in isopropanol (10 ml) and ethereal hydrogen chloride (5 ml) was heated at 80° C. for 2 hours and the mixture was allowed to cool. The precipitated product was collected by filtration, washed with isopropanol and dried to give 4-(4-chloro-2-fluoro-5-hydroxyanilino)-6-methoxy-7-((4-pyridyl)methoxy)quinazoline hydrochloride (110 mg, 31%).

$^1$H NMR Spectrum: (DMSOd$_6$) 3.96(s, 3H); 5.38(s, 2H); 7.14(d, 1H); 7.24(s, 1H); 7.38(d, 1H); 7.48(d, 2H); 7.82(s, 1H); 8.32(s, 1H); 8.58(d, 2HO; 9.48(s, 1H)

MS - ESI: 427 [MH]$^+$

Example 58

A mixture of 7-((2-chloro-4-pyridyl)methoxy)-6-methoxy-3,4-dihydroquinazolin-4-one (150 mg, 0.47 mmol), phosphoryl chloride (0.2 ml) and N,N-dimethylaniline (0.2 ml) in toluene (5 ml) was heated at reflux for 1 hour. The volatiles were removed by evaporation and the residue was partitioned between ethyl acetate and saturated sodium hydrogen carbonate solution. The organic layer was separated, dried (MgSO$_4$) and the solvent removed by evaporation. A solution of 2-fluoro-5-hydroxy-4-methylaniline (67 mg, 0.47 mmol), (prepared as described for the starting material in Example 13), in isopropanol (10 ml) was added to the solid residue and the mixture was heated at reflux for 2 hours. The mixture was allowed to cool and the precipitated product collected by filtration, washed with acetone and dried to give 7-((2-chloro-4-pyridyl)methoxy)-4-(2-fluoro-5-hydroxy-4-methylanilino)-6-methoxyquinazoline hydrochloride (70 mg, 30%).

m.p. 245–250° C.

$^1$H NMR Spectrum: (DMSOd$_6$) 2.30(s, 3H); 4.10(s, 3H); 5.45(s, 2H); 6.90(d, 1H); 7.10(d, 1H); 7.35(s, 1H); 7.50(d, 1H); 7.65(s, 1H); 8.25(s, 1H); 8.45(d, 1H); 8.75(s, 1H); 9.60(br s, 1H); 11.30(s, 1H)

MS - ESI: 441 [MH]$^+$

Elemental analysis: Found C 53.7 H 4.0 N 10.9
C$_{22}$H$_{18}$N$_4$O$_3$FCl 1H$_2$O 1HCl Requires C 53.4 H 4.3 N 11.3%

The starting material was prepared as follows:

Oxalyl chloride (0.3 ml) was added to a mixture of 4-(2-chloropyridine)carboxylic acid (950 mg, 6 mmol) and DMF (0.05 ml) in methylene chloride (20 ml) and the mixture strirred at ambient temperature for 1 hour. The volatiles were removed by evaporation and ethanol (10 ml) was added to the residue and the mixture stirred at ambient temperature for 18 hours. Water was added and the mixture was extracted with ethyl acetate (3×25 ml). The extracts were combined, dried (MgSO$_4$) and the solvent removed by evaporation to give ethyl 4-(2-chloropyridine)carboxylate (700 mg, 63%) as a brown oil.

$^1$H NMR Spectrum: (DMSOd$_6$) 1.30(t, 3H); 4.37(q, 2H); 7.80(m, 2H); 8.60(d, 1H) Lithium aluminium hydride (5 ml of a 1M solution in ether, 5 mmol) was added dropwise to a stirred solution of ethyl 4-(2-chloropyridine)carboxylate (700 mg, 3.8 mmol) in ether (10 ml) at 0° C. The mixture was allowed to warm to ambient temperature, wet ether and 2M sodium hydroxide solution (2 ml). The insolubles were removed by filtration, the organic phase was separated and the aqueous layer was extracted with ether (3×25 ml). The extracts were combined, dried (MgSO$_4$) and the solvent removed by evaporation to give 2-chloro-4-hydroxymethylpyridine (180 mg, 33%) as a brown oil which crystallised on standing.

$^1$H NMR Spectrum: (DMSOd$_6$) 4.55(s, 2H); 5.50(br s, I H); 7.32(d, 1H); 7.20(s, 1H); 8.30(d, 1H)

A mixture of 2-chloro-4-hydroxymethylpyridine (180 mg, 1.25 mmol), thionyl chloride (0.2 ml) in toluene (10 ml) was stirred at ambient temperature for 1 hour. The volatiles were removed by evaporation to give 2-chloro-4-chloromethylpyridine hydrochloride (180 mg, 0.9 mmol). A mixture of 7-hydroxy-6-methoxy-4-phenoxyquinazoline (268 mg, 1 mmol), (prepared as described for the starting material in Example 13), potassium carbonate (680 mg, 5 mmol) and DMF (10 ml) was added to this crude product and the mixture was heated at 90° C. for 1 hour. The mixture was allowed to cool, diluted with water and extracted with ethyl acetate (3×70 ml). The extracts were combined, washed with water (x3) and brine, dried (MgSO$_4$) and the solvent removed by evaporation to give 7-((2-chloro-4-pyridyl)methoxy)-6-methoxy-4-phenoxyquinazoline (260 mg, 66%) as a solid.

$^1$H NMR Spectrum: (DMSOd$_6$) 4.00(s, 3H); 5.45(s, 2H); 7.30(m, 3H); 7.42(s, 1H); 7.4–7.5(m, 3H); 7.60(s, 1H); 7.62(s, 1H); 8.44(d, 1H); 8.52(s, 1H)

MS - ESI: 394 [MH]$^+$

A mixture of 7-((2-chloro-4-pyridyl)methoxy)-6-methoxy-4-phenoxyquinazoline (260 mg, 0.7 mmol) and 2M hydrochloric acid (15 ml) was heated at 85° C. for 2 hours. The mixture was allowed to cool and adjusted to pH6–7 with sodium hydrogen carbonate solution. The resulting precipitate was collected by filtration and dried to give 7-((2-chloro-4-pyridyl)methoxy)-6-methoxy-3,4-dihydroquinazolin-4-one (160 mg, 76%).

$^1$H NMR Spectrum: (DMSOd$_6$) 3.90(s, 3H); 5.36(s, 2H); 7.18(s, 1H); 7.45(m, 2H); 7.46(s, 1H); 7.59(s, 1H); 8.42(d, 1H)

MS - ESI: 318 [MH]$^+$

Example 59

A mixture of 4-(4-chloro-2-fluoroanilino)-7-hydroxy-6-methoxyquinazoline (950 mg, 3 mmol), (prepared as described for the starting material in Example 24), 2-bromo-4-bromomethylpyridine (765 mg, 3 mmol) and potassium carbonate (2.38 g 17 mmol) in DMF (10 ml) was heated at 80° C. for 2 hours. The mixture was allowed to cool, poured into water and extracted with ethyl acetate. The combined extracts were dried (MgSO$_4$) and the solvent removed by evaporation and azeotroped with toluene. The residue was triturated with ethyl acetate/hexane and the solid product collected by filtration, washed with ethyl acetate/hexane and dried to give 7-((2-bromo-4-pyridyl)methoxy)-4-(4-chloro-2-fluoroanilino)-6-methoxyquinazoline (647 mg, 44%).

m.p. 210–212° C.

$^1$H NMR Spectrum: (DMSOd$_6$) 3.98(s, 3H); 5.40(s, 2H); 7.25(s, 1H); 7.30(d, 1H); 7.50(s, 1H); 7.50(d, 1H); 7.55(m, 2H); 7.74(s, 1H); 7.86(s, 1H); 8.35(br s, 1H); 8.42(d, 1H); 9.56(s, 1H)

MS - ESI: 489 [MH]$^+$

Elemental analysis: Found C 52.0 H 3.2 N 11.2
C$_{21}$H$_{15}$N$_4$O$_2$BrClF Requires C 51.5 H 3.1 N 11.4%

The starting material was prepared as follows:

A mixture of 2-bromo-4-methylpyridine (12.2 g), N-bromosuccinimide (30 g) and 2,2'-azobis(2-methylpropionitrile) (100 mg) in carbon tetrachloride (200 ml) was heated at reflux for 2.5 hours. The mixture was allowed to cool and the insoluble material removed by filtration. The solvent was removed from the filtrate by evaporation and the residue was purified by filtration through a silica pad eluting with ethyl acetate/hexane (10/1) to give 2-bromo-4-bromomethylpyridine.

$^1$H NMR Spectrum: (DMSOd$_6$) 4.65(s, 2H); 7.50(d, 1H); 7.42(s, 1H); 7.70(s, 1H); 8.35(d, 1H)

MS - ESI: 250 [MH]$^+$

Example 60

A mixture of 4-(4-chloro-2-fluoroanilino)-7-hydroxy-6-methoxyquinazoline (600 mg, 2 mmol), (prepared as described for the starting material in Example 24), 4-chloromethyl-2-cyanopyridine hydrochloride (620 mg, 3 mmol) and potassium carbonate (1.0 g 7 mmol) in DMF (8 ml) was heated at 80° C. for 30 minutes. The mixture was allowed to cool, poured into water and extracted with ethyl acetate. The combined extracts were dried (MgSO$_4$) and the solvent removed by evaporation and azeotroped with toluene. The residue was triturated with ethyl acetate/hexane, the solid product collected by filtration and purified by column chromatography eluting with ethyl acetate and further chromatography eluting with methylene chloride/ methanol (99/1). The purified product was recrystallised from ethyl acetate/hexane to give 4-(4-chloro-2-fluoroanilino)-7-((2-cyano4-pyridyl)methoxy)-6-methoxyquinazoline (35 mg, 4%).

m.p. 209–213° C.

$^1$H NMR Spectrum: (DMSOd$_6$) 3.98(s, 3H); 5.44(s, 2H); 7.26(s, 1H); 7.34(dd, 1H); 7.53(dd, 1H); 7.58(d, 1H); 7.80(d, 1H); 7.85(s, 1H); 8.27(s, 1H); 8.35(s, 1H); 8.80(d, 1H); 9.60(s, 1H)

MS - ESI: 436 [MH]$^+$

Elemental analysis: Found C 60.3 H 3.4 N 16.1 C$_{22}$H$_{15}$N$_5$O$_2$ClF Requires C 60.6 H 3.5 N 16.1%

The starting material was prepared as follows:

Tetrabutyl ammonium fluoride (9 ml of a 1M solution in THF, 9 mmol) was added to a solution of 2-cyano-4-dimethyl-t-butylsilyloxymethylpyridine (1.4 g, 5.6 mmol), (J.Het. Chem. 1993, 30, 631), in THF (15 ml) and the mixture was stirred for 2 hours at ambient temperature. Water was added and the volatiles were removed by evaporation. The residue was partitioned between ethyl acetate and water. The organic layer was separated and the aqueous layer extracted with ethyl acetate. The combined extracts were dried (MgSO$_4$) and the solvent removed by evaporation to give 2-cyano-4-hydroxymethylpyridine (0.55 g, 73%).

$^1$H NMR Spectrum: (DMSOd$_6$) 4.65(s, 2H); 5.70(t, 1H); 7.70(d, 1H); 7.95(s, 1H); 8.75(d, 1H) A mixture of 2-cyano-4-hydroxymethylpyridine (0.51 g, 3.8mmol) and thionyl chloride (0.6 ml) in toluene (20 ml) was stirred at room temperature for 1 hour. The volatiles were removed by evaporation and the residue azeotroped with toluene to give 4-chloromethyl-2-cyanopyridine hydrochloride (620 mg, 86%).

$^1$H NMR Spectrum: (DMSOd$_6$) 4.75(s, 2H); 7.75(dd, 1H); 8.05(s, 1H): 8.34(d, 1H)

Example 61

A mixture of 7-((6-chloro-2-oxo-1,2-dihydropyrid-4-yl)methoxy)-6-methoxy-3,4-dihydroquinazolin-4-one (190 mg, 0.4 mmol), thionyl chloride (5 ml) and DMF (0.1 ml) was heated at reflux for 2 hours. The volatiles were removed by evaporation and the residue azeotroped with toluene. A solution of 4-chloro-2-fluoroaniline (1 ml) in isopropanol (15 ml) was added to the solid residue and the mixture was heated at reflux for 3 hours. The mixture was allowed to cool and the precipitated product collected by filtration, washed with isopropanol and dried to give 4-(4-chloro-2-fluoroanilino)-7-((6-chloro-2-oxo-1,2-dihydropyrid-4-yl) methoxy)-6-methoxyquinazoline hydrochloride (110 mg, 41%).

m.p. 271–273° C. (decomp.)

$^1$H NMR Spectrum: (DMSOd$_6$) 4.08(s, 3H); 5.35(s, 2H); 6.70(s, 1H); 7.00(s, 1H); 7.30(s, 1H); 7.40(d, 1H); 7.60(m, 2H); 8.30(s, 1H); 8.75(s, 1H)

MS - ESI: 461 [MH]$^+$

The starting material was prepared as follows:

A mixture of 2,6-dichloro-4-hydroxymethylpyridine (1.72 g, 16 mmol) and 40% aqueous sodium hydroxide solution (5 ml) in methanol (50 ml) was heated at reflux for 24 hours. The mixture was allowed to cool and the volatiles removed by evaporation. The residue was extracted with ethyl acetate and the solvent removed from the extracts by evaporation. The residue was recrystallised from ethyl acetate/hexane to give 2-chloro-4-hydroxymethyl-6-methoxypyridine (490 mg, 28%).

$^1$H NMR Spectrum: (DMSOd$_6$) 3.80(s, 3H); 4.45(d, 2H); 5.45(t, 1H); 6.70(s, 1 H); 6.98(s, 1 H)

Thionyl chloride (1.0 ml) was added to a solution of 2-chloro-4-hydroxymethyl-6-methoxypyridine (0.9 g, 5.2 mmol) in toluene (10 ml) and the mixture stirred at ambient temperature for 1 hour. The volatiles were removed by evaporation, the residue was azeotroped with toluene and dried under vacuum to give 2-chloro-4-chloromethyl-6-methoxypyridine hydrochloride (0.88 g, 74%).

$^1$H NMR Spectrum: (DMSOd$_6$) 3.85(s, 3H); 4.70(s, 2H); 6.90(s, 1H); 7.15(s, 1H)

A mixture of 7-hydroxy-6-methoxy-4-phenoxyquinazoline (1.1 g, 4.1 mmol), (prepared as described for the starting material in Example 13), 2-chloro-4-chloromethyl-6-methoxypyridine hydrochloride (0.88 g, 3.9 mmol) and potassium carbonate (2.0 g, 14 mmol) in DMF (20 ml) was heated at 80° C. for 1 hour. The mixture was allowed to cool, diluted with water and the precipitated product collected by filtration, washed with water and dried to give 7-((2-chloro-6-methoxy-4-pyridyl)methoxy)-6-methoxy-4-phenoxyquinazoline (1.38 g, 79%).

$^1$H NMR Spectrum: (CDCl$_3$) 3.95(s, 3H); 4.04(s, 3H); 5.20(s, 2H); 6.70(s, 1H); 6.95(s, 1H); 7.18(m, 3H); 7.30(t, 1H); 7.40(t, 2H); 7.58(s, 1H); 8.52(s, 1H)

MS - ESI: 424 [MH]$^+$

A mixture of 7-((2-chloro-6-methoxy-4-pyridyl) methoxy)-6-methoxy-4-phenoxyquinazoline (400 mg, 0.95 mmol) and 2M hydrochloric acid (20 ml) was heated at reflux for 3 hours. The mixture was allowed to cool and adjusted to pH6–7 with aqueous ammonia solution. The resulting precipitate was collected by filtration washed with water and dried to give crude 7-((6-chloro-2-oxo-1,2-dihydropyrid-4-yl)methoxy)-6-methoxy-3,4-dihydroquinazolin-4-one (190 mg, 60%).

Example 62

Thionyl chloride (0.6 ml) was added to a solution of 4-hydroxymethyl-2-methoxypyridine (0.59 g, 4.2 mmol) in toluene (10 ml) and the mixture stirred at ambient temperature for 1.5 hours. The volatiles were removed by evaporation and the residue was azeotroped with toluene and dried under vacuum to give crude 4-chloromethyl-2-methoxypyridine hydrochloride (0.50 g, 2.6 mmol) which was used directly. This product was then added to a mixture of 4-(4-chloro-2-fluoroanilino)-7-hydroxy-6-methoxyquinazoline (420 mg, 1.3 mmol), (prepared as described for the starting material in Example 24), and potassium carbonate (1.0 g 7 mmol) in DMF (8 ml) and the resulting mixture was heated at 75° C. for 2 hours. The mixture was allowed to cool, diluted with water and the precipitated solid collected by filtration, washed with water and dried to give 4-(4-chloro-2-fluoroanilino)-7-((2-methoxy-4-pyridyl)methoxy)-6-methoxyquinazoline (140 mg, 25%).

m.p. 202–204° C.

$^1$H NMR Spectrum: (DMSOd$_6$) 3.85(s, 3H); 3.98(s, 3H); 5.35(s, 2H); 6.88(s, 1H); 7.05(d, 1H); 7.24(s, 1H); 7.35(dd, 1H); 7.54(dd, 1H); 7.58(t, 1H); 7.84(s, 1H); 8.11 (d, 1H); 8.35(s, 1H); 9.58(br s, 1H)

MS - ESI: 441 [MH]$^+$

Elemental analysis: Found C 59.9 H 4.1 N 12.4 C$_{22}$H$_{18}$N$_4$O$_3$ClF Requires C 59.9 H 4.1 N 12.7%

The starting material was prepared as follows:

A mixture of ethyl 2-hydroxy-pyridine-4-carboxylate (1.0 g, 6 mmol), (Chem. Abs. 1957, 8740c), methyl iodide (1 ml) and silver(I)carbonate (1.64 g) in toluene (20 ml) was heated at reflux for 2 hours. The mixture was allowed to cool and the insolubles removed by filtration through diatomaceous earth and the pad was washed through with ethyl acetate. The filtrate was washed with water, dried (MgSO$_4$) and the solvent removed by evaporation to give ethyl 2-methoxy-pyridine-4-carboxylate (0.93 g, 86%) as a yellow oil.

$^1$H NMR Spectrum: (CDCl$_3$) 1.30(t, 3H); 3.90(s, 3H); 4.30(q, 2H); 7.24(s, 1H); 7.35(d, 1H); 8.20(d, 1H)

MS - ESI: 182 [MH]$^+$

A solution of ethyl 2-methoxy-pyridine-4-carboxylate (0.93 g, 5 mmol) in ether (5 ml) was added to lithium aluminium hydride (0.3 g, 8 mmol) in ether (10 ml) cooled to 5° C. and the mixture stirred for 2 hours. Water was added, the mixture was filtered through diatomaceous earth and the pad was washed through with ethyl acetate. The filtrate was extracted with ethyl acetate and the combined extracts were washed with brine, dried (MgSO$_4$) and the solvent removed by evaporation to give 4-hydroxymethyl-2-methoxypyridine (0.64 g, 89%) as a yellow oil.

$^1$H NMR Spectrum: (CDCl$_3$) 3.86(s, 3H); 4.62(s, 2H); 6.65(s, 1H); 6.76(d, 1H); 8.05(d, 1H)

MS - ESI: 140 [MH]$^+$

Example 63

Thionyl chloride (0.3 ml) was added to a solution of 4-hydroxymethyl-2-methylpyridine (240 mg, 1.9 mmol) in toluene (10 ml) and the mixture stirred at ambient temperature for 2 hours. The volatiles were removed by evaporation, the residue azeotroped with toluene and dried under vacuum to give crude 4-chloromethyl-2-methylpyridine hydrochloride which was used directly. This product was then added to a mixture of 4-(4-chloro-2-fluoroanilino)-7-hydroxy-6-methoxyquinazoline (510 mg, 1.6mmol), (prepared as described for the starting material in Example 24), and potassium carbonate (1.4 g 10 mmol) in DMF (8 ml) for 90 hours. The mixture was diluted with water and the precipitated solid collected by filtration, washed with water and dried to give 4-(4-chloro-2-fluoroanilino)4-methoxy- 7-((2-methyl4-pyridyl)methoxy)quinazoline (290 mg, 43%), a sample was recrystallised from ethyl acetate/hexane.

m.p. 221–224° C.

$^1$H NMR Spectrum: (CDCl$_3$) 2.50(s, 3H); 4.00(s, 3H); 5.20(s, 2H); 6.98(s, 1H); 7.15(d, 1H); 7.2(m, 4H); 8.45(m, 2H); 8.60(s, 1H)

Elemental analysis: Found C 61.7 H 4.2 N 13.2 C$_{22}$H$_{18}$N$_4$O$_2$ClF Requires C 62.2 H 4.3 N 13.2%

The starting material was prepared as follows:

Oxalyl chloride (1.9 g, 15 mmol) was added to 2-chloro-6-methyl-pyridine4-carboxylic acid (1.7 g, 10 mmol) in methylene chloride (30 ml) and the mixture stirred for 2 hours. The volatiles were removed by evaporation and methanol (20 ml) added to the residue. The mixture was stirred for 1 hour and the volatiles removed by evaporation to give methyl 2-chloro-6-methyl-pyridine-4-carboxylate (1.85 g, 100%) as an off-white solid.

$^1$H NMR Spectrum: (CDCl$_3$) 2.55(s, 3H); 3.90(s, 3H); 7.55(s, 1H); 7.60(s, 1H);

MS - ESI: 186 [MH]$^+$

A mixture of methyl 2-chloro-6-methyl-pyridine-4-carboxylate (1.8 g, 10 mmol) and 10% palladium-on-charcoal catalyst (200 mg) in methanol (100 ml) was stirred under hydrogen at 5 atmospheres pressure. The catalyst was removed by filtration and the volatiles removed from the filtrate by evaporation. The residue was treated with 10% aqueous sodium hydroxide solution and extracted with ether (3×30 ml). The combined extracts were dried (MgSO$_4$) and the solvent removed by evaporation to give methyl 2-methyl-pyridine-4-carboxylate (800 mg, 53%) as an oil.

A solution of methyl 2-methyl-pyridine-4-carboxylate (800 mg, 6 mmol) in ether (5 ml) was added to lithium aluminium hydride (340 mg, 9 mmol) in ether (10 ml) cooled to 5° C. and the mixture stirred for 2 hours. Water was added, the mixture was filtered through diatomaceous earth and the pad was washed through with ethyl acetate. The filtrate was extracted with ethyl acetate and the combined extracts were washed with brine, dried (MgSO$_4$) and the solvent removed by evaporation to give 4-hydroxymethyl-2-methylpyridine (240 mg, 38%) as a yellow oil.

1H NMR Spectrum: (CDCl$_3$) 2.48(s, 3H); 5.44(s, 2H); 7.00(d, 1H); 7.10(s, 1H); 8.40(d, 1H)

MS - ESI: 124 [MH]$^+$

Example 64

A mixture of 4-(4-chloro-2-fluoroanilino)-7-hydroxy-6-methoxyquinazoline (350 mg, 0.9 mmol), (prepared as described for the starting material in Example 24), 2-(2-chloroethylthio)-1-methylimidazole hydrochloride (203 mg, 0.95 mmol) and potassium carbonate (303 mg 2.2 mmol) in NMP (20 ml) was heated at 90° C. for 2 hours. The mixture was allowed to cool, diluted with water and extracted with ethyl acetate. The combined extracts were washed with water, dried (MgSO$_4$) and the solvent removed by evaporation. The residue was purified by column chromatography eluting with methylene chloride/methanol (100/0 increasing to 90/10) to give 4-(4-chloro-2-fluoroanilino)-6-methoxy-7-(2-(1-methylimidazol-2-ylthio)ethoxy)quinazoline (75 mg, 17%) as a solid.

$^1$H NMR Spectrum: (DMSOd$_6$) 3.46(s, 3H); 3.93(s, 3H); 4.39–4.44(m, 4H); 7.13(dd, 2H); 7.23(s, 1H); 7.31(dd, 1H); 7.49–7.60(m, 2H); 7.79(s, 1H); 8.37(s, 1H); 9.51(s, 1H)

MS - ESI: 460 [MH]$^+$

Elemental analysis: Found C 52.8 H 4.0 N 14.3 C$_{21}$H$_{19}$N$_5$O$_2$ClFS 1H$_2$O Requires C 52.8 H 4.4 N 14.7%

The starting material was prepared as follows:

2-Chloroethanol (3 g, 37 mmol) was added to a solution of 2-mercapto-1-methylimidazole (3.45 g, 30 mmol) in 2M aqueous sodium hydroxide solution (30 ml) and the mixture heated at 100° C. for 2 hours. The mixture was allowed to cool and extracted with ethyl acetate. The combined extracts were dried (MgSO$_4$) and the solvent removed by evaporation to give 2-(2-hydroxyethylthio)-1-methylimidazole (3.9 g, 82%).

$^1$H NMR Spectrum: (DMSOd$_6$) 3.04(t, 2H); 3.30(s, 3H); 3.54(t, 2H); 5.00(s, 1H); 6.87(s, 1H); 7.20(s, 1H)

Thionyl chloride (1.41 ml, 19 mmol) was slowly added to a solution of 2-(2-hydroxyethylthio)-1-methylimidazole (1.81 g, 11 mmol) in trichloromethane (20 ml) at 5° C. The mixture was stirred for 1 hour at 5° C. and then for 3 hours at ambient temperature. The volatiles were removed by evaporation and the residue azeotroped with toluene to give 2-(2-chloroethylthio)-1-methylimidazole hydrochloride (l.5 g, 77%).

$^1$H NMR Spectrum: (DMSOd$_6$) 3.58 (t, 2H); 3 78(s, 3H); 3.80(t, 2H); 7.78(d, 1H); 7.83(d, 1H)

Example 65

Thionyl chloride (0.55 ml, 7.5 mmol) was added to a solution of 1-(3-hydroxypropyl)-1,2dihyro-2-pyridone (770 mg, 5 mmol) in trichloromethane (1 5 ml) at 5° C. The mixture was stirred at 5° C. for 1 hour and then at ambient temperature for 2 hours. The volatiles were removed by evaporation, the residue azeotroped with toluene and dried under vacuum to give crude 1-(3-chloropropyl)-1,2-dihydro-2-pyridone (500 mg) which was used directly. Part of this product (206 mg, 1.2 mmol) was then added to a mixture of 4-(4-chloro-2-fluoroanilino)-7-hydroxy-6-methoxyquinazoline (350 mg, 1.0 mmol), (prepared as described for the starting material in Example 24), and potassium carbonate (303 mg, 2.2 mmol) in NMP (20 ml) and the reaction mixture was heated at 90° C. for 2 hours. The mixture was allowed to cool, diluted with water and extracted with ethyl acetate. The combined extracts were washed with water, dried (MgSO$_4$) and the solvent removed by evaporation. The residue was purified by column chromatography eluting with methylene chloride/methanol mixtures (100/0 increasing to 95/5) to give 4-(4-chloro-2-fluoroanilino)-6-methoxy-7-(3-(2-oxo-1,2-dihydro-1-pyridyl)propoxy)quinazoline (194 mg, 50%).

m.p. 216–218° C.

$^1$H NMR Spectrum: (DMSOd$_6$) 2.18(m, 2H); 3.90(s, 3H); 4.06(t, 2H); 4.15(t, 2H); 6.18(t, 1H); 6.38(d, 1H); 7.15(s, 1H); 7.30–7.42(m, 2H); 7.50–7.64(m, 3H); 7.79(s, 1H); 8.34(s, 1H); 9.50(s, 1H)

MS - ESI: 455 [MH]$^+$

Elemental analysis: Found C 59.4 H 4.6 N 12.1 C$_{23}$H$_{20}$N$_4$O$_3$ClF 0.5H$_2$O Requires C 59.6 H 4.6 N 12.1%

The starting material was prepared as follows:

Sodium hydride (1.31 g of a 50% suspension in mineral oil, 27 mmol) was added to a solution of 2-hydroxypyridine (2.35 g, 24 mmol) in DMF (50 ml) and the mixture stirred for 30 minutes. 2-(3-Bromopropoxy)tetrahydropyran (5.0 g, 22.5 mmol), (J. Chem. Soc. 1963, 3440), was added and the mixture heated at 100° C. for 3 hours and then stirred at ambient temperature for 18 hours. The reaction mixture was diluted with water and extracted with ethyl acetate. The combined extracts were washed with water, dried (MgSO$_4$) and the solvent removed by evaporation. The residue was purified by column chromatography eluting with methylene chloride/methanol mixtures (100/0 increasing to 97/3) to give: 1-(3-(2-tetrahydropyranyloxy)propyl)-1,2-dihydro-2-pyridone (1.6 g, 30%).

$^1$H NMR Spectrum: (DMSOd$_6$) 1.39–1.75(m, 6H); 1.85 (m, 2H); 3.24–3.42(m, 3H); 3.58–3.74(m, 2H); 3.90(t, 2H); 4.52(s, 1H); 6.18(t, 1H); 6.35(d, 1H); 7.38(dd, 1H); 7.60 (dd,1H)

MS - ESI: 238 [MH]$^+$ and 2-(3-(2-tetrahydropyranyloxy)propyloxy)pyridine (1.43 g, 27%).

$^1$H NMR Spectrum: (DMSOd$_6$) 1.38–1.70(m, 6H); 1.90 (m, 2H); 3.30(m, 3H); 3.34–3.50(m, 2H); 3.62–3.80(m, 2H); 4.30(t, 2H); 4.52(s, 1H); 6.78(d, 1H); 6.92(dd, 1H); 7.64(m, 1H); 8.15(dd,1H)

MS - ESI: 238 [MH]$^+$

A solution of 1-(3-(2-tetrahydropyranyloxy)propyl)-1,2-dihydro-2-pyridone (1.0 g, 4.5 mmol) in acetic acid (8 ml), THF (4 ml) and water (2 ml) was heated at 50° C. for 4 hours. The volatiles were removed by evaporation and the residue azeotroped with toluene to give 1-(3-hydroxypropyl)-1,2-dihydro-2-pyridone (680 mg, 99%) as an off-white solid.

$^1$H NMR Spectrum: (DMSOd$_6$) 1.74(m, 2H); 3.38(m, 2H); 3.90(t, 2H); 4.58(s, 1H); 6.18(dd, 1H); 6.38(d, 1H); 7.38(m, 1H); 7.60(dd, 1H)

Example 66

Thionyl chloride (0.80 ml, 11 mmol) was added to a solution of 2-(3-hydroxypropylthio)-1-methylimidazole (1.25 g, 7.3 mmol) in trichloromethane (25 ml) at 5° C. The mixture was stirred at 5° C. for 1 hour and then at ambient temperature for 2 hours. The volatiles were removed by evaporation, the residue azeotroped with toluene and dried under vacuum to give crude 2-(3-chloropropylthio)-1-methylimidazole hydrochloride (1.0 g) which was used directly. Part of this product (226 mg, 1.0 mmol) was added to a mixture of 4-(4-chloro-2-fluoroanilino)-7-hydroxy-6-methoxyquinazoline (350 mg, 10 mmol), (prepared as described for the starting material in Example 24), and potassium carbonate (303 mg 2.2 mmol) in NMP (20 ml) and the mixture was heated at 90° C. for 2 hours. The mixture was allowed to cool, diluted with water and extracted with ethyl acetate. The combined extracts were wahed with water, dried (MgSO$_4$) and the solvent removed by evaporation. The residue was purified by column chromatography eluting with methylene chloride/methanol (100/0 increasing to 95/5) to give 4-(4-chloro-2-fluoroanilino)-6-methoxy-7-(3-(1-methylimidazol-2- ylthio) propoxy)quinazoline (29 mg, 6%).

m.p. 199–201° C.

$^1$HNMR Spectrum: (DMSOd$_6$) 2.22(m, 2H); 3.44(s, 3H); 3.94(s, 3H); 4.10(m, 4H); 7.10(d, 2H); 7.30(dd, 1H); 7.50–7.60(m, 2H); 7.79(s, 1H); 8.34(s, 1H); 9.50(s, 1H)

MS - ESI: 474 [MH]$^+$

Elemental analysis: Found C 50.9 H 4.8 N 13.2 C$_{22}$H$_{21}$N$_5$O$_2$ClFS 2.5H$_2$O Requires C 50.9 H 5.1 N 13.5%

The starting material was prepared as follows:

Sodium hydride (0.95 g of a 50% suspension in mineral oil, 20 mmol) was added to a solution of 2-mercapto-1-methylimidazole (2.26 g, 19 mmol) in DMF (100 ml) and the mixture stirred for 30 minutes. 2-(3-Bromopropoxy) tetrahydropyran (5.0 g, 22.5 mmol), (J. Chem. Soc. 1963, 3440), was added and the mixture heated at 100° C. for 3 hours and then stirred at ambient temperature for 18 hours. The reaction mixture was diluted with water and extracted with ethyl acetate. The combined extracts were washed with water, dried (MgSO$_4$) and the solvent removed by evaporation. The residue was purified by column chromatography eluting with methylene chloride/methanol mixtures (100/0 increasing to 97/3) to give 1-methyl-2-(3-(2-tetrahydropyranyloxy)propylthio)imidazole (2.5 g, 55%).

¹H NMR Spectrum: (DMSOd₆) 1.38–1.72(m, 6H); 1.80 (m, 2H); 3.0(t, 2H); 3.36–343(m, 2H); 3.58(s, 3H); 3.62–3.78(m, 2H); 4.50(s, 1H); 6.90(s, 1H); 7.21(s, 1H)

A solution of 1-methyl-2-(3-(2-tetrahydropyranyloxy) propylthio)imidazole (2.0 g, 7.8mmol) in acetic acid (8 ml), THF (4 ml) and water (2 ml) was heated at 50° C. for 4 hours. The volatiles were removed by evaporation and the residue azeotroped with toluene to give 2-(3-hydroxypropylthio)-1-methylimidazole (1.3 g, 100%) as an off-white solid.

¹H NMR Spectrum: (DMSOd₆) 1.68(m, 2H); 2.98(t, 2H); 3.42(t, 2H); 3.57(s, 3H); 4.10(s, 1H); 6.90(d, 1H); 7.20(d, 1H)

Example 67

A mixture of 4-(4-chloro-2-fluoroanilino)-7-hydroxy-6-methoxyquinazoline (350 mg, 1.0 mmol), (prepared as described for the starting material in Example 24), 4-(3-chloropropoxy)pyridine hydrochloride (206 mg, 1.0 mmol) and potassium carbonate (303 mg, 2.2 mmol) in NMP (20 ml) was heated at 90° C. for 2 hours. The mixture was allowed to cool, diluted with water and extracted with ethyl acetate. The combined extracts were washed with water, dried (MgSO₄) and the solvent removed by evaporation. The residue was purified by column chromatography eluting with methylene chloride/methanol mixtures (100/0 increasing to 95/5) to give 4-(4-chloro-2-fluoroanilino)-6-methoxy-7-(3-(4-pyridyloxy)propoxy)quinazoline (257 mg, 56%). m.p. 138–140° C.

¹H NMR Spectrum: (DMSOd₆) 2.25(m, 2H); 3.92(s, 3H); 4.24(t, 2H); 4.30(t, 2H); 6.98(dd, 2H); 7.20(s, 1H); 7.31(dd, 1H); 7.55(dd, 2H); 7.79(s, 1H); 8.32–8.38(m, 3H); 9.50(s, 1H)

MS - ESI: 455 [MH]⁺

Elemental analysis: Found C 58.4 H 4.7 N 11.8 C₂₃H₂₀N₄O₃ClF 1H₂O Requires C 58.4 H 4.7 N 11.8%

The starting material was prepared as follows:

A mixture of 4-chloropyridine (7 g, 47 mmol), ethylene glycol (17.9 g, 235 mmol) and sodium hydroxide (4.67 g, 195 mmol) in DMSO (80 ml) was heated at 100° C. for 24 hours. Most of the solvent was removed by evaporation and the residue was diluted with ice water. The aqueous mixture was extracted with ethyl acetate, the extracts combined, dried (MgSO₄) and the solvent removed by evaporation. The residue was purified by column chromatography eluting with methylene chloride/methanol mixtures (100/0 increasing to 97/3) to give 4-(3-hydroxypropoxy)pyridine (3.2 g, 45%).

Thionyl chloride (2.2 ml, 30 mmol) was added slowly to a solution of 4-(3-hydroxypropoxy)pyridine (3.1 g, 20 mmol) in trichloromethane (40 ml) at 5° C. The mixture was stirred at 5° C. for 1 hour and then at ambient temperature for 2 hours. The volatiles were removed by evaporation, the residue azeotroped with toluene and dried under vacuum to give 4-(3-chloropropoxy)pyridine hydrochloride (3.81 g, 91%) as a solid.

¹H NMR Spectrum: (DMSOd₆) 2.22(m, 2H); 3.80(t, 2H); 4.42(t, 2H); 7.55(d, 2H); 8.72(d, 2H)

MS - ESI: 172 [MH]⁺

Example 68

A mixture of 4-(4-chloro-2-fluoroanilino)-7-hydroxy-6-methoxyquinazoline (350 mg, 1.0 mmol), (prepared as described for the starting material in Example 24), 4-(2-chloroethylthio)pyridine hydrochloride (252 mg, 1.2 mmol) and potassium carbonate (454 mg, 3.3 mmol) in NMP (30 ml) was heated at 90° C. for 2 hours. The mixture was allowed to cool, diluted with water and extracted with ethyl acetate. The combined extracts were washed with water, dried (MgSO₄) and the solvent removed by evaporation. The residue was purified by column chromatography eluting with ethyl acetate/methanol mixtures (100/0 increasing to 75/25) to give 4-(4-chloro-2-fluoroanilino)-6-methoxy-7-(2-(4-pyridylthio)ethoxy)quinazoline (13 mg, 3%). m.p. 182–186° C.

¹H NMR Spectrum: (DMSOd₆) 3.58(t, 2H); 3.90(s, 3H); 4.40(t, 2H); 7.20(s, 1H); 7.32(d, 1H); 7.40(d, 2H); 7.50–7.60 (m, 2H); 7.80(s, 1H); 8.32(s, 1H); 8.38(d, 2H); 9.57(s, 1H)

MS-ESI: 457 [MH]⁺

The starting material was prepared as follows:

Sodium hydride (890 mg of a 50% suspension in mineral oil, 19 mmol) was added to a solution of 4-mercaptopyridine (2.34 g, 21 mmol) in DMF (75 ml) and the mixture stirred for 30 minutes. 2-(2-Bromoethoxy)tetrahydropyran (4.0 g, 19 mmol), (J. Am. Chem. Soc. 1948, 70, 4187), was added and the mixture heated at 100° C. for 3 hours and then stirred at ambient temperature for 18 hours. The reaction mixture was diluted with water and extracted with ethyl acetate. The combined extracts were washed with water, dried (MgSO₄) and the solvent removed by evaporation. The residue was purified by column chromatography eluting with methylene chloride/methanol mixtures (100/0 increasing to 97/3) to give 4-(2-(tetrahydropyran-2-yloxy)ethylthio)pyridine (2.8 g, 56%).

¹H NMR Spectrum: (DMSOd₆) 1.35–1.64(m, 6H); 3.35–3.42(m, 1H); 3.58–3.82(m, 3H); 4.60(s, 1H); 7.30(dd, 2H); 8.33(dd, 2H)

A solution of 4-(2-(tetrahydropyran-2-yloxy)ethylthio) pyridine (2.73 g, 11 mmol) in acetic acid (8 ml), THF (4 ml) and water (2 ml) was heated at 50° C. for 4 hours. The volatiles were removed by evaporation and the residue azeotroped with toluene to give 4-(2-hydroxyethylthio) pyridine (1.39 g, 79%) as an off-white solid.

¹H NMR Spectrum: (DMSOd₆) 3.10(t, 2H); 3.60(q, 2H); 5.00(t, 1H); 7.22(d, 2H); 8.30(d, 2H)

Thionyl chloride (0.98 ml, 13.5 mmol) was added slowly to a solution of 4-(2-hydroxyethylthio)pyridine (1.39 g, 9.0 mmol) in trichloromethane (25 ml) at 5° C. The mixture was stirred at 5° C. for 1 hour and then at ambient temperature for 2 hours. The volatiles were removed by evaporation, the residue azeotroped with toluene and dried under vacuum to give 4-(2-chloroethylthio)pyridine hydrochloride (500 mg, 26%) as a solid.

¹H NMR Spectrum: (DMSOd₆) 3.65(t, 2H); 3.90(t, 2H); 7.90(d, 2H); 8.60(d, 2H) MS-ESI: 174 [MH]⁺

Example 69

A mixture of 4-(4-chloro-2-fluoroanilino)-7-hydroxy-6-methoxyquinazoline (350 mg, 1.0 mmol), (prepared as described for the starting material in Example 24), 3-(2-chloroethoxy)pyridine hydrochloride (234 mg, 1.2 mmol) and potassium carbonate (456 mg, 3.3 mmol) in NMP (20 ml) was heated at 90° C. for 2 hours. The mixture was allowed to cool, diluted with water and extracted with ethyl acetate. The combined extracts were washed with water, dried (MgSO₄) and the solvent removed by evaporation. The residue was purified by column chromatography eluting with methylene chloride/methanol mixtures (100/0 increasing to 95/5) to give 4-(4-chloro-2-fluoroanilino)-6-methoxy-7-(2-(3-pyridyloxy)ethoxy)quinazoline (95 mg, 20%). m.p. 188–190° C.

¹H NMR Spectrum: (DMSOd₆) 3.90(s, 3H); 4.45(m, 4H); 7.24(s, 1H); 7.18(dd, 1H); 7.42–7.60(m, 3H); 7.80(s, 1H); 8.20(d, 1H); 8.35(s, 2H); 9.50(s, 1H) MS-ESI: 441 [MH]⁺ Elemental analysis: Found C 55.0 H 3.9 N 11.8 C₂₂H₁₈N₄O₃ClF 2H₂O Requires C 55.4 H 4.6 N 11.7%

The starting material was prepared as follows:

Sodium hydride (1.02 g of a 50% suspension in mineral oil, 42 mmol) was added to a solution of 3-hydroxypyridine (2.01 g, 21 mmol) in DMF (50 ml) and the mixture stirred for 30 minutes. 2-(2-Bromoethoxy)tetrahydropyran (4.0 g, 19 mmol), (J. Am. Chem. Soc. 1948, 70, 4187), was added and the mixture heated at 100° C. for 3 hours and then stirred at ambient temperature for 18 hours. The reaction mixture was diluted with water and extracted with ethyl acetate. The combined extracts were washed with water, dried (MgSO₄) and the solvent removed by evaporation. The residue was purified by column chromatography eluting with methylene chloride/methanol mixtures (100/0 increasing to 97/3) to give 3-(2-(tetrahydropyran-2-yloxy)ethoxy)pyridine (2.28 g, 48%).

¹H NMR Spectrum: (DMSOd₆) 1.38–1.65(m, 6H); 3.40 (m, 1H); 3.65–3.79(m, 2H); 3.85–3.95(m, 1H); 4.20(t, 2H); 4.62(s, 1H); 7.30(dd, 1H); 7.39(dd, 1H); 8.15(d, 1H); 8.28(d, 1H) MS-ESI: 224 [MH]⁺

A solution of 3-(2-(tetrahydropyran-2-yloxy)ethoxy) pyridine (1.54 g, 7 mmol) in acetic acid (8 ml), THF (4 ml) and water (2 ml) was heated at 50° C. for 4 hours. The volatiles were removed by evaporation and the residue azeotroped with toluene to give 3-(2-hydroxyethoxy) pyridine (820 mg, 86%) as an off-white solid.

¹H NMR Spectrum: (DMSOd₆) 3.70(t, 2H); 4.05(t, 2H); 4.85(s, 1H); 7.25(dd, 1H); 7.37(dd, 1H); 8.10(d, 1H); 8.24(d, 1H) MS-ESI: 140 [MH]⁺

Thionyl chloride (0.89 ml, 12 mmol) was added slowly to a solution of 3-(2-hydroxyethoxy)pyridine (1.13 g, 8 mmol) in trichloromethane (20 ml) at 5° C. The mixture was stirred at 5° C. for 1 hour and then at ambient temperature for 2 hours. The volatiles were removed by evaporation, the residue azeotroped with toluene and dried under vacuum to give 3-(2-chloroethoxy)pyridine hydrochloride (300 mg, 19%) as a solid.

¹H NMR Spectrum: (DMSOd₆) 3.99(t, 2H); 4.42(t, 2H); 7.82(dd, 1H); 8.05(dd, 1H); 8.42(d, 1H); 8.62(s, 1H)

Example 70

2-Fluoro-5-hydroxy-4-methylaniline (170 mg, 1.2 mmol), (prepared as described for the starting material in Example 13), was added to a solution of 7-benzyloxy-4-chloroquinazoline hydrochloride (307 mg, 1 mmol) in 2-pentanol (5 ml) and the mixture stirred at 120° C. for 2 hours. The mixture was allowed to cool and the resulting precipitate was collected by filtration, washed with isopropanol and then ether and dried under vacuum at 70° C. to give 7-benzyloxy-4-(2-fluoro-5-hydroxy-4-methylanilino) quinazoline hydrochloride (331 mg, 80%).

¹H NMR Spectrum: (DMSOd₆) 2.16(s, 3H); 5.36(s, 2H); 6.88(d, 1H); 7.12(d, 1H); 7.3–7.65(m, 7H); 8.68(d, 1H); 8.82(s, 1H); 9.68(s, 1H); 11.4(s, 1H) MS-ESI: 376 [MH]⁺ Elemental analysis: Found C 63.7 H 4.8 N 10.0 C₂₂H₁₈N₃O₂F 1HCl Requires C 64.2 H 4.7 N 10.2%

The starting material was prepared as follows:

Sodium (368 mg, 16 mmol) was added to benzyl alcohol (10 ml, 96 mmol) and the mixture was heated at 148° C. for 30 minutes. 7-Fluoro-3,4-dihydroquinazolin-4-one (656 mg, 4 mmol), (J. Chem. Soc. section B 1967, 449), was added and the mixture maintained at 148° C. for 24 hours. The reaction mixture was allowed to cool, the solution was poured on to water (170 ml) and the aqueous mixture adjusted to pH3 with concentrated hydrochloric acid. The precipitate was collected by filtration, washed with water, ether and dried under vacuum to give 7-benzyloxy-3,4-dihydroquinazolin-4-one (890 mg, 89%) as a white solid. m.p. 267–269° C.

¹H NMR Spectrum: (DMSOd₆; CF₃COOD) 5.32(s, 2H); 7.25(d, 1H); 7.32–7.52(m, 6H); 8.12(d, 1H); 8.99(s, 1H) MS-ESI: 252 [MH]⁺ Elemental analysis: Found C 71.4 H 4.9 N 10.7 C₁₅H₁₂N₂O₂0.04H₂O Requires C 71.2 H 4.8 N 11.1%

A mixture of 7-benzyloxy-3,4-dihydroquinazolin-4-one (800 mg, 3.17 mmol) and DMF (100 μl) in thionyl chloride (20 ml, 0.27 mmol) was heated at reflux for 3 hours. Excess thionyl chloride was removed by evaporation and the residue azeotroped with toluene and dried under vacuum to give 7-benzyloxy-4-chloroquinazoline hydrochloride (835 mg, 86%) as a cream solid. m.p. 131–132° C.

¹H NMR Spectrum: (DMSOd₆; CF₃COOD) 5.32(s, 2H); 7.29(d, 1H); 7.34–7.52(m, 6H); 8.12(d, 1H); 9.03(s, 1H) MS-ESI: 270 [MH]⁺

Example 71

Using an analogous procedure to that described in Example 70, 7-benzyloxy-4-chloroquinazoline hydrochloride (307 mg, 1 mmol), (prepared as described for the starting material in Example 70), was treated with 4-chloro-2-fluoro-5-hydroxyaniline (193 mg, 1.2 mmol), (EP 061741 A2), to give 7-benzyloxy-4-(4-chloro-2-fluoro-5-hydroxyanilino)quinazoline hydrochloride (407 mg, 94%). m.p. 253–257° C.

¹H NMR Spectrum: (DMSOd₆) 5.37(s, 2H); 7.16(d, 1H); 7.32–7.5(m, 4H); 7.54(s, 1H); 7.56(d, 2H); 7.59(dd, 1H); 8.73(d, 1H); 8.86(s, 1H); 10.63(br s, 1H); 11.6(br s, 1H) MS-ESI: 396 [MH]⁺ Elemental analysis: Found C 57.8 H 3.8 N 9.7 C₂₁H₁₅N₃O₂ClF 0.3H₂O 1HCl Requires C 57.6 H 3.8 N 9.6%

Example 72

Using an analogous procedure to that described in Example 36, 4-(2-fluoro-5-methoxycarbonyloxy-4-methylanilino)-7-hydroxy-6-methoxyquinazoline hydrochloride (224 mg, 0.6 mmol), (prepared as described for the starting material in Example 22), was treated with 4-bromomethyl-1,2-difluorobenzene (149 mg, 0.72 mmol) to give 7-(3,4-dilluorobenzyloxy)-4-(2-fluoro-5-hydroxy-4-methylanilino)-6-methoxyquinazoline hydrochloride (90 mg, 31%).

¹H NMR Spectrum: (DMSOd₆) 2.17(s, 3H); 4.0(s, 3H); 5.33(s, 2H); 6.88(d, 1H); 7.11(d,1H); 7.38(s, 1H); 7.41(m, 1H); 7.55(m, 1H); 7.62(m, 1H); 8.17(s, 1H); 8.75(s, 1H); 9.68(s, 1H); 11.15(s, 1H) MS-ESI: 442 [MH]⁺ Elemental analysis: Found C 58.0 H 4.3 N 8.7 C₂₃H₁₈N₃O₃F₃ 0.9HCl 0.08 isopropanol Requires C 58.3 H 4.1 N 8.8

Example 73

Tetrabutylammonium fluoride (563 μl of a 1M solution in THF, 0.62 mmol) was added to a solution of 4-(4-chloro-5-diphenyl-t-butylsilyloxy-2-fluoroanilino)-6-methoxy-7-((1-methylimidazol-2-yl)methoxy)quinazoline (207 mg, 0.31 mmol) in THF (5 ml) cooled at 5° C. and the mixture was then stirred for 1 hour at ambient temperature. Water was added and the volatiles were removed by evaporation.

The solid residue was dissolved in methylene chloride/methanol and a 5M solution of hydrogen chloride in isopropanol (0.3 ml) was added. The solvent was removed by evaporation, the solid residue was resuspended in ether, collected by filtration, washed with ether and dried under vacuum to give 4-(4-chloro-2-fluoro-5-hydroxyanilino)-6-methoxy-7-((1-methylimidazol-2-yl)methoxy)quinazoline hydrochloride (99 mg, 63%).

$^1$H NMR Spectrum: (DMSOd6) 3.93(s, 3H); 4.01(s, 3H); 5.67(s, 2H); 7.16(d, 1H); 7.52(d, 1H); 7.58(s, 1H); 7.70(s, 1H); 7.78(s, 1H); 8.31(s, 1H); 8.8(s, 1H); 10.58(s, 1H); 11.35(brs, 1H) MS-ESI: 430 [MH]$^+$ Elemental analysis: Found C 45.8 H 4.3 N 12.9 $C_{20}H_{17}N_5O_3ClF$ 1.4$H_2O$ 2HCl Requires C 45.5 H 4.2 N 13.3%

The starting material was prepared as follows:

Diethyl azodicarboxylate (219 μl, 1.4 mmol) was added dropwise to a solution of 4-(4-chloro-5-diphenyl-t-butylsilyloxy-2-fluoroanilino)-7-hydroxy-6-methoxyquinazoline (400 mg, 0.7 mmol), (prepared as described for the starting material in Example 33), 2-hydroxymethyl-1-methylimidazole (82 mg, 0.83 mmol), (J. Chem. Soc. 1927, 3128–3136), and triphenylphosphine (365 mg, 1.4 mmol) in methylene chloride (12 ml) cooled at 0° C. The mixture was stirred for 1 hour at ambient temperature and further 2-hydroxymethyl-1-methylimidazole (68 mg, 0.69 mmol), triphenylphosphine (91 mg, 0.34 mmol) and diethyl azodicarboxylate (54 μl, 0.34 mmol) were added. The mixture was stirred for 1 hour at ambient temperature and the solvent was removed by evaporation. The residue was purified by column chromatography eluting with methylene chloride/methanol (94/6) to give 4-(4-chloro-5-diphenyl-t-butylsilyloxy-2-fluoroanilino)-6-methoxy-7-((1-methylimidazol-2-yl)methoxy)quinazoline (116 mg, 25%).

$^1$H NMR Spectrum: (CDCl$_3$) 1.16(s, 9H); 3.75(s, 3H); 3.93(s, 3H); 5.28(s, 2H); 6.84(s, 1H); 6.91(s, 1H); 7.02(s, 1H); 7.17(d, 1H); 7.32–7.48(m, 8H); 7.78(2d, 4H); 8.08(s, 1H); 8.18(d, 1H)

Example 74

A mixture of 4-(2-fluoro-5-methoxycarbonyloxy-4-methylanilino)-7-hydroxyquinazoline hydrochloride (400 mg, 0.98 mmol), 2-chloromethyl-1-methylimidazole hydrochloride (210 mg, 1.25 mmol), potassium carbonate (580 mg, 4.2 mmol) and potassium iodide (17 mg, 0.1 mmol) in DMF (20 ml) was stirred at 65° C. for 4.5 hours followed by 17 hours at ambient temperature. The solvent was removed by evaporation and the residue was partitioned between ethyl acetate and water. The organic layer was separated, washed with water, brine, dried (MgSO$_4$) and the solvent removed by evaporation. The solid residue was purified by column chromatography eluting with methylene chloride/methanol (97/3) to give a yellow solid (258 mg). This solid was dissolved in methanol (5 ml) and a 1M aqueous sodium hydroxide solution (660 μl, 0.66 mmol) was added. The mixture was stirred for 15 minutes, then water was added and the mixture adjusted to pH7 with concentrated hydrochloric acid. The aqueous mixture was extracted with ethyl acetate and the combined organic extract was washed with water, brine, dried (MgSO$_4$) and the solvent removed by evaporation. The residue was purified by flash chromatography eluting with methylene chloride/methanol (95/5). The purified solid product was dissolved in methanol and methanolic hydrogen chloride (1.5 ml of a 7.5M solution) was added. The volatiles were removed by evaporation, the solid residue was suspended in pentane, collected by filtration, washed with pentane and dried under vacuum to give 4-(2-fluoro-5-hydroxy-4-methylanilino)-7-((1-methylimidazol-2-yl)methoxy)quinazoline hydrochloride (105 mg, 44%).

$^1$H NMR Spectrum: (DMSOd$_6$) 2.16(s, 3H); 3.92(s, 3H); 5.71(s, 2H); 6.90(d, 1H); 7.1(d, 1H); 7.52(d, 1H); 7.64(d, 1H); 7.71(s, 1H); 7.78(s, 1H); 8.77(d, 1H); 8.82(s, 1H); 9.7(br s, 1H); 11.45(br s, 1H) MS-ESI: 380 [MH]$^+$ Elemental analysis: Found C 52.2 H 5.0 N 15.1 $C_{20}H_{18}N_5O_2F$ 0.9$H_2O$ 1.8HCl Requires C 52.1 H 4.7 N 15.2%

The starting material was prepared as follows:

Sodium (368 mg, 16 mmol) was added to benzyl alcohol (10 ml, 96 mmol) and the mixture was heated at 148° C. for 30 minutes, 7-fluoro-3,4-dihydroquinazolin-4-one (656 mg, 4 mmol), (J. Chem. Soc. section B 1967, 449), was added and the mixture maintained at 148° C. for 24 hours. The reaction mixture was allowed to cool, the solution was poured on to water (170 ml) and the aqueous mixture adjusted to pH3 with concentrated hydrochloric acid. The precipitate was collected by filtration, washed with water, then ether and dried under vacuum to give 7-benzyloxy-3,4-dihydroquinazolin-4-one (890 mg, 89%) as a white solid. m.p. 267–269° C.

$^1$H NMR Spectrum: (DMSOd$_6$; CF$_3$COOD) 5.32(s, 2H); 7.25(d, 1H); 7.32–7.52(m, 6H); 8.12(d, 1H); 8.99(s, 1H) MS-ESI: 252 [MH]$^+$ Elemental analysis: Found C 71.4 H 4.9 N 10.7 $C_{15}H_{12}N_2O_2$ 0.04$H_2O$ Requires C 71.2 H 4.8 N 11.1%

A mixture of 7-benzyloxy-3,4-dihydroquinazolin-4-one (800 mg, 3.17 mmol) and DMF (100 μl) in thionyl chloride (20 ml, 0.27 mmol) was heated at reflux for 3 hours. Excess thionyl chloride was removed by evaporation and the residue azeotroped with toluene and dried under vacuum to give 7-benzyloxy-4-chloroquinazoline hydrochloride (835 mg, 86%) as a cream solid. m.p. 131–132° C.

$^1$H NMR Spectrum: (DMSOd$_6$; CF$_3$COOD) 5.32(s, 2H); 7.29(d, 1H); 7.34–7.52(m, 6H); 8.12(d, 1H); 9.03(s, 1H) MS-ESI: 270 [MH]$^+$ 2-Fluoro-5-methoxycarbonyloxy-4-methylaniline (883 mg, 4.4 mmol), (prepared as described for the starting material in Example 12), was added to a solution of 7-benzyloxy4-chloroquinazoline hydrochloride (1 g, 3.7 mmol) in 2-pentanol (15 ml) at 120° C. and the mixture was then heated at reflux for 4 hours. The mixture was allowed to cool and the precipitate was collected by filtration, washed with isopropanol followed by ether and dried under vacuum to give 7-benzyloxy-4-(2-fluoro-5-methoxycarbonyloxy-4-methylanilino)quinazoline hydrochloride (1.65 g, 97%) as a cream solid. m.p. 219–220° C.

$^1$H NMR Spectrum: (DMSOd$_6$) 2.22(s, 3H); 3.86(s, 3H); 5.37(s, 2H); 7.30–7.60(m, 9H); 8.60(d, 1H); 8.80(s, 1H); 11.2(s, 1H) MS-ESI: 434 [MH]$^+$ Elemental analysis: Found C 60.1 H 4.9 N 8.5 $C_{24}H_{20}N_3O_4F$ 1HCl 0.5$H_2O$ Requires C 60.2 H 4.6 N 8.8%

7-Benzyloxy-4-(2-fluoro-5-methoxycarbonyloxy-4-methylanilino)quinazoline hydrochloride (1.53 g, 3.25 mmol) and 10% palladium-on-charcoal catalyst (180 mg) in a mixture of methanol (75 ml), DMF (6 ml) and trichloromethane (30 ml) was stirred under hydrogen at 1.5 atmospheres pressure for 45 minutes. The catalyst was removed by filtration through diatomaceous earth and the solvent removed from the filtrate by evaporation. The residue was triturated with ether, the resulting solid was collected by filtration and dried under vacuum to give 4-(2-fluoro-5-methoxycarbonyloxy-4-methylanilino)-7-hydroxyquinazoline hydrochloride (1.23 g, 84%) as an orange solid. m.p. 205–210° C.

¹H NMR Spectrum: (DMSOd₆) 2.22(s, 3H); 3.85(s, 3H); 7.24(d, 1H); 7.35(dd, 1H); 7.42(d, 1H); 7.45(d, 1H); 8.58(d, 1H); 8.81(s, 1H); 11.40(s, 1H); 11.76(s, 1H) MS-ESI: 344 [MH]⁺

Example 75

Diethyl azodicarboxylate (244 mg, 1.4 mmol) was added dropwise to a suspension of 4-(2-fluoro-5-methoxycarbonyloxy-4-methylanilino)-7-hydroxy-6-methoxyquinazoline hydrochloride (261 mg, 0.7 mmol), (prepared as described for the starting material in Example 22), triphenylphosphine (367 mg, 1.4 mmol) and 2-(1,2,4-triazol-1-yl)ethanol (95 mg, 0.84 mmol), (Ann. Pharm. Fr. 1977, 35, 503–508), in methylene chloride (5 ml). The mixture was stirred for 1 hour at ambient temperature and further triphenylphosphine (184 mg, 0.7 mmol), 2-(1,2,4-triazol-1-yl)ethanol (63 mg, 0.56 mmol) and diethyl azodicarboxylate (122 mg, 0.7 mmol) were added. The mixture was stirred for a further 2.5 hours and the solvent was removed by evaporation. The residue was dissolved in methanol (5 ml) and 2M aqueous sodium hydroxide solution (2 ml) was added. The mixture was stirred for 20 minutes and the mixture was partitioned between ether and water. The aqueous layer was acidified to pH7 with 2M hydrochloric acid and the resulting precipitate was collected by filtration, washed with water, and dried under vacuum. The resulting solid was dissolved in methylene chloride/methanol and a 5M solution of hydrogen chloride in isopropanol (0.5 ml) was added. The volatiles were removed by evaporation, the solid was resuspended in ether, collected by filtration, washed with ether and dried under vacuum to give 4-(2-fluoro-5-hydroxy-4-methylanilino)-7-(2-(1,2,4-triazol-1-yl)ethoxy)quinazoline hydrochloride (180 mg, 56%).

¹H NMR Spectrum: (DMSOd₆) 2.16(s, 3H); 3.97(s, 3H); 4.59(t, 2H); 4.74(t, 2H); 6.9(d, 1H); 7.10(d, 1H); 7.37(s, 1H); 8.03(s, 1H); 8.23(s, 1H); 8.62(s, 1H); 8.79(s, 1H); 9.7(br s, 1H); 11.4(s, 1H) MS-ESI: 411 [MH]⁺ Elemental analysis: Found C 53.2 H 4.8 N 18.4 C₂₀H₁₉N₆O₃F 0.1H₂O 1.2HCl Requires C 52.7 H 4.5 N 18.4%

Example 76

Tetrabutylammonium fluoride (608 μl of a 1M solution in THF, 0.67 mmol) was added to a solution of 4-(4-chloro-5-diphenyl-t-butylsilyloxy-2-fluoroanilino)-6-methoxy-7-((3-thienyl)methoxy)quinazoline (224 mg, 0.33 mmol) in THF (5 ml) cooled at 5° C. After stirring for 1 hour at ambient temperature, water was added. The THF was removed by evaporation. The precipitate was collected by filtration and dried by azeotroping with ethanol. The solid was dissolved in methylene chloride/methanol and a solution of 5M hydrochloric acid in isopropanol was added. The volatiles were removed by evaporation. The residue was suspended in ether, collected by filtration, washed with ether and dried under vacuum to give 4-(4-chloro-2-fluoro-5-hydroxyanilino)-6-methoxy-7-((3-thienyl)methoxy)quinazoline hydrochloride (132 mg, 85%). m.p. 277–281° C.

¹H NMR Spectrum: (DMSOd₆) 3.99(s, 3H); 5.34(s, 2H); 7.15(d, 1H); 7.26(d, 1H); 7.49(s, 1H); 7.53(d, 1H); 7.61(m, 1H); 7.75(s, 1H); 8.22(s, 1H); 8.8(s, 1H); 10.59(s, 1H); 11.38(br s, 1H) MS-ESI: 432 [MH]⁺ Elemental analysis: Found C 51.0 H 3.5 N 8.9 C₂₀H₁₅N₃O₃ClFS 0.1H₂O 1HCl Requires C 51.1 H 3.5 N 8.9%

The starting material was prepared as follows:

Diethyl azodicarboxylate (274 μl, 1.7 mmol) was added dropwise to a solution of 4-(4-chloro-5-diphenyl-t-butylsilyloxy-2-fluoroanilino)-7-hydroxy-6-methoxyquinazoline (400 mg, 0.7 mmol), (prepared as described for the starting material in Example 33), 3-thiophenemethanol (119 mg, 1 mmol) triphenylphosphine (456 mg, 1.7 mmol) in methylene chloride (12 ml) cooled at 0° C. The mixture was stirred for 2 hours at ambient temperature, the solvent was removed by evaporation and the residue was purified by column chromatography eluting with methylene chloride/ether (95/5). The purified product was triturated with petroleum ether/ethyl acetate (8/2) and the solid product was collected by filtration, washed with ether and dried under vacuum to give 4-(4-chloro-5-diphenyl-t-butylsilyloxy-2-fluoroanilino)-6-methoxy-7-((3-thienyl)methoxy)quinazoline (223 mg, 47%).

¹H NMR Spectrum: (DMSOd₆) 1.09(s, 9H); 3.85(s, 3H); 5.23(s, 2H); 7.04(d, 1H); 7.21(d, 1H); 7.25(s, 1H); 7.4–7.5 (m, 6H); 7.58(m, 2H); 7.62–7.75(m, 6H); 8.1(s, 1H); 9.22(br s, 1H)

Example 77

Diethyl azodicarboxylate (274 μl, 1.7 mmol) was added dropwise to a solution of 4-(4-chloro-5-diphenyl-t-butylsilyloxy-2-fluoroanilino)-7-hydroxy-6-methoxyquinazoline (400 mg, 0.7 mmol), (prepared as described for the starting material in Example 33), triphenylphosphine (456 ml, 1.7 mmol), 2-(4-pyridyl)ethanol (128 mg, 1 mmol), (Zhur. Obshchei. Khim. 1958, 28, 103–110), in methylene chloride (12 ml) cooled at 0° C. The mixture was stirred for 2 hours at ambient temperature and the solvent was removed by evaporation. The residue was purified by column chromatography eluting with methylene chloride/methanol (97/3) to give a white solid (416 mg). A portion of this solid (390 mg) was dissolved in THF (6 ml), the solution was cooled to 0° C. and tetrabutylammonium fluoride (1.1 ml of a 1M solution in THF, 1.1 mmol) was added and the mixture was stirred for 2 hours at ambient temperature. Water was added, the organic solvent was removed by evaporation and the resulting precipitate was collected by filtration. The solid was dissolved in methylene chloride/methanol and a 5M solution of hydrogen chloride in isopropanol (0.5 ml) was added. The volatiles were removed by evaporation and the solid was resuspended in isopropanol and collected by filtration, washed with isopropanol and ether and dried under vacuum to give 4-(4-chloro-2-fluoro-5-hydroxyanilino)-6-methoxy-7-(2-(4-pyridyl)ethoxy)quinazoline hydrochloride (123 mg, 42%).

¹H NMR Spectrum: (DMSOd₆; CD₃COOD) 3.49(t, 2H); 3.99(s, 3H); 4.6(t, 2H); 7.16(d, 1H); 7.41(s, 1H); 7.51(d, 1H); 8.05(br s, 2H); 8.19(s, 1H); 8.84(s, 1H); 8.86(br s, 2H) MS-ESI: 441 [MH]⁺ Elemental analysis: Found C 50.4 H 4.7 N 10.0 C₂₂H₁₈N₄O₃ClF 1.1H₂O 1.8HCl Requires C 50.5 H 4.5 N 10.4% 0.23 isopropanol Example 78

Using an analogous procedure to that described in Example 77, 4-(4-chloro-5-diphenyl-t-butylsilyloxy-2-fluoroanilino)-7-hydroxy-6-methoxyquinazoline (300 mg, 0.52 mmol), (prepared as described for the starting material in Example 33), was treated with 4-hydroxymethyl-2-methylthiazole (100 mg, 0.87 mmol) to give 4-(4-chloro-2-fluoro-5-hydroxyanilino)-6-methoxy-7-((2-methylthiazol-4-yl)methoxy)quinazoline hydrochloride (132 mg, 52%).

¹H NMR Spectrum: (DMSOd₆) 2.68(s, 3H); 4.00(s, 3H); 5.35(s, 2H); 7.17(d, 1H); 7.52(d, 1H); 7.56(s, 1H); 7.72(s, 1H); 8.29(s, 1H); 8.83(s, 1H); 10.63(br s, 1H); 11.58(s, 1H) MS-ESI: 447 [MH]⁺ Elemental analysis: Found C 48.2 H 3.7 N 11.2 $C_{20}H_{16}N_4O_3ClFS$ 0.6$H_2O$ 1.2HCl Requires C 47.9 H 3.7 N 11.2%

The starting material was prepared as follows:

A solution of 4-chloromethyl-2-methylthiazole (1.84 g, 10 mmol) in water (9 ml) and concentrated hydrochloric acid (2 ml) was heated at reflux for 20 hours. The mixture was allowed to cool and was adjusted to pH5 with 2M aqueous sodium hydroxide solution and the mixture was extracted with ethyl acetate. The organic extract was washed with water and brine, dried (MgSO$_4$) and the solvent removed by evaporation. The residue was purified by column chromatography eluting with methylene chloride/methanol (97/3) to give 4-hydroxymethyl-2-methylthiazole (800 mg, 54%).

$^1$H NMR Spectrum (CDCl$_3$) 2.72(s, 3H); 2.92(br s, 1H); 4.73(s, 2H); 7.03(s, 1H)

Example 79

Diethyl azodicarboxylate (197 μl, 1.2 mmol) was added dropwise to a solution of 4-(4-chloro-2-fluoroanilino)-7-hydroxy-6-methoxyquinazoline (200 mg, 0.6 mmol), (prepared as described for the starting material in Example 24), 3-thiophenemethanol (107 mg, 0.93 mmol) and triphenylphosphine (328 mg, 1.2 mmol) in methylene chloride (6 ml) cooled at 0° C. The mixture was stirred for 2 hours at ambient temperature and further triphenylphosphine (157 mg, 0.57 mmol), 3-thiophenemethanol (107 mg, 0.93 mmol) and diethyl azodicarboxylate (98.5 μl, 0.59 mmol) were added. The mixture was stirred for 2 hours at ambient temperature and the solvent was removed by evaporation. The residue was dissolved in ethyl acetate and the solution was washed with water and brine, dried (MgSO$_4$) and the solvent removed by evaporation. The residue was purified by column chromatography eluting with methylene chloride/ethyl acetate (4/6). The resulting oil was dissolved in ether and a 5M solution of hydrogen chloride in isopropanol (1 ml) was added. The resulting precipitate was collected by filtration, washed with ether and dried under vacuum to give 4-(4-chloro-2-fluoroanilino)-6-methoxy-7-((3-thienyl)methoxy)quinazoline hydrochloride (59 mg, 20%).

$^1$H NMR Spectrum: (DMSOd$_6$) 3.99(s, 3H); 5.34(s, 2H); 7.25(d, 1H); 7.43(d, 1H); 7.45(s, 1H); 7.58–7.63(m, 2H); 7.7(dd, 1H); 7.72(dd, 1H); 8.17(s, 1H); 8.78(s, 1H) MS-ESI: 416 [MH]$^+$ Elemental analysis: Found C 53.5 H 3.7 N 9.0 $C_{20}H_{15}N_3O_2CFS$ 0.95HCl Requires C 53.3 H 3.6 N 9.3%

Example 80

A mixture of 4-(4-chloro-2-fluoroanilino)-7-hydroxy-6-methoxyquinazoline (250 mg, 0.78 mmol), (prepared as described for the starting material in Example 24), 2-acetamido-4-chloromethylthiazole (164 mg, 0.86 mmol) and potassium carbonate (216 mg, 1.5 mmol) in DMF (5 ml) was stirred at 40° C. for 7 hours. The mixture was partitioned between ethyl acetate and water and the aqueous layer was adjusted to pH7 with 2M hydrochloric acid. The organic phase was washed with water, brine, dried (MgSO$_4$) and the solvent removed by evaporation. The residue was purified by column chromatography eluting with methylene chloride/methanol (95/5). The purified solid was dissolved in a mixture of methylene chloride and methanol and a 5M solution of hydrogen chloride in isopropanol (1.0 ml) was added. The volatiles were removed by evaporation to give a solid, which was triturated with ether, collected by filtration and dried under vacuum to give 7-((2-acetamidothiazol-4-yl)methoxy)-4-(4-chloro-2-fluoroanilino)-6-methoxyquinazoline hydrochloride (96 mg, 24%). m.p. 194–202° C.

$^1$H NMR Spectrum: (DMSOd$_6$) 2.14(s, 3H); 4.0(s, 3H); 5.31 (s, 2H); 7.34(s, 1H); 7.45(dd, 1H); 7.52(s, 1H); 7.60(t, 1H); 7.68(dd, 1H); 8.30(s, 1H); 8.81(s, 1H) MS-ESI: 474 [MH]$^+$ Elemental analysis: Found C 46.9 H 3.8 N 13.2 $C_{21}H_{17}N_5O_3ClFS$ 1.1$H_2O$ 1.1HCl Requires C 47.3 H 3.8 N 13.1%

Example 81

Diethyl azodicarboxylate (295 μl, 1.8 mmol) was added dropwise to a solution of 4-(4-chloro-2-fluoroanilino)-7-hydroxy-6-methoxyquinazoline (300 mg, 0.93 mmol), (prepared as described for the starting material in Example 24), 2-(1,2,4-triazol-1-yl)ethanol (159 mg, 1.4 mmol), (Ann. Pharm. Fr. 1977, 35, 503–508), and triphenylphosphine (492 mg, 1.8 mmol) in methylene chloride (10 ml). The mixture was stirred for 2 hours at ambient temperature and further triphenylphosphine (246 mg, 0.9 mmol) and diethyl azodicarboxylate (147 μl, 0.9 mmol) were added. The mixture was stirred for 1 hour at ambient temperature and the resulting precipitate was collected by filtration, washed with methylene chloride and ether and dried under vacuum. This solid was suspended in methylene chloride/methanol and a 5M solution of hydrogen chloride in isopropanol (1.0 ml) was added. The volatiles were removed by evaporation, the residue was triturated with ether. The resulting solid was collected by filtration, washed with ether and dried under vacuum to give 4-(4-chloro-2-fluoroanilino)4-methoxy-7-(2-(1,2,4-triazol-1-yl)ethoxy)quinazoline hydrochloride (219 mg, 52%). m.p. 169–174° C.

$^1$H NMR Spectrum: (DMSOd$_6$) 3.99(s, 3H); 4.60(t, 2H); 4.74(t, 2H); 7.43(d, 1H); 7.45(s, 1H); 7.59(t, 1H); 7.67(dd, 1H); 8.06(s, 1H); 8.41(s, 1H); 8.68(s, 1H); 8.83(s, 1H) MS-ESI: 415 [MH]$^+$ Elemental analysis: Found C 47.0 H 4.3 N 16.5 $C_{19}H_{16}N_6O_2ClF$ 1.6 1$H_2O$ 1HCl Requires C 47.0 H 4.4 N 16.4% 0.35 isopropanol

Example 82

Diethyl azodicarboxylate (295 μl, 1.8 mmol) was added dropwise to a solution of 1-(3-hydroxypropyl)-[1,2,4]-triazole (119 mg, 0.93 mmol), (EP0060696 A1), 4-(4-chloro-2-fluoroanilino)-7-hydroxy-6-methoxyquinazoline (200 mg, 0.62 mmol), (prepared as described for the starting material in Example 24), and triphenylphosphine (492 g. 1.8 mmol) in methylene chloride (4 ml) and the mixture stirred for 3 hours at ambient temperature. The mixture was purified by column chromatography eluting with methylene chloride/acetonitrile/methanol (60/32/8). The purified product was triturated with a mixture of pentane and ether, collected by filtration and dried under vacuum to give a white solid. This solid was dissolved in methylene chloride/methanol and ethereal hydrogen chloride (1 ml of a 5M solution) was added. The volatiles were removed by evaporation. The solid residue was suspended in ether, collected by filtration, washed with ether and dried under vacuum to give 4-(4-chloro-2-fluoroanilino)-6-methoxy-7-(3-(1,2,4-triazol-1-yl)propoxy)quinazoline hydrochloride (121 mg, 39%).

$^1$H NMR Spectrum: (DMSOd$_6$; CF$_3$COOD) 2.44(t, 2H); 4.0(s, 3H); 4.3(t, 2H); 4.5(t, 2H); 7.32(s, 1H); 7.47(dd, 1H); 7.62(t, 1H); 7.70(dd, 1H); 8.08(s, 1H); 8.41(s, 1H); 8.87(s, 1H); 9.10(s, 1H) MS-ESI: 429 [MH]$^+$ Elemental analysis: Found C 47.8 H 4.2 N 16.6 $C_{20}H_{18}N_6O_2ClF$ 0.2$H_2O$ 2HCl Requires C 47.5 H 4.1 N 16.6%

Example 83

Diethyl azodicarboxylate (209 mg, 1.2 mmol) was added dropwise to a suspension of 4-(4-chloro-2-fluoroanilino)-7- hydroxy-6-methoxyquinazoline (128 mg, 0.4 mmol), (prepared as described for the starting material in Example 24), triphenylphosphine (314 mg, 1.2 mmol) and 2-(N-methyl-N-(pyridazin-4-yl)amino)ethanol (80 mg, 0.52 mmol) in methylene chloride (5 ml) and the mixture stirred for 2 hours at ambient temperature. The solvent was removed by evaporation, the residue was triturated with ether and the resulting solid was collected by filtration. The solid was purified by column chromatography eluting with methylene chloride/methanol (9/1 followed by 8/2) to give a white solid. This solid was dissolved in methylene chloride/methanol and ethereal hydrogen chloride (0.5 ml of a 4M solution) was added. The volatiles were removed by evaporation, the residue was triturated with ether, collected by filtration and dried under vacuum to give 4-(4-chloro-2-fluoroanilino)-6-methoxy-7-(2-(N-methyl-N-(pyridazin-4-yl)amino)ethoxy)quinazoline hydrochloride (110 mg, 60%).

$^1$H NMR Spectrum: (DMSOd$_6$) 3.11(s, 3H); 3.89(s, 3H); 3.94(t, 2H); 4.37(t, 2H); 6.85(dd, 1H); 7.21(s, 1H); 7.35(dd, 1H); 7.55(dd, 1H); 7.59(t, 1H); 7.8(s, 1H); 8.36(s, 1H); 8.59(d, 1H); 8.90(d, 1H); 9.57(s, 1H) Elemental analysis: Found C 47.2 H 4.6 N 14.7 C$_{22}$H$_{20}$N$_6$O$_2$ClF 1.5H$_2$O 2.15HCl Requires C 47.2 H 4.5 N 15.0%

The starting material was prepared as follows:

A solution of 4-bromo-3,6-dichloro-pyridazine (1.11 g, 5 mmol). (J. Chem. Soc., Perkin Trans I, 1974, 696), and 2-(methylamino)ethanol (0. 75 g, 10 mmol) in isopropanol (10 ml) was heated at reflux for 30 minutes. The solvent was removed by evaporation, the residue was partitioned between methylene chloride and water and the aqueous layer was adjusted to pH9 with solid potassium carbonate. The organic layer was separated, washed with brine, dried (MgSO$_4$) and the solvent removed by evaporation. The residue was triturated with ether, collected by filtration and dried under vacuum to give 2-(N-(3,6-dichloropyridazin-4-yl)-N-methylamino)ethanol (1 g, 90%).

$^1$H NMR Spectrum: (CDCl$_3$) 2.1(br s, 1H); 3.09(s, 3H); 3.71(t, 2H); 3.93(t, 2H); 6.8(s, 1H) MS-ESI: 221 [MH]$^+$ A mixture of 2-(N-(3,6-dichloropyridazin-4-yl)-N-methylamino)ethanol (444 mg, 2 mmol) and 10% palladium-on-charcoal catalyst (150 mg) in ethanol (15 ml), methanol (5 ml) and aqueous ammonia (15 ml) was stirred under hydrogen at 3 atmospheres pressure for 4 hours. The catalyst was removed by filtration and the solvent removed from the filtrate by evaporation. The residue was dissolved in methylene chloride, the insoluble material was removed by filtration and the solvent was removed from the filtrate by evaporation. The residue was purified by column chromatography on neutral aluminum oxide eluting with methylene chloride/methanol (95/5 followed by 90/10). The purified product was triturated with petroleum ether, the solid product was collected by filtration and dried under vacuum to give 2-(N-methyl-N-(pyridazin-4-yl)amino)ethanol (275 mg, 91%).

$^1$H NMR Spectrum: (CDCl$_3$) 3.06(s, 3H); 3.57(t, 2H); 3.89(t, 2H); 6.52(dd, 1H); 8.48(d, 1H); 8.54 (d, 1H) MS-ESI: 153 [MH]$^+$

Example 84

2M Aqueous sodium hydroxide solution (560 μl, 1.1 mmol) was added to a solution of 4-(2-fluoro-5-methoxycarbonyloxy-4-methylanilino)-7-((4-pyridyl)carboxamido)quinazoline (250 mg, 0.56 mmol) in methanol (7 ml) cooled at 0° C. and the mixture then stirred for 1 hour at ambient temperature. The mixture was diluted with water and the mixture adjusted to pH6 with 2M hydrochloric acid. The resulting solid was collected by filtration, washed with water and dried under vacuum. The solid was dissolved in methylene chloride/methanol and isopropanolic hydrogen chloride (0.7 ml of a 5M solution) was added. The volatiles were removed by evaporation, the solid residue was triturated with ether, collected by filtration, washed with ether and dried under vacuum to give 4-(2-fluoro-5-hydroxy4-methylanilino)-7-((4-pyridyl)carboxamido)quinazoline hydrochloride (241 mg, 93%). MS-ESI: 390[MH]$^+$ $^1$H NMR Spectrum: (DMSOd$_6$; CFCOOD) 2.2(s, 3H); 6.94(d, 1H); 7.13(d, 1H); 8.18(d, 1H); 8.53(d, 2H); 8.68(s, 1H); 8.77(d, 1H); 8.94(s, 1H); 9.20(d, 2H) Elemental analysis: Found C 52.0 H 4.3 N 14.3 C$_{21}$H$_{16}$N$_5$O$_2$F 1.2H$_2$O 1.95HCl Requires C 52.3 H 4.3 N 14.5%

The starting material was prepared as follows:

A mixture of 7-nitro-3,4-dihydroquinazolin-4-one (J. Chem. Soc. 1950, 1104–1111) (5 g, 26 mmol) in thionyl chloride (50 ml) and DMF (1 ml) was heated at reflux for 1.5 hours. Excess thionyl chloride was removed by evaporation and the residue azeotroped with toluene. The residue was suspended in ether, collected by filtration and dried under vacuum to give 4-chloro-7-nitroquinazoline hydrochloride (6.4 g, 100%).

$^1$H NMR Spectrum: (DMSOd$_6$) 8.26(dd, 1H); 8.36(d, 1H); 8.40(s, 1H); 8.42(dd, 1H) MS ESI: 209 [MH]$^+$ A solution of 4-chloro-7-nitroquinazoline hydrochloride (2.46 g, 10 mmol) and 2-fluoro-5-methoxycarbonyloxy-4-methylaniline (2.2 g, 11 mmol), prepared as described for the starting material in Example 12), in isopropanol (25 ml) was heated at 50° C. for 1 hour. The mixture was allowed to cool, the precipitated solid was collected by filtration recrystallised from methylene chloride/methanol/isopropanol to give 4-(2-fluoro-5-methoxycarbonyloxy-4-methylanilino)-7-nitroquinazoline hydrochloride (1.8 g, 45%) as a yellow solid.

$^1$H NMR Spectrum: (DMSOd$_6$) 2.21(s, 3H); 3.86(s, 3H); 7.40(d, 1H); 7.46(d, 1H); 8.49(dd, 1H); 8.63(s, 1H); 8.84(s, 1H); 8.89(d, 1H) MS-ESI: 373 [MH]$^+$ Elemental analysis: Found C 50.0 H 3.6 N 13.8 C$_{17}$H$_{13}$N$_4$O$_5$F 1HCl Requires C 50.0 H 3.5 N 13.7%

A mixture of 4-(2-fluoro-5-methoxycarbonyloxy-4-methylanilino)-7-nitroquinazoline hydrochloride (5.3 g, 13 mmol) and 10% palladium-on-charcoal catalyst (1 g) in ethanol (100 ml), ethanolic hydrogen chloride (1.8 ml of a 7M solution) and methanol (20 ml) was stirred under hydrogen at 1.7 atmospheres pressure for 75 minutes. The catalyst was removed by filtration through diatomaceous earth and the filter pad thoroughly washed with methylene chloride, methanol and ether and the solvent was removed from the filtrate by evaporation to give 7-amino-4-(2-fluoro-5-methoxycarbonyloxy4-methylanilino)quinazoline hydrochloride (4.8 g, 97%) as a yellow solid.

$^1$H NMR Spectrum: (DMSOd$_6$) 2.22(s, 3H); 3.87(s, 3H); 6.77(s, 1H); 7.08(dd, 1H); 7.15(m, 2H); 7.41(m, 2H); 8.35 (d, 1H); 8.63(s, 1H); 11.03(s, 1H) MS-ESI: 343 [MH]$^+$ A solution of 7-amino-4-(2-fluoro-5-methoxycarbonyloxy-4-methylanilino)quinazoline hydrochloride (0.45 g, 1.2 mmol) and isonicotinoyl chloride hydrochloride (296 mg, 1.66 mmol) in pyridine (15 ml) was stirred for 2 hours at ambient temperature, followed by 1 hour at 40° C. Further isonicotinoyl chloride hydrochloride (84 mg, 0.46 mmol) was added and the mixture was stirred at 40° C. for 2 hours. The volatiles were removed by evaporation, the mixture was diluted with water. The aqueous mixture was adjusted to pH7 and extracted with ethyl acetate. The combined extracts were washed with brine, dried (MgSO$_4$) and the solvent removed by evaporation. The residue was purified by flash chromatography eluting with methylene chloride/methanol (95/5 followed by 92/8). The purified solid was triturated with ether, collected by filtration, washed with ether and dried under vacuum to give 4-(2-fluoro-5-methoxycarbonyloxy4-methylanilino)-7-((4-pyridyl)carboxamido)quinazoline (264 mg, 49%).

$^1$H NMR Spectrum: (DMSOd$_6$) 2.19(s, 3H); 3.86(s, 3H); 7.31(d, 1H); 7.45(d, 1H); 7.92(d, 2H); 7.98(d, 1H); 8.31(s, 1H); 8.43(d, 1H); 8.47(s, 1H); 8.83(d, 2H); 9.78(br s, 1H); 10.89(br s, 1H)

Example 85

4-Chloro-2-fluoroaniline (77 mg, 0.53 mmol) was added to a solution of 4-chloro-6-methoxy-7-(2-(N-methyl-N-(6-methylpyrimidin-4-yl)amino)ethoxy)quinazoline hydrochloride (140 mg, 0.35 mmol) in isopropanol (5 ml) and the mixture heated at reflux for 1 hour. The solvent was removed by evaporation and the residue was partitioned between ethyl acetate and saturated aqueous sodium hydrogen carbonate solution. The organic layer was separated, washed with brine, dried (MgSO$_4$) and the solvent removed by evaporation. The residue was purified by flash chromatography eluting with methylene chloride/methanol (95/5). The purified solid was dissolved in methylene chloride/methanol and ethereal hydrogen chloride (1 ml of a 5M solution) was added. The volatiles were removed by evaporation, the residue was triturated with ether, collected by filtration, washed with ether and dried under vacuum to give 4-(4-chloro-2-fluoroanilino)-6-methoxy-7-(2-(N-methyl-N-(6-methylpyrimidin-4-yl)amino)ethoxy)quinazoline hydrochloride (75 mg, 39%).

$^1$H NMR Spectrum: (DMSOd$_6$; CF$_3$COOD) 2.46 and 2.47(2s, 3H); 3.35 and 3.42(2s, 3H); 3.97 and 3.98 (2s, 3H); 4.2(br s, 1H); 4.3(br s, 1H); 4.5(br s, 2H); 7.05 and 7.3(2s, 1H); 7.4 and 7.5(m, 2H); 7.62(t, 1H); 7.7(d, 1H); 8.25(br s, 1H); 8.8 and 8.9(2s, 2H) MS-ESI: 469 [MH]$^+$ The starting material was prepared as follows:

Sodium hydride (1.44 g of a 60% suspension in mineral oil, 36 mmol) was added in portions over 20 minutes to a solution of 7-benzyloxy-3,4-dihydroquinazolin-4-one (8.46 g, 30 mmol), (prepared as described for the starting material in Example 70), in DMF (70 ml) and the mixture stirred for 1.5 hours. Chloromethyl pivalate (5.65 g, 37.5 mmol) was added dropwise and the mixture stirred 2 hours at ambient temperature. The mixture was diluted with ethyl acetate (100 ml) and poured onto ice/water (400 ml) and 2M hydrochloric acid (4 ml). The organic layer was separated and the aqueous layer extracted with ethyl acetate, the combined extracts were washed with brine, dried (MgSO$_4$) and the solvent removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

$^1$H NMR Spectrum: (DMSOd$_6$) 1.1 l(s, 9H); 3.89(s, 3H); 5.3(s, 2H); 5.9(s, 2H); 7.27(s, 1H); 7.35(m, 1H); 7.47(t, 2H); 7.49(d, 2H); 7.51(s, 1H); 8.34(s, 1H)

A mixture of 7-benzyloxy-6-methoxy-3-((pivaloyloxy) methyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

$^1$H NMR Spectrum: (DMSOd$_6$) 1.11(s, 9H); 3.89(s, 3H); 5.89(s, 2H); 7.0(s, 1H); 7.48(s, 1H); 8.5(s, 1H)

Diethyl azodicarboxylate (679 mg, 3.9 mmol) was added dropwise to a suspension of 7-hydroxy-6-methoxy-3-((pivaloyloxy)methyl)-3,4-dihydroquinazolin4-one (918 mg, 3 mmol), triphenylphosphine (1 g, 3.9 mmol) and 2-(N-methyl-N-(t-butylcarbonyl)amino)ethanol (682 mg, 3.9 mmol), prepared as described below, in methylene chloride (20 ml) and the mixture stirred for 1 hour at ambient temperature. Further 2-(N-methyl-N-(t-butylcarbonyl) amino)ethanol (105 mg, 0.6 mmol), triphenylphosphine (786 mg, 3 mmol) and diethyl azodicarboxylate (522 mg, 3 mmol) were added and the mixture stirred for 30 minutes at ambient temperature. The mixture was concentrated to half volume by evaporation and purified by column chromatography eluting with methylene chloride/ether (7/3 increasing to 1/1) to give 6-methoxy-7-(2-(N-methyl-N-(t-butylcarbonyl)amino)ethoxy)-3-((pivaloyloxy)methyl)-3,4-dihydroquinazolin-4-one (1.3 g, 98%).

$^1$H NMR Spectrum: (CDCl$_3$) 1.2(s, 9H); 1.45(s, 9H); 3.05(br s, 3H); 3.72(br s, 2H); 3.98(s, 3H); 4.25(br s, 2H); 5.95(s, 2H); 7.1(br s, 1H); 7.6(s, 1H); 8.2(s, 1H)

A solution of 6-methoxy-7-(2-(N-methyl-N-(t-butylcarbonyl)amino)ethoxy)-3-((pivaloyloxy)methyl)-3,4-dihydroquinazolin-4-one (1.39 g, 3 mmol) in methylene chloride (4 ml) and TFA (4 ml) was stirred at ambient temperature for 1 hour. Toluene was added, and the volatiles were removed by evaporation. The residue was triturated with ether and the resulting solid was collected by filtration. The solid was dissolved in water, sodium hydrogen carbonate was added and the aqueous mixture was extracted with methylene chloride. The organic extract was dried (MgSO$_4$) and the solvent removed by evaporation. The residue was triturated with ether and the solid was collected by filtration to give 6-methoxy-7-(2-(methylamino)ethoxy)-3-((pivaloyloxy)methyl)-3,4-dihydroquinazolin-4-one (800 mg, 73%).

$^1$H NMR Spectrum: (DMSOd$_6$; CF$_3$COOD) 1.13(s, 9H); 2.72(s, 3H); 3.45(br s, 2H); 3.95(s, 3H); 4.5(t, 2H); 5.94(s, 2H); 7.31(s, 1H); 7.6(s, 1H); 8.47(s, 1H) MS-ESI: 364 [MH]$^+$ A solution of 6-methoxy-7-(2-(methylamino)ethoxy)-3-((pivaloyloxy)methyl)-3,4-dihydroquinazolin-4-one (363 mg, 1 mmol) and 4-chloro-6-methylpyrimidine (257 mg, 2 mmol), (J. Het. Chem., 1969, 6, 879), in N,N-diisopropylethylamine (2 ml) was heated at reflux for 30 minutes. The volatiles were removed by evaporation and the residue was partitioned between ethyl acetate and water. The organic layer was separated, washed with brine, dried (MgSO$_4$) and the solvent removed by evaporation. The residue was purified by column chromatography eluting with methylene chloride/methanol (95/5) to give 6-methoxy-7-(2-(N-methyl-N-(6-methylpyrimidin-4-yl) amino)ethoxy)-3-((pivaloyloxy)methyl)-3,4-dihydroquinazolin-4-one (365 mg, 80%).

$^1$H NMR Spectrum: (CDCl$_3$) 1.19(s, 9H); 2.36(s, 3H); 3.18(s, 3H); 3.95(s, 3H); 4.09(t, 2H); 4.34(t, 2H); 5.9(s, 2H); 6.3(s, 1H); 7.14(s, 1H); 7.63(s, 1H); 8.17(s, 1H); 8.5(s, 1H) MS-ESI: 456 [MH]$^+$ A solution of 6-methoxy-7-(2-(N-methyl-N-(6-methylpyrimidin-4-yl)amino)ethoxy)-3-((pivaloyloxy) methyl)-3,4-dihydroquinazolin-4-one (365 mg, 0.8 mmol) in methanolic ammonia (30 ml of a 3M solution) was stirred at ambient temperature for 16 hours. The volatiles were removed by evaporation, the residue was triturated with ether, the solid was collected by filtration, washed with ether and dried under vacuum to give 6-methoxy-7-(2-(N-methyl-N-(6-methylpyrimidin-4-yl)amino)ethoxy)-3,4-dihydroquinazolin-4-one (250 mg, 92%).

$^1$H NMR Spectrum: (DMSOd$_6$; CF$_3$COOD) 2.44(s, 3H); 3.32 and 3.39(2s, 3H); 3.86 and 3.87(2s, 3H); 4.12(t, 1H); 4.25(t, 1H); 4.42(m, 2H); 7.02 and 7.23(2s, 1H); 7.24(t, 1H); 7.50(s, 1H); 8.55 and 8.8(2 m, 1H); 8.78 and 8.80(2s, 1H) MS-ESI: 342 [MH]$^+$ A mixture of 6-methoxy-7-(2-(N-methyl-N-(6-methylpyrimidin-4-yl)amino)ethoxy)-3,4-dihydroquinazolin-4-one (250 mg, 0.73 mmol) in thionyl chloride (5 ml) and DMF (0.1 ml) was heated at reflux for 1 hour. The mixture was diluted with toluene and the volatiles were removed by evaporation. The residue was triturated with methylene chloride/ether, the solid was collected by filtration and dried under vacuum to give 4-chloro-6-methoxy-7-(2-(N-methyl-N-(6-methylpyrimidin-4-yl)amino)ethoxy)quinazoline hydrochloride (260 mg, 90%).

2-(N-methyl-N-(t-butylcarbonyl)amino)ethanol was prepared as follows:

A solution of di-t-butyldicarbonate (4.52 g, 20 mmol) in THF (10 ml) was added to a solution of 2-(N-methylamino) ethanol (1.5 g, 20 mmol) in a mixture of water (10 ml) and THF (10 ml). The mixture was stirred at ambient temperature for 18 hours, the THF was removed by evaporation and the aqueous residue was partitioned between ether and water. The organic layer was washed with water, brine, dried (MgSO$_4$) and evaporated to give 2-(N-methyl-N-(t-butylcarbonyl)amino)ethanol (3 g, 85%).

$^1$H NMR Spectrum (CDCl$_3$) 1.46(s, 9H); 2.92(s, 3H); 3.39 (t, 2H); 3.75(t, 2H). MS-ES: 176 [MH]$^+$

Example 86

Diethyl azodicarboxylate (295 µl, 1. 8 mmol) was added dropwise to a suspension of 4-(4-chloro-2-fluoroanilino)-7-hydroxy-6-methoxyquinazoline (200 mg, 0.62 mmol), (prepared as described for the starting material in Example 24), 2-(3,5-dimethyl-[1,2,4]-triazol-4-yl)ethanol (114 mg, 0.81mmol), (EP 0329357 A1), and triphenylphosphine (492 mg, 1.8 mmol) in methylene chloride (4 ml) and the mixture stirred for 1 hour at ambient temperature. The precipitated solid was collected by filtration, washed with ether and dried under vacuum. The solid was dissolved in methylene chloride/methanol and ethereal hydrogen chloride (2 ml of 4.5M solution) was added. The volatiles were removed by evaporation, the residue was suspended in ether, collected by filtration, washed with ether and dried under vacuum to give 4-(4-chloro-2-fluoroanilino)-7-(2-(3,5-dimethyl-[1,2,4]-triazol-4-yl)ethoxy)-6-methoxyquinazoline hydrochloride (184 mg, 54%).

$^1$H NMR Spectrum: (DMSOd$_6$; CF$_3$COOD) 2.78(s, 6H); 4.03(s, 3H); 4.57(t, 2H); 4.75(t, 2H); 7.37(s, 1H); 7.46(d, 1H); 7.64(t, 1H); 7.66(d, 1H); 8.31(s, 1H); 8.87(s, 1H) MS-ESI: 443 [MH]$^+$ Elemental Analysis: Found C 48.0 H 4.6 N 16.1 C$_{21}$H$_{20}$N$_6$O$_2$ClF 1H$_2$O 1.85HCl Requires C 47.7 H 4.6 N 15.9%

Example 87

Diethyl azodicarboxylate (295 µl, 1.8 mmol) was added dropwise to a solution of the 75/25 mixture of 2-(2,4-dimethylimidazol-1-yl)ethanol and 2-(2,5-dimethylimidazol-1-yl)ethanol (114 mg, 0.81 mmol), 4-(4-chloro-2-fluoroanilino)-7-hydroxy-6-methoxyquinazoline (200 mg, 0.62 mmol), (prepared as described for the starting material in Example 24), and triphenylphosphine (492 mg, 1.8 mmol) in methylene chloride (4 ml) and the mixture stirred for 4 hours at ambient temperature. Further triphenylphosphine (49 mg, 0.18 mmol), mixture of imidazolylethanols (26 mg, 0.18 mmol) and diethyl azodicarboxylate (29 µl, 0.18 mmol) were added and the mixture stirred for 1 hour. The precipitated solid was collected by filtration, washed with methylene chloride, and dried under vacuum. The solid was dissolved in methylene chloride/methanol and ethereal hydrogen chloride (1.5 ml of a 4.5M solution) was added. The volatiles were removed by evaporation, the solid residue was suspended in ether, collected by filtration, washed with ether and dried under vacuum to give a 75/25 mixture of 4-(4-chloro-2-fluoroanilino)-7-(2-(2,4-dimethylimidazol-1-yl)ethoxy)-6-methoxyquinazoline hydrochloride and 4-(4-chloro-2-fluoroanilino)-7-2-(2,5-dimethylimidazol-1-yl)ethoxy)-4-methoxyquinazoline hydrochloride (159 mg, 48%).

$^1$H NMR Spectrum: (DMSOd$_6$; CF$_3$COOD) 2.23 and 2.43(2s, 3H); 2.73 and 2.76(2s, 3H); 4.02(s, 3H); 4.6(br s, 2H); 4.6 and 4.75(m, 2H); 7.3–7.5(m, 3H); 7.61(t, 1H); 7.68(d, 1H); 8.24(s, 1H); 8.88(s, 1H) MS-ESI: 442 [MH]$^+$ Elemental analysis: Found C 49.9 H 4.6 N 13.3 C$_{22}$H$_{21}$N$_5$O$_2$ClF 1.1H$_2$O 1.85HCl Requires C 50.1 H 4.8 N 13.3%

The starting material was prepared as follows:

2,4-Dimethylimidazole (1.5 g, 15.6 mmol) was added in portions to a suspension of sodium hydride (936 mg of a 60% suspension in mineral oil, 23 mmol) in DMF (8 ml) and the mixture was stirred for 30 minutes at ambient temperature. 2-Bromoethanol (1.66 ml, 23 mmol) was added and the mixture stirred at 100° C. for 16 hours. The solvent was removed by evaporation and concentrated hydrochloric acid (1 ml) was added to the residue. The resulting solid was triturated with methylene chloride, collected by filtration and dried under vacuum. The solid was purified by column chromatography on neutral alumina eluting with methylene chloride/methanol (97/3) and then column chromatography eluting with methylene chloride/methanol (93/7 followed by 90/10) to give a 75/25 mixture of 2-(2,4-dimethylimidazol-1-yl)ethanol and 2-(2,5-dimethylimidazol-1-yl)ethanol (650 mg, 29%). MS-ESI: 140 [MH]$^+$

Example 88

Diethyl azodicarboxylate (236 µl, 1.5 mmol) was added dropwise to a suspension of 4-(4-chloro-2-fluoroanilino)-7-hydroxy-6-methoxyquinazoline (160 mg, 0.5 mmol), (prepared as described for the starting material in Example 24), triphenylphosphine (393 mg, 1.5 mmol) and 2-(3-pyridyl)ethanol (86 mg, 0.7 mmol), (J. Heterocycl. Chem. 1992, 29, 1663), in methylene chloride (6 ml) and the mixture stirred for 4 hours at ambient temperature. The mixture was poured directly on to a silica column and eluted with methylene chloride/acetonitrile/methanol (60/35/5). The purified solid was dissolved in methylene chloride/ methanol and ethereal hydrogen chloride (1.5 ml of a 4.5M solution) was added. The volatiles were removed by evaporation, the solid residue was suspended in ether, collected by filtration, washed with ether and dried under vacuum to give 4-(4-chloro-2-fluoroanilino)4-methoxy-7-(2-(3-pyridyl)ethoxy)quinazoline hydrochloride (154 mg, 52%).

$^1$H NMR Spectrum: (DMSOd$_6$; CF$_3$COOD) 3.45(t, 2H); 4.01(s, 3H); 4.56(t, 2H); 7.44(s, 1H); 7.46(d, 1H); 7.61(t, 1H); 7.67(d, 1H); 8.13(t, 1H); 8.19(s, 1H); 8.71(d, 1H); 8.88(s, 1H); 8.9(d, 1H); 9.01(s, 1H) MS-ESI: 425 [MH]+ Elemental analysis: Found C 52.7 H 4.3 $C_{22}H_{18}N_4O_2ClF$ 0.8H$_2$O 1.8HCl Requires C 52.3 H 4.3%

Example 89

Diethyl azodicarboxylate (236 μl, 1.5 mmol) was added dropwise to a suspension of 4-(4-chloro-2-fluoroanilino)-7-hydroxy-6-methoxyquinazoline (160 mg, 0.5 mmol), (prepared as described for the starting material in Example 24), triphenylphosphine (393 mg, 115 mmol) and 2-(6-methyl-2-pyridyl)ethanol (96 mg, 0.7 mmol), (J. Chem. Soc. A, 1971, 388), in methylene chloride (6 ml) and the mixture stirred for 16 hours at ambient temperature. The mixture was poured directly on to a silica column and eluted with methylene chloride/methanol (95/5). The purified solid was dissolved in methylene chloride/methanol and ethereal hydrogen chloride (1.5 ml of a 4.5M solution) was added. The mixture was diluted with ether and the resulting precipitate was collected by filtration, washed with ether and dried under vacuum to give 4-(4-chloro-2-fluoroanilino)-6-methoxy-7-(2-(6-methyl-2-pyridyl)ethoxy)quinazoline hydrochloride (97 mg, 34%).

$^1$H NMR Spectrum: (DMSOd$_6$; CF$_3$COOD) 2.78(s, 3H); 3.64(t, 2H); 3.98(s, 3H); 4.67(t, 2H); 7.46(s, 1H); 7.48(br s, 1H); 7.62(t, 1H); 7.68(dd, 1H); 7.85(d, 1H); 7.94(d, 1H); 8.19(s, 1H); 8.48(t, 1H); 8.88(s, 1H) MS-ESI: 439 [MH]+ Elemental Analysis: Found C 52.7 H 4.5 N 10.7 $C_{23}H_{20}N_4O_2ClF$ 1H$_2$O 1.8HCl Requires C 52.9 H 4.6 N 10.7%

Example 90

A mixture of 4-chloro-7-(2-(imidazol-1-yl)ethoxy)-6-methoxyquinazoline (49 mg, 0.16 mmol) and 3-hydroxyaniline (21 mg, 0.19 mmol) in isopropanol (3 ml) and isopropanolic hydrogen chloride (0.2 ml of a 5M solution) was stirred at 80° C. for 1 hour. The precipitated solid was collected by filtration, washed with isopropanol and ether and dried under vacuum to give 4-(3-hydroxyanilino)-7-(2-(imidazol-1-yl)ethoxy)-6-methoxyquinazoline hydrochloride (56 mg, 93%).

$^1$H NMR Spectrum: (DMSOd$_6$; CF$_3$COOD) 4.01(s, 3H); 4.64(t, 2H); 4.78(t, 2H); 6.71(d, 1H); 7.1(m, 2H); 7.28(t, 1H); 7.41(s, 1H); 7.74(s, 1H); 7.83(s, 1H); 8.21(s, 1H); 8.87(s, 1H); 9.22(s, 1H) MS-ESI: 378 [MH]+ Elemental Analysis: Found C 52.7 H 4.9 N 15.1 $C_{20}H_{19}N_5O_3$ 0.6H$_2$O 1.85HCl Requires C 52.7 H 4.9 N 15.4%

The starting material was prepared as follows:

Diethyl azodicarboxylate (435 mg, 2.5 mmol) was added dropwise to a suspension of 7-hydroxy-6-methoxy-3-((pivaloyloxy)methyl)-3,4-dihydroquinazolin-4-one (612 mg, 2 mmol), (prepared as described for the starting material in Example 85), 2-(imidazol-1-yl)ethanol (280 mg, 2.5 mmol), (J. Med. Chem. 1993, 25 4052–4060), and triphenylphosphine (655 mg, 2.5 mmol) in methylene chloride (10 ml) at 5° C. The mixture was stirred for 10 minutes at 5° C. and then 1 hour at ambient temperature. The mixture was poured directly on to a silica column and eluted with methylene chloride/methanol (95/5) to give 7-(2-(imidazol-1-yl)ethoxy)-6-methoxy-3-((pivaloyloxy)methyl)-3,4-dihydroquinazolin-4-one (640 mg, 80%).

$^1$H NMR Spectrum: (CDCl$_3$) 1.19(s, 9H); 3.98(s, 3H); 4.34(m, 2H); 4.45(m, 2H); 5.94(s, 2H); 7.02(s, 1H); 7.07(s, 1H); 7.11(s, 1H); 7.64(s, 1H); 7.67(s, 1H); 8.17(s, 1H) MS-ESI: 423 [MNa]+ Elemental Analysis: Found C 58.3 H 6.4 N 13.9 $C_{20}H_{24}N_4O_5$ 0.7H$_2$O Requires C 58.2 H 6.2 N 13.6%

A solution of 7-(2-(imidazol-1-yl)ethoxy)-6-methoxy-3-((pivaloyloxy)methyl)-3,4-dihydroquinazolin-4-one (640 mg, 1.6 mmol) in saturated methanolic ammonia (10 ml) was stirred for 15 hours at ambient temperature. The volatiles were removed by evaporation, the solid was triturated with ether, collected by filtration and dried under vacuum to give 7-(2-(imidazol-1-yl)ethoxy)-6-methoxy-3,4-dihydroquinazolin4-one (412 mg, 90%).

$^1$H NMR Spectrum: (DMSOd$_6$) 3.89(s, 3H); 4.4–4.5(m, 4H); 6.9(s, 1H); 7.16(s, 1H); 7.28(s, 1H); 7.47(s, 1H); 7.7(s, 1H); 7.99(s, 1H) MS-ESI: 287 [MH]+ Elemental Analysis: Found C 57.8 H 5.2 N 19.3 $C_{14}H_{14}N_4O_3$ 0.3H$_2$O Requires C 57.7 H 5.1 N 19.2%

A mixture of 7-(2-(imidazol-1-yl)ethoxy)-6-methoxy-3,4-dihydroquinazolin-4-one (412 mg, 1.44 mmol), thionyl chloride (5 ml) and DMF (0.2 ml) was heated at reflux for 1 hour. The mixture was diluted with toluene and the volatiles were removed by evaporation. The residue was suspended in methylene chloride, cooled to 0° C. and aqueous sodium hydrogen carbonate solution was added. The resulting precipitate was collected by filtration and dried under vacuum to give 4-chloro-7-(2-(imidazol-1-yl)ethoxy)-6-methoxyquinazoline (258 mg, 59%).

$^1$H NMR Spectrum: (DMSOd$_6$) 4.01(s, 3H); 4.47(m, 2H); 4.53(m, 2H); 6.89(s, 1H); 7.27(s, 1H); 7.41(s, 1H); 7.49(s, 1H); 7.70(s, 1H); 8.88(s, 1H) MS-ESI: 327 [MNa]+

Example 91

Diethyl azodicarboxylate (220 μl, 1.4 mmol) was added dropwise to a solution of 4-(4-chloro-2-fluoroanilino)-7-hydroxy-6-methoxyquinazoline (150 mg, 0.47 mmol), (prepared as described for the starting material in Example 24), 2-(1,2,4-triazol-4-yl)ethanol (64 mg, 0.56 mmol) and triphenylphosphine (369 mg, 1.4 mmol) in methylene chloride (5 ml) and the mixture stirred for 30 minutes at ambient temperature. Further 2-(1,2,4-triazol-4-yl)ethanol (16 mg, 0.14 mmol), triphenylphosphine (37 mg, 0.14 mmol) and diethyl azodicarboxylate (22 μl, 0.14 mmol) was added and the mixture stirred for 1 hour at ambient temperature. The precipitated solid was collected by filtration, washed with methylene chloride and methanol and dried under vacuum. The solid was dissolved in methylene chloride/methanol and ethereal hydrogen chloride (1.5 ml of a 2.2M solution) was added. The volatiles were removed by evaporation, the solid residue was suspended in ether, collected by filtration, washed with ether and dried under vacuum to give 4-(4-chloro-2-fluoroanilino)-6-methoxy-7-(2-(1,2,4-triazol-4-yl)ethoxy)quinazoline hydrochloride (93 mg, 40%).

$^1$H NMR Spectrum: (DMSOd$_6$; CF$_3$COOD) 4.02(s, 3H); 4.66(t, 2H); 4.85(t, 2H); 7.41(s, 1H); 7.46(dd, 1H); 7.62(t, 1H); 7.69(dd, 1H); 8.11(s, 1H); 8.89(s, 1H); 9.55 (s, 2H) MS-ESI: 415 [MH]+ Elemental analysis: Found C 45.9 H 3.7 N 17.1 $C_{19}H_{16}N_6O_2ClF$ 0.5H$_2$O 2HCl Requires C 45.9 H 3.9 N 16.9%

The starting material was prepared as follows:

A solution of N,N-dimethylformamide azine (1 g, 7 mmol), (J. Chem. Soc. C, 1967, 1664), p-toluene sulphonic acid (45 mg) and ethanolamine (4.3 g, 70 mmol) in benzene (15 ml) was heated at reflux for 8 hours. The mixture was allowed to cool, the solvent was removed by evaporation and the residue was purified by column chromatography eluting with methylene chloride/methanol (90/10 followed by 85/15) to give 2-(1,2,4-triazol-4-yl)ethanol (328 mg, 41%).

$^1$H NMR Spectrum: (CDCl$_3$) 3.97(t, 2H); 4.11(t, 2H); 4.9(br s, 1H); 8.06(s, 2H) MS-ESI: 113 [MH]+

Example 92

1,1'-(azodicarbonyl)dipiperidine (480 mg, 1.9 mmol) was added in portions to a mixture of 4-(4-chloro-2-fluoroanilino)-7-hydroxy-6-methoxyquinazoline (200 mg, 0.63 mmol), 3-benzyloxypropanol (150 μl, 0.95 mmol) and tributylphosphine (459 μl, 1.86 mmol) in methylene chloride (20 ml) at 5° C. The reaction was stirred for 1 hour at 5° C. and then for 18 hours at ambient temperature. The mixture was diluted with ether and stirred for 15 minutes. The insolubles were removed by filtration and the volatiles were removed from the filtrate by evaporation. The residue was partitioned between ethyl acetate and water, and the organic layer was separated, dried ($MgSO_4$) and the solvent removed by evaporation. A 1M solution of ethereal hydrogen chloride was added to the residue, the resulting solution was reduced in volume by evaporation and the resulting precipitate was collected by filtration and dried to give 7-(3-benzyloxypropoxy)-4-(4-chloro-2-fluoroanilino)-6-methoxyquinazoline hydrochloride (90 mg, 31%).

$^1$H NMR Spectrum ($CDCl_3$) 2.12(t, 2H); 3.62(t, 2H); 4.00(t, 3H); 4.28(t, 2H); 4.45(s, 2H); 7.21–7.38(m, 6H); 7.42(d 1H); 7.60(t, 1H); 7.64(dd, 1H); 8.22(s, 1H); 8.80(s, 1H) MS-ESI: 468 $[MH]^+$

Example 93

1,1'-(azodicarbonyl)dipiperidine (840 mg, 3 mmol) was added in portions to a mixture of 4-(4-chloro-2-fluoroanilino)-7-hydroxy-6-methoxyquinazoline (315 mg, 1 mmol), ethyl 4-hydroxymethyl-2-pyridinecarboxylate (250 mg, 1.4 mmol), (J. Het. Chem. 1993, 30, 631–635) and tributylphosphine (800 μl, 3 mmol) in methylene chloride (50 ml) at 0° C. The mixture was allowed to warm to ambient temperature over 2 hours, the insolubles were removed by filtration and the filtrate was washed with water and brine, dried ($Na_2SO_4$) and the solvent removed by evaporation. The residue was purified by column chromatography eluting with methylene chloride/methanol (10:0 increasing to 9:1). The purified product was recrystallised from methylene chloride/hexane to give 4-(4-chloro-2-fluoroanilino)-7-(2-ethoxycarbonylpyrid-4-yl)methoxy-6-methoxyquinazoline (285 mg, 60%). m.p. 212–214° C.

$^1$H NMR Spectrum ($DMSOd_6$) 1.30(t, 3H); 3.96(s, 3H); 4.35(q, 2H); 5.45(s, 2H); 7.14(s, 1H); 7.35(dd, 1H); 7.5–7.6 (m, 2H); 7.85(s, 1H); 8.15(s, 1H); 8.35(s, 1H); 8.75(d, 1H); 9.55(s, 1H) Elemental analysis: Found C 58.9 H 4.4 N 12.0 $C_{24}H_{20}ClFN_4O_4$ 0.5 $H_2O$ Requires C 58.7 H 4.4 N 11.5%

Example 94

1,1'-(azodicarbonyl)dipiperidine (1.68 g, 6 mmol) was added in portions to a mixture of 4-(4-chloro-2-fluoroanilino)-7-hydroxy-6-methoxyquinazoline (640 mg, 2 mmol), 4-hydroxymethyl-2-(methylamino)pyridine (385 mg, 2.8 mmol) and tributylphosphine (1.6 ml, 6 mmol) in methylene chloride (50 ml) at 0° C. The mixture was allowed to warm to ambient temperature over 2 hours, the insolubles were removed by filtration and the filtrate was washed with water and brine, dried ($Na_2SO_4$) and the solvent removed by evaporation. The residue was purified by column chromatography eluting with methylene chloride/methanol (10:0 increasing to 9:1). The purified product was dissolved in acetone/methanol and a 1M solution of ethereal hydrogen chloride was added. The resulting precipitate was collected by filtration and dried to give 4-(4-chloro-2-fluoroanilino)-7-(2-(methylamino)pyrid-4-yl) methoxy-6-methoxyquinazoline hydrochloride (395 mg, 45%).

$^1$H NMR Spectrum ($DMSOd_6$) 2.95(d, 3H); 4.05(s, 3H); 5.42(s, 2H); 6.90(d, 1H); 7.15(s, 1H); 7.40(d, 1H); 7.44(s, 1H); 7.58(t, 1H); 7.62(dd, 1H); 7.95(d, 1H); 8.46(s, 1H); 8.75(s, 1H); 9.06(br s, 1H); 11.83(br s, 1H) MS-ESI: 440 $[MH]^+$ The starting material was prepared as follows:

A mixture of 2-chloro-4-hydroxymethylpyridine (1.0 g, 7 mmol), (prepared as described for the starting material in Example 58), and methylamine (30 ml of a 30% solution in ethanol) was heated in a Carius tube for 16 hours at 200° C. The mixture was allowed to cool and the mixture partitioned between saturated aqueous sodium hydrogen carbonate solution and ethyl acetate. The organic layer was separated, dried ($MgSO_4$) and the volatiles removed by evaporation. The residue was purified by column chromatography eluting with ethyl acetate to give 4-hydroxymethyl-2-(methylamino)pyridine (440 mg, 46%) as a yellow oil.

$^1$H NMR Spectrum ($DMSOd_6$) 2.72(d, 3H); 4.35(d, 2H); 5.15(t, 1H); 6.30(br d, 1H); 6.35(d, 1H); 6.38(s, 1H); 7.85(d, 1H)

Example 95

1,1'-(azodicarbonyl)dipiperidine (1.68 g, 6 mmol) was added in portions to a mixture of 4-(4-chloro-2-fluoroanilino)-7-hydroxy-6-methoxyquinazoline (640 mg, 2 mmol), 4-hydroxymethyl-2-(dimethylamino)pyridine (426 mg, 2.8 mmol) and tributylphosphine (1.6 ml, 6 mmol) in methylene chloride (50 ml) at 0° C. The mixture was allowed to warm to ambient temperature over 2 hours, the insolubles were removed by filtration and the filtrate was washed with water and brine, dried ($Na_2SO_4$) and the solvent removed by evaporation. The residue was purified by column chromatography eluting with methylene chloride/methanol (100:0 increasing to 95:5). The purified product was dissolved in acetone/methanol and a 1M solution of ethereal hydrogen chloride was added. The resulting precipitate was collected by filtration and dried to give 4-(4-chloro-2-fluoroanilino)-7-(2-(dimethylamino)pyrid4-yl)methoxy-6-methoxyquinazoline hydrochloride (305 mg, 30%). m.p. 290° C.

$^1$H NMR Spectrum ($DMSOd_6$) 3.05(s, 6H); 4.05(s, 3H); 5.45(s, 2H); 6.95(d, 1H); 7.35(s, 1H); 7.42(dd, 1H); 7.56(t, 2H); 7.62(dd, 1H); 8.00(d, 1H); 8.55(s, 1H); 9.80(s, 1H); 11.95(br s, 1H) MS-ESI: 454 $[MH]^+$ Elemental analysis: Found C 47.2 H 4.9 N 12.1 $C_{23}H_{21}ClFN_5O_2$ 3 HCl $H_2O$ Requires C 47.6 H 4.5 N 12.1%

The starting material was prepared as follows:

A mixture of 2-chloro-4-hydroxymethylpyridine (1.0 g, 7 mmol), (prepared as described for the starting material in Example 58), and dimethylamine (30 ml of a 30% solution in ethanol) was heated in a Carius tube for 16 hours at 200° C. The mixture was allowed to cool and the mixture partitioned between saturated aqueous sodium bicarbonate solution and ethyl acetate. The organic layer was separated, dried ($MgSO_4$) and the volatiles removed by evaporation. The residue was purified by column chromatography eluting with ethyl acetate to give 4-hydroxymethyl-2-(dimethylamino)pyridine (1 g, 94%) as a yellow oil.

$^1$H NMR Spectrum ($DMSOd_6$) 3.00(s, 6H); 4.40(d, 2H); 5.20(t, 1H); 6.45(d, 1H); 6.55(s, 1H); 7.96(d, 1H) MS-ESI: 153 $[MH]^+$

Example 96

A mixture of 4-(3-hydroxyprop-2-en-1-yl)pyridine (180 mg, 1.3 mmol) and thionyl chloride (0.3 ml) in toluene (10 ml) was stirred at room temperature for 2 hours. The volatiles were removed by evaporation to give crude 4-(3-chloroprop-2-en-1-yl)pyridine hydrochloride (180 mg, 0.94 mmol)) This product was added to a mixture of 4-(4-chloro-2-fluoroanilino)-7-hydroxy-6-methoxyquinazoline (500 mg, 1.6 mmol) and potassium carbonate (500 mg, 4.9 mmol) in DMF (20 ml) and the mixture stirred at 100° C. for 1 hour. The reaction mixture was allowed to cool and partitioned between ethyl acetate and water. The organic layer was separated, washed with water and brine, dried (MgSO$_4$) and the solvent removed by evaporation. The residue was purified by column chromatography eluting with methylene chloride/methanol (100/0 increasing to 95/5) and then by reverse phase (C18) HPLC eluting with methanol/water (30/70 increasing to 50/50) to give 4-(4-chloro-2-fluoroanilino)-6-methoxy-7-(3-(pyrid-4-yl)prop-2-en-1-yloxy)quinazoline (15 mg, 4%).

$^1$H NMR Spectrum (DMSOd$_6$) 4.00(s, 3H); 5.05(d, 2H); 6.93(d, 1H); 7.11 (dt, 1H); 7.40(s, 1H); 7.40–7.43(m, 2H); 7.60(t, 1H); 7.65(d, 1H); 7.80(m, 2H); 8.05(s, 1H); 8.70(br s, 2H) MS-ESI: 437 [MH]$^+$ The starting material was prepared as follows n-Butyllithium (25 ml of a 1.6M solution in hexane, 40 mmol) was added dropwise to a stirred suspension of 2-hydroxyethyltriphenylphosphonium bromide (7.74 g, 20 mmol) in THF (50 ml) at −70° C. and the mixture allowed to warm to −30° C. and stirred for 2 hours. 4-Pyridinecarboxaldehyde (2.16 g, 20 mmol) was added to the resulting red solution and the mixture stirred for 1 hour at −30° C. and then cooled to −70° C. n-Butyllithium (12.5 ml of a 1.6M solution in hexane, 20 mmol) was added and the reaction mixture stirred at −70° C. for 1 hour. The mixture was quenched with isopropanol and allowed to warm to ambient temperature. Saturated aqueous ammonium chloride solution was added, the organic layer separated and the aqueous layer extracted with ethyl acetate (3×50 ml). The combined extracts were washed with brine and dried (MgSO4) and the volatiles removed by evaporation. The residue was purified by column chromatography eluting with ethyl acetate to give 4-(3-hydroxyprop-2-en-1-yl)pyridine MS-ESI: 136 [MH]$^+$

Example 97

A suspension of 4-chloro-7-(2-(1,2,4-triazol-1-yl)ethoxy)-6-methoxyquinazoline (214 mg, 0.7 mmol), 4-bromo-2-fluoroaniline (160 mg, 0.84 mmol) in isopropanolic hydrogen chloride (1 ml of a 5M solution) and isopropanol (5 ml) was heated at 80 ° C. for 1 hour. The mixture was allowed to cool, the precipitate was collected by filtration, washed with isopropanol and then ether and dried under vacuum at 70° C. to give 4-(4-bromo-2-fluoroanilino)-7-(2-(1,2,4-triazol-1-yl)ethoxy)-6-methoxyquinazoline hydrochloride (55 mg, 15%).

$^1$H NMR Spectrum (DMSOd$_6$) 3.99(s, 3H); 4.62(t, 2H); 4.75(t, 2H); 7.37(s, 1H); 7.5–7.7(m, 2H); 7.81(d, 1H); 8.04(s, 1H); 8.24(s, 1H); 8.63(s, 1H); 8.84(s, 1H); 11.52(s, 1H) MS-ESI: 459 [MH]$^+$ Elemental analysis Found C 41.8 H 3.4 N 15.6 C$_{19}$H$_{16}$BrFN$_6$O$_2$ 0.8 H$_2$O 1.9 HCl Requires C 42.0 H 3.6 N 15.5%

The starting material was prepared as follows:

Diethyl azodicarboxylate (1.1 ml, 7 mmol) was added dropwise to a solution of 7-hydroxy-6-methoxy-3-((pivaloyloxy)methyl)-3,4-dihydroquinazolin-4-one (1.7 g, 5.55 mmol), 2-(1,2,4-triazol-1-yl)ethanol (791 mg, 7 mmol), (Ann. Pharm. Fr. 1977, 35, 503–508) and triphenylphosphine (1.8 g, 7 mmol) cooled at 5° C. The mixture was allowed to warm to ambient temperature and stirred for 1 hour. The mixture was poured directly on to a column of silica and eluted with methylene chloride/methanol (95/5) to give 6-methoxy-3-((pivaloyloxy)methyl)-7-(2-(1,2,4-triazol-1-yl)ethoxy)-3,4-dihydroquinazolin-4-one (1.64 g, 74%).

$^1$H NMR Spectrum (DMSOd$_6$, CF$_3$COOD) 1.12(s, 9H); 3.87(s, 3H); 4.57(t, 2H); 4.74(t, 2H); 5.92(s, 2H); 7.24(s, 1H); 7.51(s, 1H); 8.36(d, 1H); 8.41(s, 1H); 9.02(d, 1H) MS-ESI: 424 [MNa]$^+$ Elemental analysis Found C 56.5 H 6.0 N 17.6 C$_{19}$H$_{23}$N$_5$O$_5$ Requires C56.9 H 5.8 N 17.%

A solution of 6-methoxy-3-((pivaloyloxy)methyl)-7-(2-(1,2,4-triazol-1-yl)ethoxy)-3,4-dihydroquinazolin-4-one (1.6 g, 4 mmol) in saturated methanolic ammonia (25 ml) was stirred at ambient temperature for 2 days. The volatiles were removed by evaporation, the solid residue was triturated with ether, collected by filtration and dried under vacuum to give 6-methoxy-7-(2-(1,2,4-triazol-1-yl)ethoxy)-3,4-dihydroquinazolin-4-one (1.11 g, 98%)

$^1$H NMR Spectrum (DMSO d$_6$) 3.84(s, 3H); 4.51(t, 2H); 4.65(t, 2H); 7.16(s, 1H); 7.44(s, 1H); 7.89(s, 1H); 7.99(s, 1H); 8.55(s, 1H) MS-EI: 287 [M]$^+$ Elemental analysis Found C 53.9 H 4.6 N 24.6 C$_{13}$H$_{13}$N$_5$O$_3$ Requires C 54.4 H 4.6 N 24.4

A solution of 6-methoxy-7-(2-(1,2,4-triazol-1-yl)ethoxy)-3,4-dihydroquinazolin-4-one (1.11 g, 3.86 mmol) and DMF (0.6 ml) in thionyl chloride (15 ml) was heated at reflux for 1 hour. The mixture was allowed to cool, toluene was added and the volatiles were removed by evaporation. The residue was partitioned between methylene chloride and water and the aqueous layer was adjusted to pH8.5 with saturated aqueous sodium hydrogen carbonate solution. The organic layer was separated, washed with brine, dried (MgSO$_4$), and the solvent removed by evaporation. The residue was purified by column chromatography eluting with methylene chloride/methanol (95/5). The purified solid was triturated with ether, collected by filtration, washed with water and then ether, and dried under vacuum to give 4-chloro-6-methoxy-7-(2-(1,2,4-triazol-1-yl)ethoxy)quinazoline (756 mg, 65%).

$^1$H NMR Spectrum (DMSO d$_6$) 3.97(s, 3H); 4.65(dd, 2H); 4.70(dd, 2H); 7.39(s, 1H); 7.52(s, 1H); 7.99(s, 1H); 8.57(s, 1H); 8.89(s, 1H) MS-ESI: 306 [MH]$^+$

Example 98

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
| | Compound X | 100 |
| | Lactose Ph. Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph. Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph. Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph. Eur | 488.5 |
| | Magnesium stearate | 1.5 |

| (e) | Injection I | (50 mg/ml) |
|---|---|---|
| | Compound X | 5.0% w/v |
| | 1 N Sodium hydroxide solution | 15.0% v/v |
| | 0.1 N Hydrochloric acid (to adjust pH to 7.6) | |
| | Polyethylene glycol 400 | 4.5% w/v |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1 N Sodium hydroxide solution | 15.0% v/v |
| | Water for injection to 100% | |

| (g) | Injection III | (1 mg/ml, buffered to pH 6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

We claim:

1. A quinazoline derivative of the formula I:

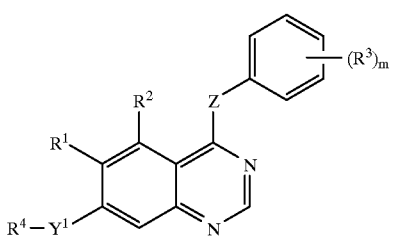

(I)

wherein:

$Y^1$ represents —O—, —S—, —$CH_2$—, —SO—, —$SO_2$—, —$NR^5CO$—, —$CONR^6$—, —$SO_2NR^7$—, —$NR^8SO_2$— or —$NR^9$—,
wherein $R^5$, $R^6$, $R^7$, $R^8$ and $R^9$ each independently represents hydrogen, $C_{1-3}$alkyl or $C_{1-3}$alkoxy$C_{2-3}$alkyl;

$R^1$ represents hydrogen, hydroxy, halogeno, nitro, trifluoromethyl, cyano, $C_{1-3}$alkyl, $C_{1-3}$alkoxy, $C_{1-3}$alkylthio, or $NR^{10}R^{11}$,
wherein $R^{10}$ and $R^{11}$, which may be the same or different, each represents hydrogen or $C_{1-3}$alkyl;

$R^2$ represents hydrogen, hydroxy, halogeno, $C_{1-3}$alkyl, $C_{1-3}$alkoxy, trifluoromethyl, cyano, amino or nitro;

m is an integer from 1 to 5;

$R^3$ represents hydroxy, halogeno, $C_{1-3}$alkyl, $C_{1-3}$alkoxy, $C_{1-3}$alkanoyloxy, trifluoromethyl, cyano, amino or nitro;

$R^4$ is selected from one of the following eight groups:

1) $X^1$, wherein $X^1$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{12}R^{13}$ and —$NR^{14}COR^{15}$,
wherein $R^{12}$, $R^{13}$, $R^{14}$ and $R^{15}$, which may be the same or different, each represents hydrogen, $C_{1-4}$alkyl or $C_{1-3}$alkoxy$C_{2-3}$alkyl;

2) $C_{1-5}$alkyl$X^1$, wherein $X^1$ is as defined hereinbefore;

3) $C_{2-5}$alkenyl$X^1$, wherein $X^1$ is as defined hereinbefore;

4) $C_{2-5}$alkynyl$X^1$, wherein $X^1$ is as defined hereinbefore;

5) $C_{1-5}$alkyl$Y^2X^1$, wherein $Y^2$ represents —O—, —S—, —SO—, —$SO2$—, —OCO—, —$NR^{16}CO$—, $CONR^{17}$—, —$SO_2NR^{18}$—, —$NR^{19}SO_2$— or —$NR^{20}$—,
wherein $R^{16}$, $R^{17}$, $R^{18}$, $R^{19}$ and $R^{20}$ each independently represents hydrogen, $C_{1-3}$alkyl or $C_{1-3}$alkoxy$C_{2-3}$alkyl, and $X^1$ is as defined hereinbefore;

6) $C_{2-5}$alkenyl$Y^3X^1$, wherein $Y^3$ represents —O—, —S—, —SO—, —$SO_2$—, —OCO—, —$NR^{21}CO$—, —$CONR^{22}$—, —$SO_2NR^{23}$—, —$NR^{24}SO_2$— or —$NR^{25}$—,
wherein $R^{21}$, $R^{22}$, $R^{23}$, $R^{24}$, and $R^{25}$ each independently represents hydrogen, $C_{1-3}$alkyl or $C_{1-3}$alkoxy$C_{2-3}$alkyl) and $X^1$ is as defined hereinbefore;

7) $C_{2-5}$alkynyl$Y^4X^1$, wherein $Y^4$ represents —O—, —S—, —SO—, —$SO_2$—, —OCO—, —$NR^{26}CO$—, —$CONR^{27}$—, —$SO_2NR^{28}$—, —$NR^{29}SO_2$— or —$NR^{30}$—,
wherein $R^{26}$, $R^{27}$, $R^{28}$, $R^{29}$ and $R^{30}$ each independently represents hydrogen, $C_{1-3}$alkyl or $C_{1-3}$alkoxy$C_{2-3}$alkyl, and $X^1$ is as defined hereinbefore; and 8) $C_{1-3}$alkyl$Y^5C_{1-3}$alkyl$X^1$, wherein $Y^5$ represents —O—, —S—, —SO—, —$SO_2$—, —$NR^{31}CO$—, —$CONR^{32}$—, $SO_2NR^{33}$—, —$NR^{34}SO_2$— or —$NR^{35}$—,
wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl, and $X^1$ is as defined hereinbefore;

Z represents —NH—;

with the proviso that where $R^4$ is selected from one of the groups 1), 2), and 5) above and $X^1$ is unsubstituted phenyl or substituted phenyl with 1 to 2 substituents selected from halogeno, $C_{1-4}$alkyl and $C_{1-4}$alkoxy, then m is an integer from 3 to 5;

and salts thereof.

2. A quinazoline derivative as claimed in claim 1 wherein $R^1$ represents hydrogen, hydroxy, methyl, ethyl, methoxy or ethoxy.

3. A quinazoline derivative as claimed in claim 1 or claim 2 wherein $R^2$ is hydrogen.

4. A quinazoline derivative as claimed in claim 1 wherein the phenyl group bearing $(R^3)_m$ is of the formula:

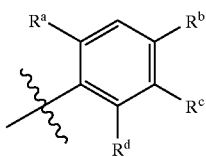

(IIa)

wherein:

R$^a$ represents hydrogen, methyl, fluoro or chloro;

R$^b$ represents hydrogen, methyl, methoxy, bromo, fluoro or chloro;

R$^c$ represents hydrogen or hydroxy; and

R$^d$ represents hydrogen, fluoro or chloro.

5. A quinazoline derivative as claimed in claim 1 wherein Y$^1$ represents —O—, —S—, —CH$_2$—, —NR$^5$CO—, —NR$^8$SO$_2$— or —NH—, wherein R$^5$ and R$^8$ each independently represent hydrogen, C$_{1-2}$alkyl or C$_{1-2}$alkoxyethyl.

6. A quinazoline derivative as claimed in claim 1 wherein the moiety X$^1$ in the group R$^4$ represents a pyridone group or a 5 or 6-membered aromatic heterocyclic group with 1 to 3 heteroatoms selected from O, N and S, which pyridone or heterocyclic group may carry up to 5 substituents.

7. A quinazoline derivative as claimed in claim 6 wherein the moiety X$^1$ represents a pyridone, pyridyl, imidazolyl, thiazolyl, thienyl, triazolyl or pyridazinyl group which may carry up to 5 substituents.

8. A quinazoline derivative as claimed in any one of claims 1, 6 and 7 wherein R$^4$ represents the group X$^1$—Y$^6$—(CH$_2$)$_n$— in which Y$^6$ is a direct bond —O—, —S—or —NH—, and n is an integer from 1 to 3.

9. A quinazoline derivative as claimed in claim 1 in the form of a pharmaceutically acceptable salt.

10. A pharmaceutical composition which comprises as active ingredient a quinazoline derivative of formula I as defined in claim 1 or a pharmaceutically acceptable salt thereof in association with a pharmaceutically acceptable excipient or carrier.

11. A method for producing an antiangiogenic and/or vascular permeability reducing effect in a warm-blooded animal in need of such treatment which comprises administering to said animal an effective amount of a compound of formula I or a pharmaceutically acceptable salt thereof as defined in claim 1.

12. A quinazoline derivative selected from the group consisting of:

4-(4-chloro-2-fluoroanilino)-6-methoxy-7-(2-(4-pyridyloxy)ethoxy)quinazoline;

4-(4-chloro-2-fluoroanilino)-6-methoxy-7-[2(4-oxo-1,4-dihydro-1-pyridyl)ethoxy]quinazoline;

4-(4-chloro-2-fluoroanilino)-7-(2-(imidazol-1-yl)ethoxy)-6-methoxyquinazoline;

4-(4-chloro-2-fluoroanilino)-6-methoxy-7-(3-(4-pyridyl)propoxy)quinazoline;

4-(4-chloro-2-fluoroanilino)-6-methoxy-7-(2-(4-pyridyl)ethoxy)quinazoline;

4-(4-chloro-2-fluoroanilino)-6-methoxy-7-((4-pyridyl)methoxy)quinazoline;

4-(4-chloro-2-fluoroanilino)-6-methoxy-7-(2-(2-methylimidazol-1-yl)ethoxy)quinazoline;

4-(4-chloro-2-fluoroanilino)-6-methoxy-7-(2-(-1-methylimidazol-2-ylthio)ethoxy)quinazoline;

4-(4-chloro-2-fluoroanilino)-6-methoxy-7-(2-(1,2,4-triazol-1-yl)ethoxy)quinazoline;

4-(4-chloro-2-fluoroanilino)-6-methoxy-7-(2-(N-(4-pyridyl)amino)ethoxy)quinazoline;

4-(4-chloro-2-fluoroanilino)-6-methoxy-7-(2-(1-methylimidazol-2-yl)ethoxy)quinazoline;

4-(4-chloro-2-fluoroanilino)-7-((2-cyano-4-pyridyl)methoxy)-6-methoxyquinazoline;

and salts thereof.

13. A quinazoline derivative selected from the group consisting of:

4-(3-hydroxy-4-methylanilino)-6-methoxy-7-(4-pyridylmethoxy)quinazoline;

4-(3-hydroxy-4-methylanilino)-6-methoxy-7-(2-pyridylmethoxy)quinazoline;

4-(3-hydroxy-4-methylanilino)-6-methoxy-7-(1-methylimidazol-2-ylmethoxy)quinazoline;

4-(3-hydroxy-4-methylanilino)6-methoxy-7-(2-methylthiazol-4-ylmethoxy)quinazoline;

7-(2-acetamidothiazol-4-ylmethoxy)-4-(3-hydroxy-4-methylanilino)-6-methoxyquinazoline;

4-(3-hydroxy-4-methylanilino)-6-methoxy-7-(3-(4-pyridyl)propoxy)quinazoline;

4-(2-fluoro-5-hydroxy-4-methylanilino)-6-methoxy-7-(3-(4-pyridyl)propoxy)quinazoline;

4-(2-fluoro-5-hydroxy-4-methylanilino)-6-methoxy-7-(4-pyridylmethoxy)quinazoline;

7-benzyloxy-4-(2-fluoro-5-hydroxy-4-methylanilino)-6-methoxyquinazoline;

4-(2-fluoro-5-hydroxy-4-methylanilino)-6-methoxy-7-((2-methylthiazol-4-yl)methoxy)quinazoline;

4-(2-fluoro-5-hydroxy-4-methylanilino)-7-(4-pyridylmethoxy)quinazoline;

4-(2-fluoro-5-hydroxy-4-methylanilino)-6-methoxy-7-((1-methylimidazol-2-yl)methoxy)quinazoline;

7-((2-acetamidothiazol-4-yl)methoxy)-4-(2-fluoro-5-hydroxy-4-methylanilino)-6-methoxyquinazoline;

7-benzyloxy-4-(4-chloro-2-fluoro-5-hydroxyanilino)-6-methoxyquinazoline;

4-(4-chloro-2-fluoro-5-hydroxyanilino)-6-methoxy-7-(3-(4-pyridyl)propoxy)quinazoline;

4-(2-fluoro-5-hydroxy-4-methylanilino)-7-(2-(imidazol-1-yl)ethoxy)-6-methoxyquinazoline;

4-(4-chloro-2-fluoro-5-hydroxyanilino)-7-(2-(imidazol-1-yl)ethoxy)-6-methoxyquinazoline;

4-(2-fluoro-5-hydroxy-4-methylanilino)-6-methoxy-7-(2-(4-pyridyl)ethoxy)quinazoline;

4-(2-fluoro-5-hydroxy-4-methylanilino)-6-methoxy-7-(3-thienylmethoxy)quinazoline;

4-(3-hydroxy-4-methylanilino)-6-methoxy-7-((1-methylbenzimidazol-2-yl)methoxy)quinazoline;

7-((2-chloro-6-methyl-4-pyridyl)methoxy)-4-(2-fluoro-5-hydroxy-4-methylanilino)-6-methoxyquinazoline;

4-(4-chloro-2-fluoro-5-hydroxyanilino)-6-methoxy-7-((4-pyridyl)methoxy)quinazoline;

7-((2-chloro-4-pyridyl)methoxy)-4-(2-fluoro-5-hydroxy-4-methylanilino)-6-methoxyquinazoline;

7-(3,4-difluorobenzyloxy)-4-(2-fluoro-5-hydroxy-4-methylanilino)-6-methoxyquinazoline;

4-(4-chloro-2-fluoro-5-hydroxyanilino)-6-methoxy-7-((1-methylimidazol-2-yl)methoxy)quinazoline;

4-(2-fluoro-5-hydroxy-4-methylanilino)-7-((1-methylimidazol-2-yl)methoxy)quinazoline;

4-(2-fluoro-5-hydroxy-4-methylanilino)-7-(2-(1,2,4-triazol-1-yl)ethoxy)quinazoline;

4-(4-chloro-2-fluoro-5-hydroxyanilino)-6-methoxy-7-(3-thienylmethoxy)quinazoline;

4-(4-chloro-2-fluoro-5-hydroxyanilino)-6-methoxy-7-(2-(4-pyridyl)ethoxy)quinazoline;

4-(2-fluoro-5-hydroxy-4-methylanilino)-7-((4-pyridyl)carboxamido)quinazoline;

and salts thereof.

14. A quinazoline derivative selected from the group consisting of:

4-(3-hydroxy-4-methylanilino)-6-methoxy-7-(3-pyridylmethoxy)quinazoline;

4-(3-hydroxy-4-methylanilino)-6-methoxy-7-(3-thienylmethoxy)quinazoline;

4-(4-chloro-2-fluoroanilino)-6-methoxy-7-(2-(2-pyridyloxy)ethoxy)quinazoline;

4-(4-chloro-2-fluoroanilino)-6-methoxy-7-(2-([N-methyl-N-(4-pyridyl)]amino)ethoxy)quinazoline;

4-(4-chloro-2-fluoroanilino)-6-methoxy-7-[2-(2oxo-1,2-dihydro-1-pyridyl)ethoxy]quinazoline;

7-(4-cyanobenzyloxy)-4-(2-fluoro-5-hydroxy-4-methylanilino)-6-methoxyquinazoline;

4-(4-chloro-2-fluoroanilino)-6-methoxy-7-(3-(2-methylimidazol-1-yl)propoxy)quinazoline;

4-(4-chloro-2-fluoroanilino)-6-methoxy-7-((2-methyl-4-pyridyl)methoxy)quinazoline;

4-(4-chloro-2-fluoroanilino)-6-methoxy-7-(3-(2-oxo-1,2-dihydro-1-pyridyl)propoxy)quinazoline;

4-(4-chloro-2-fluoroanilino)-6-methoxy-7-(3-(1-methylimidazol-2-ylthio)propoxy)quinazoline;

4-(4-chloro-2-fluoroanilino)-6-methoxy-7-(3-(4-pyridyloxy)propoxy)quinazoline;

4-(4-chloro-2-fluoroanilino)-6-methoxy-7-(2-(4-pyridylthio)ethoxy)quinazoline;

4-(4-chloro-2-fluoroanilino)-6-methoxy-7-(2-(3-pyridyloxy)ethoxy)quinazoline;

7-benzyloxy-4-(2-fluoro-5-hydroxy-4-methylanilino)quinazoline;

7-benzyloxy-4-(4-chloro-2-fluoro-5-hydroxyanilino)quinazoline;

4-(4-chloro-2-fluoro-5-hydroxyanilino)-6-methoxy-7-((2-methylthiazol-4-yl)methoxy)quinazoline;

4-(4-chloro-2-fluoroanilino)-6-methoxy-7-(3-thienylmethoxy)quinazoline;

4-(4-chloro-2-fluoroanilino)-6-methoxy-7-(2-(N-methyl-N-(pyridazin-4-yl)amino)ethoxy)quinazoline;

4-(4-chloro-2-fluoroanilino)-6-methoxy-7-(2-(N-methyl-N-(6-methylpyrimidin-4-yl)amino)ethoxy)quinazoline;

4-(4-chloro-2-fluoroanilino)-7-(2-(3,5-dimethyl-[1,2,4]-triazol-4-yl)ethoxy)-6-methoxyquinazoline;

4-(4-chloro-2-fluoroanilino)-7-(2-(2,4-dimethylimidazol-1-yl)ethoxy)-6-methoxyquinazoline;

4-(4-chloro-2-fluoroanilino)-7-(2-(2,5-dimethylimidazol-1-yl)ethoxy)-6-methoxyquinazoline;

4-(3-hydroxyanilino)-7-(2-(imidazol-1-yl)ethoxy)-6-methoxyquinazoline;

4-(4-chloro-2-fluoroanilino)-6-methoxy-7-(2-(1,2,4-triazol-4-yl)ethoxy)quinazoline;

4-(4-bromo-2-fluoroanilino)-7-(2-([1,2,4]-triazol-1-yl)ethoxy)-6-methoxyquinazoline;

and salts thereof.

* * * * *